US012653732B2

(12) United States Patent
Bewick-Sonntag et al.

(10) Patent No.: US 12,653,732 B2
(45) Date of Patent: Jun. 16, 2026

(54) ABSORBENT ARTICLE HAVING MULTIPLE ZONES

(71) Applicant: The Procter & Gamble Company, Cincinnati, OH (US)

(72) Inventors: Christopher Philip Bewick-Sonntag, Cincinnati, OH (US); Clint Adam Morrow, Union, KY (US); Callida Williams Ludher, Cincinnati, OH (US); John David Norcom, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1157 days.

(21) Appl. No.: 15/970,093

(22) Filed: May 3, 2018

(65) Prior Publication Data

US 2018/0318151 A1 Nov. 8, 2018

Related U.S. Application Data

(60) Provisional application No. 62/500,920, filed on May 3, 2017.

(51) Int. Cl.
*A61F 13/535* (2006.01)
*A61F 13/15* (2006.01)
(Continued)

(52) U.S. Cl.
CPC .......... *A61F 13/535* (2013.01); *A61F 13/475* (2013.01); *A61F 13/51305* (2013.01);
(Continued)

(58) Field of Classification Search
CPC .............. A61F 13/535; A61F 13/51394; A61F 13/51305; A61F 13/53; A61F 13/534; A61F 13/475; A61F 13/539; A61F 13/84; A61F 13/4704; A61F 13/5116; A61F 13/515; A61F 13/15731; A61F 13/5616; A61F 13/536; A61F 13/47; A61F 13/49; A61F 13/494; A61F 13/471; A61F 13/47209; A61F 2013/15422; A61F 2013/15146; A61F 2013/1513; A61F 2013/5284;
(Continued)

(56) References Cited

U.S. PATENT DOCUMENTS

| | | |
|---|---|---|
| 4,321,924 A | 3/1982 | Ahr |
| 4,425,130 A | 1/1984 | DesMarais |

(Continued)

FOREIGN PATENT DOCUMENTS

| | | |
|---|---|---|
| CN | 1430942 A | 7/2003 |
| CN | 104837452 A | 8/2015 |

(Continued)

OTHER PUBLICATIONS

Definition of irregular Cambridge Dictionary (Year: 2023).*
PCT International Search Report, mailed Sep. 14, 2018 (13 pages).

*Primary Examiner* — Rebecca E Eisenberg
*Assistant Examiner* — Gabriella E Burnette
(74) *Attorney, Agent, or Firm* — Sarah M. DeCristofaro

(57) ABSTRACT

An absorbent article is disclosed. The absorbent article having a topsheet, a backsheet, and an absorbent core structure having one or more layers. The absorbent article has multiple zones.

18 Claims, 35 Drawing Sheets

(51) Int. Cl.

| | |
|---|---|
| *A61F 13/47* | (2006.01) |
| *A61F 13/475* | (2006.01) |
| *A61F 13/511* | (2006.01) |
| *A61F 13/513* | (2006.01) |
| *A61F 13/515* | (2006.01) |
| *A61F 13/53* | (2006.01) |
| *A61F 13/534* | (2006.01) |
| *A61F 13/539* | (2006.01) |
| *A61F 13/56* | (2006.01) |
| *A61F 13/84* | (2006.01) |

(52) U.S. Cl.
CPC ........ *A61F 13/51394* (2013.01); *A61F 13/53* (2013.01); *A61F 13/534* (2013.01); *A61F 13/539* (2013.01); *A61F 13/84* (2013.01); *A61F 2013/1513* (2013.01); *A61F 2013/15146* (2013.01); *A61F 2013/15284* (2013.01); *A61F 2013/15422* (2013.01); *A61F 13/15731* (2013.01); *A61F 13/4704* (2013.01); *A61F 13/5116* (2013.01); *A61F 13/515* (2013.01); *A61F 2013/530233* (2013.01); *A61F 2013/53024* (2013.01); *A61F 2013/530299* (2013.01); *A61F 13/5616* (2013.01); *A61F 2013/8497* (2013.01)

(58) Field of Classification Search
CPC .... A61F 2013/8497; A61F 2013/53024; A61F 2013/530299; A61F 2013/530233
See application file for complete search history.

(56) References Cited

U.S. PATENT DOCUMENTS

| | | | |
|---|---|---|---|
| 4,589,876 A | | 5/1986 | Van Tilburg |
| 4,950,264 A | | 8/1990 | Osborn, III |
| 5,149,720 A | | 9/1992 | DesMarais et al. |
| 5,287,707 A | | 2/1994 | Kitayama |
| 5,500,451 A | | 3/1996 | Goldman et al. |
| 5,518,801 A | * | 5/1996 | Chappell .......... A61F 13/15707 |
| | | | 428/152 |
| 5,628,097 A | | 5/1997 | Benson et al. |
| 6,369,121 B1 | | 4/2002 | Catalfamo et al. |
| 7,172,801 B2 | | 2/2007 | Hoying et al. |
| 7,198,742 B2 | | 4/2007 | Gerndt |
| 7,410,683 B2 | | 8/2008 | Curro et al. |
| 7,507,459 B2 | | 3/2009 | Turner et al. |
| 7,553,532 B2 | | 6/2009 | Turner et al. |
| 7,648,752 B2 | | 1/2010 | Hoying et al. |
| 7,682,686 B2 | | 3/2010 | Curro et al. |
| 7,718,243 B2 | | 5/2010 | Curro et al. |
| 7,732,657 B2 | | 6/2010 | Hammons et al. |
| 7,754,050 B2 | | 7/2010 | Redd et al. |
| 7,789,994 B2 | | 9/2010 | Hupp et al. |
| 7,838,099 B2 | | 11/2010 | Curro et al. |
| 7,935,207 B2 | | 5/2011 | Zhao et al. |
| 7,967,801 B2 | | 6/2011 | Hammons et al. |
| 8,124,827 B2 | | 2/2012 | Tamburro et al. |
| 8,153,226 B2 | | 4/2012 | Curro et al. |
| 8,262,633 B2 | | 9/2012 | Larson et al. |
| 8,558,054 B2 | * | 10/2013 | Noda .................... A61F 13/532 |
| | | | 604/380 |
| 8,569,572 B2 | | 10/2013 | Hammons |
| 8,674,169 B2 | | 3/2014 | Brennan et al. |
| 8,715,258 B2 | * | 5/2014 | Munakata ............. A61F 13/533 |
| | | | 604/385.101 |
| 8,728,049 B2 | | 5/2014 | Hammons et al. |
| 9,408,761 B2 | | 8/2016 | Xu et al. |
| 9,566,196 B2 | | 2/2017 | Carlucci |

| | | | |
|---|---|---|---|
| 10,016,779 B2 | | 7/2018 | McNeil et al. |
| 10,045,888 B2 | | 8/2018 | Strube et al. |
| 10,052,242 B2 | * | 8/2018 | Bianchi ................ A61F 13/539 |
| 2003/0078553 A1 | * | 4/2003 | Wada ................ A61F 13/51394 |
| | | | 604/361 |
| 2004/0127875 A1 | * | 7/2004 | Hammons ........ A61F 13/51104 |
| | | | 604/385.01 |
| 2005/0124951 A1 | * | 6/2005 | Kudo ................ A61F 13/47218 |
| | | | 604/380 |
| 2006/0116653 A1 | | 6/2006 | Munakata et al. |
| 2010/0032860 A1 | * | 2/2010 | Hernandez .......... A61F 13/4756 |
| | | | 264/175 |
| 2010/0035014 A1 | * | 2/2010 | Hammons ......... A61F 13/51305 |
| | | | 428/88 |
| 2010/0036338 A1 | * | 2/2010 | Hammons ......... A61F 13/51305 |
| | | | 604/367 |
| 2010/0036351 A1 | * | 2/2010 | Larson .................. A61F 13/511 |
| | | | 604/385.01 |
| 2010/0228209 A1 | | 9/2010 | Carlucci et al. |
| 2010/0262104 A1 | | 10/2010 | Carlucci et al. |
| 2011/0036351 A1 | | 2/2011 | Conrad et al. |
| 2011/0060301 A1 | * | 3/2011 | Nishikawa ........ A61F 13/15699 |
| | | | 604/358 |
| 2011/0196330 A1 | * | 8/2011 | Hammons ......... A61F 13/51305 |
| | | | 604/383 |
| 2012/0037474 A1 | * | 2/2012 | Kameda ............ A61F 13/15772 |
| | | | 198/339.1 |
| 2014/0228795 A1 | * | 8/2014 | Castanares .............. A61F 13/84 |
| | | | 604/385.01 |
| 2015/0173978 A1 | * | 6/2015 | Carlucci ............. A61F 13/4758 |
| | | | 604/385.01 |
| 2015/0313770 A1 | * | 11/2015 | Hubbard, Jr. ......... A61F 13/534 |
| | | | 604/369 |
| 2015/0335498 A1 | * | 11/2015 | Hubbard, Jr. ......... A61L 15/425 |
| | | | 604/378 |
| 2015/0374560 A1 | | 12/2015 | Hubbard, Jr. |
| 2015/0374561 A1 | | 12/2015 | Hubbard, Jr. et al. |
| 2016/0287452 A1 | | 10/2016 | Hubbard, Jr. et al. |
| 2016/0346805 A1 | | 12/2016 | McNeil et al. |
| 2017/0071795 A1 | | 3/2017 | Bewick-Sonntag et al. |
| 2017/0119587 A1 | | 5/2017 | Bewick-Sonntag et al. |
| 2017/0119588 A1 | | 5/2017 | Bewick-Sonntag et al. |
| 2017/0119589 A1 | | 5/2017 | Bewick-Sonntag et al. |
| 2017/0119593 A1 | | 5/2017 | Hubbard, Jr. et al. |
| 2017/0119594 A1 | | 5/2017 | Bewick-Sonntag et al. |
| 2017/0119595 A1 | | 5/2017 | Carla et al. |
| 2017/0119597 A1 | | 5/2017 | Bewick-Sonntag et al. |
| 2017/0119598 A1 | | 5/2017 | Bewick-Sonntag et al. |
| 2017/0119600 A1 | | 5/2017 | Bewick-Sonntag et al. |
| 2017/0267827 A1 | | 9/2017 | Rowan et al. |
| 2017/0319401 A1 | | 11/2017 | Ludher et al. |
| 2017/0319402 A1 | | 11/2017 | Morrow et al. |
| 2017/0319403 A1 | | 11/2017 | Bewick-Sonntag et al. |
| 2017/0319404 A1 | | 11/2017 | Bewick-Sonntag et al. |
| 2017/0360618 A1 | | 12/2017 | Mullane et al. |
| 2018/0110660 A1 | | 4/2018 | Bewick-Sonntag et al. |
| 2018/0168884 A1 | | 6/2018 | Hubbard, Jr. et al. |
| 2018/0169832 A1 | | 6/2018 | Viens et al. |
| 2018/0228656 A1 | | 8/2018 | Schneider et al. |
| 2018/0228666 A1 | | 8/2018 | Trinkaus et al. |
| 2018/0228667 A1 | | 8/2018 | Schneider et al. |
| 2018/0228668 A1 | | 8/2018 | Schneider et al. |
| 2018/0228669 A1 | | 8/2018 | Schneider et al. |
| 2019/0314218 A1 | * | 10/2019 | Arora ................ A61F 13/51104 |
| 2019/0380887 A1 | * | 12/2019 | Ashraf .................... A61F 13/47 |

FOREIGN PATENT DOCUMENTS

| | | | |
|---|---|---|---|
| CN | 106456824 A | | 2/2017 |
| CN | 106456825 A | | 2/2017 |
| EP | 1990033 A1 | | 11/2008 |

* cited by examiner

ABSORBENT ARTICLE HAVING MULTIPLE ZONES

FIELD OF THE INVENTION

The present invention relates to an absorbent structure that exhibits beneficial physical and performance properties. Specifically the ability to exhibit desirable shape properties during use. The absorbent structure is useful in absorbent articles such as diapers, incontinent briefs, training pants, diaper holders and liners, sanitary hygiene garments, and the like.

BACKGROUND OF THE INVENTION

One of the goals of an absorbent article is to absorb fluid without being noticeable to the user or others. Ideally, an article would be created that has the flexibility of a cloth undergarment while being capable of absorbing fluid rapidly into the core. However, there is often a tradeoff between comfort and rate of absorption.

The anatomical region in which pads are worn is geometrically complex and dynamic. For example, during walking, the geometry of the pubis/labia through the gluteal groove becomes cyclically asymmetric in both the coronal and transverse planes. Underwear and clothing are designed to accommodate the changing geometry of the body during motion. Clothing that moves with the body without restricting it is considered comfortable and has low wearing awareness. The material properties and construction techniques of apparel enable this dynamic fit. In general, panties are thin, flexible, and extensible.

Pads are affixed to the panty crotch in order to absorb menstrual fluid as it exits the body.

Pads are thicker, stiffer, and less extensible than panties. Therefore, the dynamic material properties of the panty are negatively affected by the presence of a pad. Worn alone, panties follow and accommodate the natural movement of the body's anatomy. With a pad, the panty can no longer follow this natural movement. This negatively affects comfort, and increases wearing awareness of the pad. This is undesirable because consumers are seeking a pad wearing experience that feels more like wearing just their underwear. Pads are especially noticeable to wearers at the gluteal groove; this is an area of high motion during regular activities such as walking. High motions zones are where the most stretch and movement is needed in clothing. Hence, an absorbent pad covers areas that exhibit different amounts of motion. Whereas the front covers a low motion zone, the back covers the gluteal groove which is a high motion zone.

Current products may rely on embossing channels or selectively removing parts of the core to create different flexibilities in different portions of the product. However, these products still disrupt the natural movement and fit of panties and can negatively impact the absorption performance of the pad.

Lastly, even when designed to have a certain level of flexibility, many products are not capable of maintaining the initial benefit throughout the product usage cycle. For example, traditional cellulose based thick products exhibit high initial stiffness, in an attempt to balance the deformation, bunching, and degradation effects of wearing. Traditional in market products often composed of airlaid absorbent materials are thinner and more comfortable, with less initial stiffness, but are prone to structural collapse as the products are worn and loaded by the wearer.

As such, there exists the need to develop an absorbent structure that can exhibit the desirable shape properties needed to create a flexible product that can move with the user and maintain the absorbency needed.

SUMMARY OF THE INVENTION

An absorbent article is disclosed. The absorbent article comprises a topsheet, a backsheet, and an absorbent core structure comprising one or more layers, a first boundary, a second boundary and a boundary convergence area, wherein the boundary convergence area is located at a point greater than 50% of the total length of the article along the longitudinal axis when measured from the front edge of the absorbent article.

An absorbent article is disclosed. The absorbent article comprises a topsheet, a backsheet, and an absorbent core structure comprising one or more layers, a first boundary, a second boundary and a boundary convergence area. The boundary convergence area is located at a point greater than 50% of the total length of the article along the longitudinal axis when measured from the front edge of the absorbent article. The absorbent core comprises a heterogeneous mass layer.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
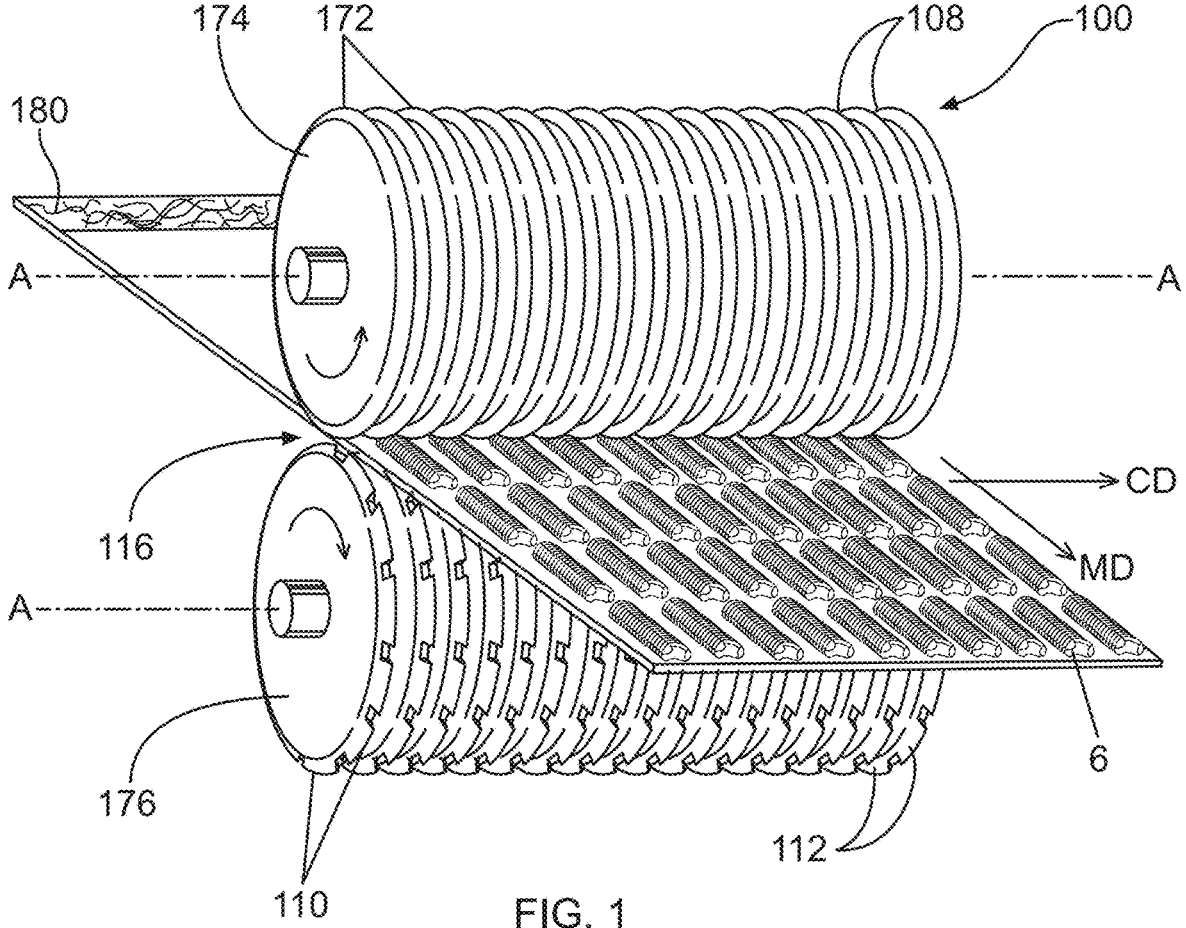
FIG. 1 is a perspective view of an apparatus for forming the web for use in the present invention.

As used herein, the term "absorbent core structure" refers to an absorbent core that is has two or more absorbent core layers. Each absorbent core layer is capable acquiring and transporting or retaining fluid.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, "boundary convergence area" refers to an area or point of juncture wherein two or more zone boundaries transition or intermingle. The boundary convergence area is bound by two or more zones. The boundary convergence area is a region in which two or more prevailing mechanical properties meet or interact.

As used herein, "complex liquids" are defined as fluids that are non-Newtonian, whose rheological properties are complex that change with shear and commonly shear thin. Such liquids commonly contain more than one phase (red blood cells plus vaginal mucous) that may phase separate on contact with topsheets and absorbent materials. In addition, complex liquids such as menstrual fluid may contain long chain proteins exhibiting stringy properties, high cohesive force within a droplet allowing for droplet elongation without breaking. Complex liquids may have solids (menstrual and runny feces).

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin or a panty liner or an adult incontinence article or a baby diaper or a wound dressing. The absorbent structure of the present invention will be herein described in the context of a typical absorbent article, such as, for example, a sanitary napkin. Typically, such articles can comprise a liquid pervious topsheet, a backsheet and an absorbent core intermediate the topsheet and the backsheet.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that can be part of a fibrous structure. Fibers can be natural or synthetic. Fibers can be absorbent or non-absorbent.

A "fibrous structure" as used herein, refers to materials which can be broken into one or more fibers. A fibrous structure can be absorbent or adsorbent. A fibrous structure can exhibit capillary action as well as porosity and permeability.

As used herein the term "fluid continuity" refers to a property of an absorbent core or a layer within an absorbent core to be continuous throughout the layer thereby allowing fluid inserted into the absorbent core or layer to be able to wick to any other portion of the absorbent core or layer.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, TN. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in an article of the present invention can range from 10 gsm to 100 gsm, depending on the ultimate use of the web.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "strata" or "stratum" relates to one or more layers wherein the components within the stratum are intimately combined without the necessity of an adhesive, pressure bonds, heat welds, a combination of pressure and heat bonding, hydro-entangling, needlepunching, ultrasonic bonding, or similar methods of bonding known in the art such that individual components may not be wholly separated from the stratum without affecting the physical structure of the other components. The skilled artisan should understand that while separate bonding is unnecessary between the strata, bonding techniques could be employed to provide additional integrity depending on the intended use.

As used herein, a "tuft" or chad relates to discrete integral extensions of the fibers of a nonwoven web. Each tuft can comprise a plurality of looped, aligned fibers extending outwardly from the surface of the web. In another embodiment each tuft can comprise a plurality of non-looped fibers that extend outwardly from the surface of the web. In another embodiment, each tuft can comprise a plurality of fibers which are integral extensions of the fibers of two or more integrated nonwoven webs.

As used herein, a "well" or "wells" relates to one or more funnel shaped volumetric spaces wherein a portion of a fibrous layer has been integrated into a second fibrous layer without creating a higher density zone. The wells may be circular or elongated circular patterns where there is a smooth transition from a horizontal plane to a vertical plane along the surface of the well. Wells are further defined in that one or more fibers from the first fibrous layer and one or more fibers from the second fibrous layer create the outer surface of the well within the same x-y plane. The second fibrous layer is either a fluid transfer or a fluid storage layer. A well may exhibit variations in the density of the side wall or the distal end, however the density of the distal end is not greater than the average density of the original first fibrous layer.

While particular embodiments of the present invention have been illustrated and described, it would be obvious to those skilled in the art that various other changes and modifications can be made without departing from the spirit and scope of the invention.

General Summary

An absorbent article structure is disclosed. The absorbent article has one of a topsheet, a secondary topsheet, or both combined with a fibrous web having a high capacity absorbent.

The fibrous web may be a heterogeneous mass comprising a fibrous web and one or more pieces of open cell foam intermixed within the fibrous web and/or enrobing one or more fibers within the fibrous web.

The fibrous web may be the upper layer of an absorbent core. The absorbent core may be a two layer system wherein the upper layer is heterogeneous mass layer comprising one or more enrobeable elements and one or more discrete open-cell foam pieces. The upper layer heterogeneous mass layer may be a stratum as defined above. The lower layer may be an absorbent layer that comprises superabsorbent polymer. The absorbent core structure may comprise additional layers below the absorbent layer that comprises superabsorbent polymer. The upper layer heterogeneous mass layer may be integrated with a topsheet using formation means.

The absorbent core structure may comprise a heterogeneous mass layer or may utilize methods or parameters such as those described in US Patent Publication No. 2015-0335498, filed May 19, 2015; US Patent Publication No. 2015-0374560, Jun. 25, 2015; US Patent Publication No. 2015-0374561 filed Jun. 26, 2015; US Patent Publication No. 2016-0346805 filed Mar. 23, 2016; US Patent Publication No. 2015-0374561 filed Jun. 25, 2015; US Patent Publication No. 2016-0287452 filed Mar. 30, 2016; US Patent Publication No. 2017-0071795 filed Nov. 4, 2016; U.S. patent application Ser. No. 15/344,273 filed Nov. 4, 2016; U.S. patent application Ser. No. 15/344,294 filed Nov. 4, 2016; US Patent Publication No. 2015-0313770 filed May 5, 2015; US Patent Publication No. 2016-0375458 filed Jun. 28, 2016; U.S. patent application Ser. No. 15/344,050 filed Nov. 4, 2016; U.S. patent application Ser. No. 15/344,117 filed Nov. 4, 2016; U.S. patent application Ser. No. 15/344, 177 filed Nov. 4, 2016; U.S. patent application Ser. No. 15/344,198 filed Nov. 4, 2016; U.S. patent application Ser. No. 15/344,221 filed Nov. 4, 2016; U.S. patent application Ser. No. 15/344,239 filed Nov. 4, 2016; U.S. patent application Ser. No. 15/344,255 filed Nov. 4, 2016; U.S. patent application Ser. No. 15/464,733 filed Nov. 4, 2016; U.S. Provisional Patent Application No. 62/332,549 filed May 6, 2016; U.S. Provisional Patent Application No. 62/332,472 filed May 5, 2016; U.S. Provisional Patent Application No. 62/437,208 filed Dec. 21, 2016; U.S. Provisional Patent Application No. 62/437,225 filed Dec. 21, 2016; U.S. Provisional Patent Application No. 62/437,241 filed Dec. 21, 2016; or U.S. Provisional Patent Application No. 62/437, 259 filed Dec. 21, 2016. The heterogeneous mass layer has a depth, a width, and a height.

The absorbent core structure may comprise a substrate and superabsorbent polymer layer as those described in U.S. Pat. No. 8,124,827 filed on Dec. 2, 2008 (Tamburro); U.S. application Ser. No. 12/718,244 published on Sep. 9, 2010; U.S. application Ser. No. 12/754,935 published on Oct. 14, 2010; or U.S. Pat. No. 8,674,169 issued on Mar. 18, 2014.

The one or more discrete portions of foam pieces enrobe the enrobeable elements. The discrete portions of foam pieces are open-celled foam. In an embodiment, the foam is a High Internal Phase Emulsion (HIPE) foam. In an embodiment, one continuous piece of open cell foam may enrobe multiple enrobeable elements, such as, for example, the fibers that make up the upper layer of a nonwoven web.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The heterogeneous mass layer contains one or more discrete open-cell foam pieces foams that are integrated into the heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass layer may have void space found between the enrobeable elements (e.g. fibers), between the enrobeable elements and the enrobed enrobeable elements (e.g. fibers enrobed by open cell foam), and between enrobed enrobeable elements. The void space may contain gas. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the heterogeneous mass, such as for example, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

In an embodiment, a discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

In an embodiment, the open-cell foam pieces may enrobe an enrobeable element such that the enrobeable element is enrobed along the enrobeable elements axis for between 5% and 95% of the length along the enrobeable element's axis. For example, a single fiber may be enrobed along the length of the fiber for a distance greater than 50% of the entire length of the fiber. In an embodiment, an enrobeable element may have between 5% and 100% of its surface area enrobed by one or more open-cell foam pieces.

In an embodiment, two or more open-cell foam pieces may enrobe the same enrobeable element such that the enrobeable element is enrobed along the enrobeable elements axis for between 5% and 100% of the length along the enrobeable element's axis.

The open-cell foam pieces enrobe the enrobeable elements such that a layer surrounds the enrobeable element at a given cross section. The layer surrounding the enrobeable element at a given cross section may be between 0.01 mm to 100 mm such as, for example, 0.1 mm, 0.2 mm, 0.3 mm, 0.4 mm, 0.5 mm, 0.6 mm, 0.7 mm, 0.8 mm, 0.9 mm, 1.0 mm, 1.2 mm, 1.4 mm, 1.6 mm, 1.8 mm, 2.0 mm, 2.2 mm, 2.4 mm, 2.6 mm, 2.8 mm, or 3 mm. The layer may not be equivalent in dimension at all points along the cross section of the enrobeable element. For example, in an embodiment, an enrobeable element may be enrobed by 0.5 mm at one point along the cross section and by 1.0 mm at a different point along the same cross section.

The open-cell foam pieces are considered discrete in that they are not continuous throughout the entire heterogeneous mass layer. Not continuous throughout the entire heterogeneous mass layer represents that at any given point in the heterogeneous mass layer, the open-cell absorbent foam is not continuous in at least one of the cross sections of a longitudinal, a vertical, and a lateral plane of the heterogeneous mass layer. In a non-limiting embodiment, the absorbent foam is not continuous in the lateral and the vertical planes of the cross section for a given point in the heterogeneous mass layer. In a non-limiting embodiment, the absorbent foam is not continuous in the longitudinal and the vertical planes of the cross section for a given point in the heterogeneous mass layer. In a non-limiting embodiment, the absorbent foam is not continuous in the longitudinal and the lateral planes of the cross section for a given point in the heterogeneous mass layer.

In an embodiment wherein the open-cell foam is not continuous in at least one of the cross sections of longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. In a non-limiting embodiment, a foam piece may be surrounded by the elements that make up the enrobeable elements. In a non-limiting embodiment a foam piece may be located on the outer perimeter of the heterogeneous mass such that only a portion of the foam piece is entangled with the elements of the heterogeneous mass.

In a non-limiting embodiment, the open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. In a non-limiting embodiment the open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces.

The open cell foam pieces may be impregnated prior to polymerization into or onto two or more different enrobeable elements that are combined to create a heterogeneous mixture of enrobeable elements. The two or more different enrobeable elements may be intertwined such that one enrobeable element may be surrounded by multiples of the second enrobeable element, such as, for example by using more than one type of fiber in a mixture of fibers or by coating one or more fibers with surfactant. The two or more different enrobeable elements may be layered within the heterogeneous mass along any of the vertical, longitudinal, and/or lateral planes such that the enrobeable elements are profiled within the heterogeneous mass for an enrobeable element inherent property or physical property, such as, for example, hydrophobicity, fiber diameter, fiber or composition. It is understood that any inherent property or physical property of the enrobeable elements listed is contemplated herein.

The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

Dependent upon the desired foam density, polymer composition, specific surface area, or pore size (also referred to as cell size), the open-celled foam may be made with different chemical composition, physical properties, or both. For instance, dependent upon the chemical composition, an open-celled foam may have a density of 0.0010 g/cc to about 0.25 g/cc. Preferred 0.04 g/cc.

Open-cell foam pore sizes may range in average diameter of from 1 to 800 $\mu$m, such as, for example, between 50 and 700 $\mu$m, between 100 and 600 $\mu$m, between 200 and 500 $\mu$m, between 300 and 400 $\mu$m.

In some embodiments, the foam pieces have a relatively uniform cell size. For example, the average cell size on one major surface may be about the same or vary by no greater than 10% as compared to the opposing major surface. In other embodiments, the average cell size of one major surface of the foam may differ from the opposing surface. For example, in the foaming of a thermosetting material it is not uncommon for a portion of the cells at the bottom of the cell structure to collapse resulting in a lower average cell size on one surface.

The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1um in average diameter size are in fluid communication with at least one adjoining cell.

In addition to being open-celled, in certain embodiments foams are sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

In certain embodiments, for example when used in certain absorbent articles, an open-cell foam may be flexible and exhibit an appropriate glass transition temperature (Tg). The Tg represents the midpoint of the transition between the glassy and rubbery states of the polymer.

In certain embodiments, the Tg of this region will be less than about 200° C. for foams used at about ambient temperature conditions, in certain other embodiments less than about 90° C. The Tg may be less than 50° C.

The open-cell foam pieces may be distributed in any suitable manner throughout the heterogeneous mass. In an embodiment, the open-cell foam pieces may be profiled along the vertical axis such that smaller pieces are located above larger pieces. Alternatively, the pieces may be profiled such that smaller pieces are below larger pieces. In another embodiment, the open-cell pieces may be profiled along a vertical axis such that they alternate in size along the axis.

In an embodiment the open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

In an embodiment, the open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. In an embodiment, the open-cell foam pieces may be distributed in a manner that forms a design or shape when viewed from a top planar view. The open-cell foam pieces may be distributed in a manner that forms stripes, ellipticals, squares, or any other known shape or pattern.

In an embodiment, different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

In an embodiment, the open-celled foam is a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. In certain embodiments, the aqueous phase to oil phase ratio is between about 10:1 and about 75:1, and in certain other embodiments the aqueous phase to oil phase ratio is between about 13:1 and about 65:1. This is termed the "water-to-oil" or W:O ratio and can be used to determine the density of the resulting polyHIPE foam. As discussed, the oil phase may contain one or more of monomers, co-monomers, photo-initiators, cross-linkers, and emulsifiers, as well as optional components. The water phase will contain water and in certain embodiments one or more components such as electrolyte, initiator, or optional components.

The open-cell foam can be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, and in certain embodiments, after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE can then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (Des-Marais) issued Oct. 27, 1998; and U.S. Pat. No. 6,369,121 (Catalfamo et al.) issued Apr. 9, 2002.

The emulsion can be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. In certain embodiments, foam pieces can be squeezed free of most of the aqueous phase by using compression, for example by running the heterogeneous mass comprising the foam pieces through one or more pairs of nip rollers. The nip rollers can be positioned such that they squeeze the aqueous phase out of the foam pieces. The nip rollers can be porous and have a vacuum applied from the inside such that they assist in drawing aqueous phase out of the foam pieces. In certain embodiments, nip rollers can be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller can be pressurized while the other, for example the second nip roller, can be evacuated, so as to both blow and draw the aqueous phase out the of the foam. The nip rollers may also be heated to assist in removing the aqueous phase. In certain embodiments, nip rollers are only applied to non-rigid foams, that is, foams whose walls would not be destroyed by compressing the foam pieces.

In certain embodiments, in place of or in combination with nip rollers, the aqueous phase may be removed by sending the foam pieces through a drying zone where it is heated, exposed to a vacuum, or a combination of heat and vacuum exposure. Heat can be applied, for example, by running the foam though a forced air oven, IR oven, microwave oven or radiowave oven. The extent to which a foam is dried depends on the application. In certain embodiments, greater than 50% of the aqueous phase is removed. In certain other embodiments greater than 90%, and in still other embodiments greater than 95% of the aqueous phase is removed during the drying process.

In an embodiment, open-cell foam is produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photo-initiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking co-monomer, or cross-linker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of cross-linkers contain a mixture of acrylate and methacrylate moieties, such as ethylene glycol acrylate-methacrylate and neopentyl glycol acrylate-methacrylate. The ratio of methacrylate:acrylate group in the mixed cross-linker may be varied from 50:50 to any other ratio as needed.

Any third substantially water-insoluble co-monomer may be added to the oil phase in weight percentages of from about 0% to about 15% by weight of the oil phase, in certain embodiments from about 2% to about 8%, to modify properties of the HIPE foams. In certain embodiments, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type can have styrene and vinyl chloride.

The oil phase may further contain an emulsifier used for stabilizing the HIPE. Emulsifiers used in a HIPE can include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they can have between about 1% and about 20%, in certain embodiments from about 2% to about 15%, and in certain other embodiments from about 3% to about 12% by weight of the oil phase. In certain embodiments, co-emulsifiers may also be used to provide additional control of cell size, cell size distribution, and emulsion stability, particularly at higher temperatures, for example greater than about 65° C. Examples of co-emulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. In certain embodiments, ditallow dimethyl ammonium methyl sulfate (DTDMAMS) may be used as a co-emulsifier.

The oil phase may comprise a photo-initiator at between about 0.05% and about 10%, and in certain embodiments between about 0.2% and about 10% by weight of the oil phase. Lower amounts of photo-initiator allow light to better penetrate the HIPE foam, which can provide for polymerization deeper into the HIPE foam. However, if polymerization is done in an oxygen-containing environment, there should be enough photo-initiator to initiate the polymerization and overcome oxygen inhibition. Photo-initiators can respond rapidly and efficiently to a light source with the production of radicals, cations, and other species that are capable of initiating a polymerization reaction. The photo-initiators used in the present invention may absorb UV light at wavelengths of about 200 nanometers (nm) to about 800 nm, in certain embodiments about 200 nm to about 350 nm. If the photo-initiator is in the oil phase, suitable types of oil-soluble photo-initiators include benzyl ketals, α-hydroxyalkyl phenones, α-amino alkyl phenones, and acylphospine oxides. Examples of photo-initiators include 2,4,6-[trimethylbenzoyldiphosphine]oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-

[4-(methyl thio)phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-11-[4-(1-methylvinyl)phenyl]propanone] (sold by Lambeth spa, Gallarate, Italy as ESACURE® KIP EM.

The dispersed aqueous phase of a HIPE can have water, and may also have one or more components, such as initiator, photo-initiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, co-monomers, and cross-linkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counter-ions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain embodiments, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine) dihydrochloride, and other suitable azo initiators. In certain embodiments, to reduce the potential for premature polymerization which may clog the emulsification system, addition of the initiator to the monomer phase may be just after or near the end of emulsification.

Photo-initiators present in the aqueous phase may be at least partially water soluble and can have between about 0.05% and about 10%, and in certain embodiments between about 0.2% and about 10% by weight of the aqueous phase. Lower amounts of photo-initiator allow light to better penetrate the HIPE foam, which can provide for polymerization deeper into the HIPE foam. However, if polymerization is done in an oxygen-containing environment, there should be enough photo-initiator to initiate the polymerization and overcome oxygen inhibition. Photo-initiators can respond rapidly and efficiently to a light source with the production of radicals, cations, and other species that are capable of initiating a polymerization reaction. The photo-initiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photo-initiator is in the aqueous phase, suitable types of water-soluble photo-initiators include benzophenones, benzils, and thioxanthones. Examples of photo-initiators include 2,2'-Azobis[2-(2-imidazolin-2-yl)propane]

dihydrochloride; 2,2'-Azobis[2-(2-imidazolin-2-yl)propane] disulfate dehydrate; 2,2'-Azobis(1-imino-1-pyrrolidino-2-ethylpropane) dihydrochloride; 2,2'-Azobis[2-methyl-N-(2-hydroxyethyl)propionamide]; 2,2'-Azobis(2-methylpropionamidine) dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photo-initiators that can be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web or a portion of a web such as, for example, nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. In an embodiment, the enrobeable elements may be treated to be made hydrophobic. In an embodiment, the enrobeable elements may be treated to become hydrophilic.

The constituent fibers of the heterogeneous mass can be comprised of polymers such as polyethylene, polypropylene, polyester, and blends thereof. The fibers can be spunbond fibers. The fibers can be meltblown fibers. The fibers can comprise cellulose, rayon, cotton, or other natural materials or blends of polymer and natural materials. The fibers can also comprise a super absorbent material such as polyacrylate or any combination of suitable materials. The fibers can be monocomponent, bicomponent, and/or biconstituent, non-round (e.g., capillary channel fibers), and can have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers can range from about 0.1 denier to about 100 denier.

The heterogeneous mass can be comprised of more than one nonwoven precursor web. For example, the high internal phase emulsion is applied to the top surface of the first nonwoven web by means of an extrusion die in a horizontal configuration. A second nonwoven web can be applied to the top surface of the previously extruded high internal phase emulsion while in a horizontal configuration prior to the onset of solidification of the HIPE into a HIPE foam.

The above described structure creates a two nonwoven structure with HIPE foam in between the nonwovens and enrobed elements at the interface of HIPE foam and nonwoven, e.g. an absorbent stratum that is a heterogeneous mass comprising a first nonwoven having a first surface and a second surface and a second nonwoven. An open cell foam piece enrobes a portion of the first nonwoven and a portion of the second nonwoven. Alternatively, the second precursor web may be glued to the stratum heterogeneous mass after polymerization of the stratum.

It has been surprisingly found that by creating a heterogenous mass layer comprising open cell foam wherein at least a portion of one or more open cell foam pieces is in contact with a substrate or layer of enrobeable elements such as nonwoven fibers at both the top and bottom surface of the piece along a vertical axis allows for the heterogeneous mass to be submitted through a formation means while maintaining the fluid connectivity of the heterogeneous mass layer and without leaving a meaningful buildup or residue on the formation means.

In one aspect, known absorbent web materials in an as-made can be considered as being homogeneous throughout. Being homogeneous, the fluid handling properties of the absorbent web material are not location dependent, but are substantially uniform at any area of the web. Homogeneity can be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling and or mechanical properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability can be accomplished without a decrease in capillarity. Likewise the heterogeneous nature of the absorbent web may also enable discrete bending, compression or stretch zones within the web. The enabled discrete bending allows for improved flexibility without sacrificing capillarity.

In an embodiment, the heterogeneous mass may also include superabsorbent material that imbibe fluids and form hydrogels. These materials are typically capable of absorbing large quantities of body fluids and retaining them under moderate pressures and can be in either a fibrous, particulate or other physical form. The heterogeneous mass can include such materials dispersed in a suitable carrier such as cellulose fibers in the form of fluff or stiffened fibers or integrated within an AGM containing laminate.

The heterogeneous mass may include one or more types of fibers. Fibers included in the fibrous web may be thermoplastic particulates or fibers. The materials, and in particular thermoplastic fibers, can be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® Trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

The length of bicomponent fibers can vary depending upon the particular properties desired for the fibers and the web formation process. Typically, in an airlaid web, these thermoplastic fibers have a length from about 2 mm to about 12 mm long, preferably from about 2.5 mm to about 7.5 mm long, and most preferably from about 3.0 mm to about 6.0 mm long. The properties-of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine can have a decitex in the range from about 1.0 to about 20, preferably from about 1.4 to about 10, and most preferably from about 1.7 to about 7 decitex.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective thermally bonded fibrous matrix.

The heterogeneous mass can also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers can also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length can vary depending upon the particular properties desired for these fibers. Typically they have a length from about 0.3 to 7.5 cm, preferably from about 0.9 to about 1.5 cm. Suitable nonbonding thermoplastic fibers can have a decitex in the range of about 1.5 to about 35 decitex, more preferably from about 14 to about 20 decitex.

However structured, the total absorbent capacity of the absorbent core should be compatible with the design loading and the intended use of the mass. For example, when used in an absorbent article, the size and absorbent capacity of the heterogeneous mass may be varied to accommodate different uses such as incontinence pads, pantiliners, regular sanitary napkins, or overnight sanitary napkins.

The heterogeneous mass can also include other optional components sometimes used in absorbent webs. For example, a reinforcing scrim can be positioned within the respective layers, or between the respective layers, of the heterogeneous mass.

The heterogeneous mass comprising open-cell foam pieces produced from the present invention may be used as an absorbent core or a portion of an absorbent core in absorbent articles, such as feminine hygiene articles, for example pads, pantiliners, and tampons; wound dressing; disposable diapers; incontinence articles, for example pads, adult diapers; homecare articles, for example wipes, pads, towels; and beauty care articles, for example pads, wipes, and skin care articles, such as used for pore cleaning. The absorbent structure having a topsheet and/or a secondary topsheet integrated into a heterogeneous mass layer having open-cell foam pieces may be used in absorbent articles such as feminine hygiene articles, for example pads, pantiliners, and tampons; wound dressings; disposable diapers; incontinence articles, for example pads, adult diapers; homecare articles, for example wipes, pads, towels; and beauty care articles, for example pads, wipes, and skin care articles, such as used for pore cleaning. A diaper may be an absorbent article as disclosed in U.S. patent application Ser. No. 13/428,404, filed on Mar. 23, 2012.

The absorbent core structure may be used as an absorbent core for an absorbent article. In such an embodiment, the absorbent core can be relatively thin, less than about 5 mm in thickness, or less than about 3 mm, or less than about 1 mm in thickness. Cores having a thickness of greater than 5 mm are also contemplated herein. Thickness can be determined by measuring the thickness at the midpoint along the longitudinal centerline of the pad by any means known in the art for doing while under a uniform pressure of 0.25 psi. The absorbent core can comprise absorbent gelling materials (AGM), including AGM fibers, blood gelling agents (e.g. chitosan), quaternary salts or combinations thereof as is known in the art.

The heterogeneous mass layer may be formed or cut to a shape, the outer edges of which define a periphery.

In an embodiment, the heterogeneous mass may be used as a topsheet for an absorbent article. The heterogeneous mass may be combined with an absorbent core or may only be combined with a backsheet.

In an embodiment, the heterogeneous mass may be combined with any other type of absorbent layer or non-absorbent layer such as, for example, a layer of cellulose, a layer comprising superabsorbent gelling materials, a layer of absorbent airlaid fibers, a nonwoven layer, or a layer of absorbent foam, or combinations thereof. Other absorbent layers not listed are contemplated herein.

Formation means known for deforming a generally planar fibrous web into a three-dimensional structure are utilized in the present invention to modify as-made absorbent materials into absorbent materials having relatively higher permeability without a significant corresponding decrease in capillary pressure. Formation means may comprise a pair of intermeshing rolls, typically steel rolls having inter-engaging ridges or teeth and grooves. However, it is contemplated that other means for achieving formation can be utilized, such as the deforming roller and cord arrangement disclosed in US 2005/0140057 published Jun. 30, 2005. Therefore, all disclosure of a pair of rolls herein is considered equivalent to a roll and cord, and a claimed arrangement reciting two inter-meshing rolls is considered equivalent to an inter-meshing roll and cord where a cord functions as the ridges of a mating inter-engaging roll. In one embodiment, the pair of intermeshing rolls of the instant invention can be considered as equivalent to a roll and an inter-meshing element, wherein the inter-meshing element can be another roll, a cord, a plurality of cords, a belt, a pliable web, or straps. Likewise, other known formation technologies, such as creping, necking/consolidation, corrugating, embossing, button break, hot pin punching, and the like are believed to be able to produce absorbent materials having some degree of relatively higher permeability without a significant corresponding decrease in capillary pressure. Formation means utilizing rolls include "ring rolling", a "SELF" or "SELF'ing" process, in which SELF stands for Structural Elastic Like Film, as "micro-SELF", and "rotary knife aperturing" (RKA); as described in U.S. Pat. No. 7,935,207 Zhao et al., granted May 3, 2011. The formation means may be one of the formation means described in U.S. Pat. No. 7,682,686 (Curro et al.) granted on Mar. 23, 2010 or U.S. Pat. No. 7,648,752 (Hoying et al.) granted on Jan. 19, 2010. Suitable processes for constructing tufts are described in U.S. Pat. Nos. 7,172,801; 7,838,099; 7,754,050; 7,682,686; 7,410,683; 7,507,459; 7,553,532; 7,718,243; 7,648,752; 7,732,657; 7,789,994; 8,728,049; and 8,153,226. Formation means may also include Nested "SELF" as described below and in U.S. patent application Ser. No. 14/844,459 filed on Sep. 3, 2015. Formation means may also include hot pin, Selective Aperturing a Nonwoven (SAN) described in U.S. Pat. No. 5,628,097, 3D embossing and embossed stabilized formation as described in U.S. Patent Application No. 62/458,051 filed Feb. 13, 2017.

Referring to FIG. 1 there is shown in an apparatus and method for making web 1. The apparatus 100 comprises a pair of intermeshing rolls 174 and 176, each rotating about an axis A, the axes A being parallel in the same plane. Roll 174 comprises a plurality of ridges 172 and corresponding grooves 108 which extend unbroken about the entire circumference of roll 174. Roll 176 is similar to roll 174, but rather than having ridges that extend unbroken about the entire circumference, roll 176 comprises a plurality of rows of circumferentially-extending ridges that have been modified to be rows of circumferentially-spaced teeth 110 that extend in spaced relationship about at least a portion of roll 176. The individual rows of teeth 110 of roll 176 are separated by corresponding grooves 112. In operation, rolls 174 and 176 intermesh such that the ridges 172 of roll 174 extend into the grooves 112 of roll 176 and the teeth 110 of roll 176 extend into the grooves 108 of roll 174. The intermeshing is shown in greater detail in the cross sectional representation of FIG. 2, discussed below. Both or either of rolls 174 and 176 can be heated by means known in the art such as by using hot oil filled rollers or electrically-heated rollers.

In FIG. 1, the apparatus 100 is shown in a preferred configuration having one patterned roll, e.g., roll 176, and one non-patterned grooved roll 174. However, in certain embodiments it may be preferable to use two patterned rolls 176 having either the same or differing patterns, in the same or different corresponding regions of the respective rolls. Such an apparatus can produce webs with tufts 6 protruding from both sides of the web 1.

The method of making a web 1 in a commercially viable continuous process is depicted in FIG. 1. Web 1 is made by mechanically deforming precursor webs, such as first and second precursor webs, 180 and 21 that can each be described as generally planar and two dimensional prior to processing by the apparatus shown in FIG. 1. By "planar" and "two dimensional" is meant simply that the webs start the process in a generally flat condition relative to the finished web 1 that has distinct, out-of-plane, Z-direction three-dimensionality due to the formation of tufts 6. "Planar" and "two-dimensional" are not meant to imply any particular flatness, smoothness or dimensionality.

The process and apparatus of the present invention is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus and process of the present invention and the apparatus and process disclosed in the '801 patent, and the differences are apparent in the respective webs produced thereby. As described below, the teeth 110 of roll 176 have a specific geometry associated with the leading and trailing edges that permit the teeth to essentially "punch" through the precursor webs 180, 21 as opposed to, in essence, deforming the web. In a two layer laminate web 1 the teeth 110 urge fibers from precursor webs 180 and 21 out-of-plane by the teeth 110 pushing the fibers 8 through to form tufts 6. Therefore, a web 1 can have tufts 6 comprising loose fiber ends 18 and/or "tunnel-like" tufts 6 of looped, aligned fibers 8 extending away from the surface 13 of side 3, unlike the "tent-like" rib-like elements of SELF webs which each have continuous side walls associated therewith, i.e., a continuous "transition zone," and which do not exhibit interpenetration of one layer through another layer.

Precursor webs 180 and 21 are provided either directly from their respective web making processes or indirectly from supply rolls (neither shown) and moved in the machine direction to the nip 116 of counter-rotating intermeshing rolls 174 and 176. The precursor webs are preferably held in a sufficient web tension so as to enter the nip 16 in a generally flattened condition by means well known in the art of web handling. As each precursor web 180, 21 goes through the nip 116 the teeth 110 of roll 176 which are intermeshed with grooves 108 of roll 174 simultaneously urge portions of precursor webs 180 and 21 out of the plane to form tufts 6. In one embodiment, teeth 110 in effect "push" or "punch" fibers of first precursor web 180 through second precursor web 21. In another embodiment teeth 110 in effect "push" or "punch" fibers of both first and second precursor webs 180 and 21 out of plane to form tufts 6.

As the tip of teeth 110 push through first and second precursor webs 180, 21 the portions of the fibers of first precursor web 180 (and, in some embodiments, second precursor web 21) that are oriented predominantly in the CD across teeth 110 are urged by the teeth 110 out of the plane of first precursor web 180. Fibers can be urged out of plane due to fiber mobility, or they can be urged out of plane by being stretched and/or plastically deformed in the Z-direction. Portions of the precursor webs urged out of plane by teeth 110 results in formation of tufts 6 on first side 3 of web 1. Fibers of precursor webs 180 and 21 that are predominantly oriented generally parallel to the longitudinal axis L, i.e., in the MD, are simply spread apart by teeth 110 and remain substantially in their original, randomly-oriented condition.

It can be appreciated by the forgoing description that when web 1 is made by the apparatus and method of the present invention that the precursor webs 180, 21 can possess differing material properties with respect to the ability of the precursor webs to elongate before failure, e.g., failure due to tensile stresses. In one embodiment, a non-woven first precursor web 180 can have greater fiber mobility and/or greater fiber elongation characteristics relative to second precursor web 21, such that the fibers thereof can move or stretch sufficiently to form tufts 6 while the second precursor web 21 ruptures, i.e., does not stretch to the extent necessary to form tufts. In another embodiment, second precursor web 21 can have greater fiber mobility and/or greater fiber elongation characteristics relative to first precursor web 180, such that both first and second precursor webs 180 and 21 form tufts 6. In another embodiment, second precursor web 21 can have greater fiber mobility and/or greater fiber elongation characteristics relative to first precursor web 180, such that the fibers of second precursor web 21 can move or stretch sufficiently to form tufts 6 while the first precursor web 180 ruptures, i.e., does not stretch to the extent necessary to form tufts.

The degree to which the fibers of nonwoven precursor webs are able to extend out of plane without plastic deformation can depend upon the degree of inter-fiber bonding of the precursor web. For example, if the fibers of a nonwoven precursor web are only very loosely entangled to each other, they will be more able to slip by each other (i.e., to move relative to adjacent fibers by reptation) and therefore be more easily extended out of plane to form tufts. On the other hand, fibers of a nonwoven precursor web that are more strongly bonded, for example by high levels of thermal point bonding, hydroentanglement, or the like, will more likely require greater degrees of plastic deformation in extended out-of-plane tufts. Therefore, in one embodiment, one precursor web 180 or 21 can be a nonwoven web having relatively low inter-fiber bonding, and the other precursor web 180 or 21 can be a nonwoven web having relatively high inter-fiber bonding, such that the fibers of one precursor web can extend out of plane, while the fibers of the other precursor web cannot.

In one embodiment, for a given maximum strain (e.g., the strain imposed by teeth 110 of apparatus 100), it is beneficial that second precursor web 21 actually fail under the tensile loading produced by the imposed strain. That is, for the tufts 6 comprising only, or primarily, fibers from first precursor web 180 to be disposed on the first side 3 of web 1, second precursor web 21 must have sufficiently low fiber mobility (if any) and/or relatively low elongation-to-break such that it locally (i.e., in the area of strain) fails in tension, thereby producing openings 4 through which tufts 6 can extend. In another embodiment it is beneficial that second precursor web 21 deform or stretch in the region of induced strain, and does not fail, such that tuft 6 includes portions of second precursor web 21.

In one embodiment second precursor web 21 has an elongation to break in the range of 1%-5%. While the actual required elongation to break depends on the strain to be induced to form web. 1, it is recognized that for most embodiments, second precursor web 21 can exhibit a web elongation-to-break of 6%, 7%, 8%, 9%, 10%, or more. It is also recognized that actual elongation-to-break can depend on the strain rate, which, for the apparatus shown in FIG. 1 is a function of line speed. Elongation to break of webs used in the present invention can be measured by means known in the art, such as by standard tensile testing methods using standard tensile testing apparatuses, such as those manufactured by Instron, MTS, Thwing-Albert, and the like.

Relative to first precursor web 180, second precursor web 21 can have lower fiber mobility (if any) and/or lower elongation-to-break (i.e., elongation-to-break of individual fibers, or, if a film, elongation-to-break of the film) such that, rather than extending out-of-plane to the extent of the tufts 6, second precursor web 21 fails in tension under the strain produced by the formation of tufts 6, e.g., by the teeth 110 of apparatus 100. In one embodiment, second precursor web 21 exhibits sufficiently low elongation-to-break relative to first precursor web 180 such that flaps 7 of opening 4 only extend slightly out-of-plane, if at all, relative to tufts 6. In general, for embodiments in which tufts 6 comprise primarily fibers from first precursor web 180, it is believed that second precursor web 21 should have an elongation to break of at least 10% less than the first precursor web 180, preferably at least 30% less, more preferably at least 50% less, and even more preferably at least about 100% less than that of first precursor web 180. Relative elongation to break values of webs used in the present invention can be measured by means known in the art, such as by standard tensile testing methods using standard tensile testing apparatuses, such as those manufactured by Instron, MTS, Thwing-Albert, and the like.

In one embodiment second precursor web 21 can comprise substantially all MD-oriented fibers, e.g., tow fibers, such that there are substantially no fibers oriented in the CD. For such an embodiment of web 1 the fibers of second precursor web 21 can simply separate at the opening 4 through which tufts 6 extend. In this embodiment, therefore, second precursor web 21 need not have any minimum elongation to break, since failure or rupture of the material is not the mode of forming opening 4.

The number, spacing, and size of tufts 6 can be varied by changing the number, spacing, and size of teeth 110 and making corresponding dimensional changes as necessary to roll 176 and/or roll 174. This variation, together with the variation possible in precursor webs 180, 21 permits many varied webs 1 having varied fluid handling properties for use in a disposable absorbent article. As described more fully below, a web 1 comprising a nonwoven/film first precursor web/second precursor web combination can also be used as a component in disposable absorbent articles. However, even better results are obtained in a nonwoven/nonwoven precursor web/second precursor web combination wherein fibers from both webs contribute to tufts 6.

Nested "SELF" relates to a method that includes making a fibrous materials by a method comprising the steps of: a) providing at least one precursor nonwoven web; b) providing an apparatus comprising a pair of forming members comprising a first forming member (a "male" forming member) and a second forming member (a "female" forming member); and c) placing the precursor nonwoven web(s) between the forming members and mechanically deforming the precursor nonwoven web(s) with the forming members. The forming members have a machine direction (MD) orientation and a cross-machine direction (CD) orientation.

Figure 2:
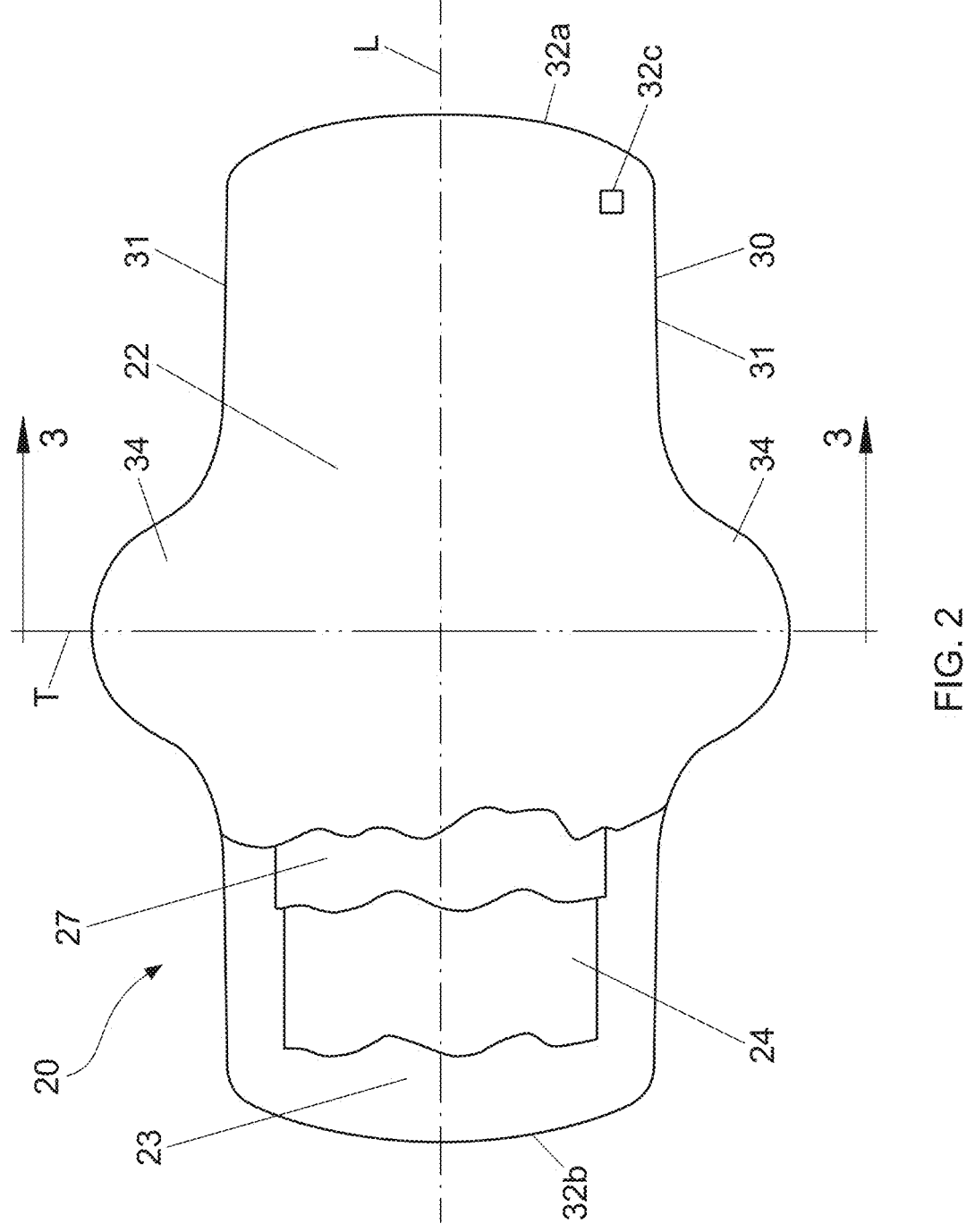
FIG. 2 is a top view of an absorbent article.

FIG. 2 is a plain view of the sanitary napkin 20 of the present invention in its planar state with portions of the structure being cut-away to more clearly show the construction of the sanitary napkin 20 and with the portion of the sanitary napkin 20 which faces or contacts the wearer, oriented towards the viewer. As shown in FIG. 2, the sanitary napkin 20 preferably comprises a liquid pervious topsheet 22, a liquid impervious backsheet 23 joined with the topsheet 22, an absorbent core 24 positioned between the topsheet 22 and the backsheet 23.

The sanitary napkin 20 has two surfaces, a body-contacting surface or "body surface" 20 a and a garment surface 20b. The body contacting surface 20a is intended to be worn adjacent to the body of the wearer while the garment surface 20b is on the opposite side and is intended to be placed adjacent to the wearer's undergarments when the sanitary napkin 20 is worn. The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies in the plane of the sanitary napkin 20 that is generally perpendicular to the longitudinal direction.

A sanitary napkin 20 can have any shape known in the art for feminine hygiene articles, including symmetric shapes, as well as pear shapes, bicycle-seat shapes, trapezoidal shapes, wedge shapes, other shapes that have one end wider than the other, or any other symmetric or assymetric shape that is symmetric or assymetric along a longitudinal or a transverse axis. Sanitary napkins and pantyliners can also be provided with lateral extensions known in the art as "flaps" or "wings". Such extensions can serve a number of purposes, including, but not limited to, protecting the wearer's panties from soiling and keeping the sanitary napkin secured in place.

FIG. 2 also shows that the sanitary napkin 20 has a periphery 30, which is defined by the outer edges of the sanitary napkin 20 in which the longitudinal edges are designated 31 and the end edges are designated 32, the front edge being 32a and the back edge being 32b. An indicia 32c is located on the body surface 20a in the area anywhere from the front edge to one-fourth of the length of the article away from the front edge. The indicia 32c is any type of marking or designation (i.e. any small shape or design allows the wearer to know which end edge is the front edge so that they can properly position the article initially and properly wear the article.

While the topsheet, the backsheet, and the absorbent core may be assembled in a variety of well known configurations (including so called "tube" products or side flap products), preferred sanitary napkin configurations are described generally in U.S. Pat. No. 4,950,264, "Thin, Flexible Sanitary Napkin," Osborn, issued on Aug. 21, 1990; U.S. Pat. No. 4,425,130, "Compound Sanitary Napkin," DesMarais, issued on Jan. 10, 1984; U.S. Pat. No. 4,321,924, "Bordered Disposable Absorbent Article," Ahr, issued on Mar. 30, 1982; U.S. Pat. No. 4,589,876, "Shaped Sanitary Napkin With Flaps", Van Tilburg, issued on Aug. 18, 1987. Each of these patents are incorporated herein by reference.

FIG. 2 shows a preferred embodiment of the sanitary napkin 20 in which the topsheet 22 and the backsheet 23 have length and width dimensions generally larger than those of the absorbent core 24. The topsheet 22 and the backsheet 23 extend beyond the edges of the absorbent core 24 to thereby form not only portions of the periphery but also side flaps or wings 34.

Figure 3:
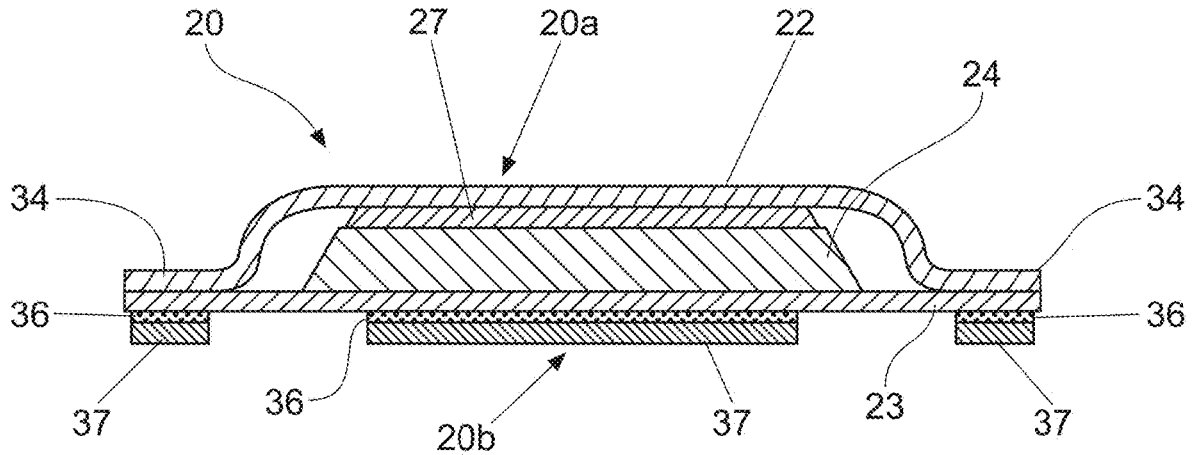
FIG. 3 is a cross section of FIG. 2 along 2-2.

FIG. 3 is a cross-sectional view of the sanitary napkin 20 taken along section line 2-2 of FIG. 2. FIG. 3 shows the secondary topsheet 27, just below the topsheet 22. The wing 34 is an extension of the topsheet 22. The fastening means 36 together with the release liner 37 maintains the article in place so that it can perform its intended function.

The upper side of a sanitary napkin generally has a liquid pervious topsheet 22. The lower side generally has a liquid impervious backsheet 23 that is joined with the topsheet 22 at the edges of the product. An absorbent core 24 is positioned between the topsheet 22 and the backsheet 23. A secondary topsheet may be provided at the top of the absorbent core 24, beneath the topsheet.

The topsheet 22, the backsheet 23, and the absorbent core 24 can be assembled in a variety of well-known configurations, including so called "tube" products or side flap products, such as, for example, configurations are described generally in U.S. Pat. No. 4,950,264, "Thin, Flexible Sanitary Napkin" issued to Osborn on Aug. 21, 1990, U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, and "Shaped Sanitary Napkin With Flaps" issued to Van Tilburg on Aug. 18, 1987. Each of these patents is incorporated herein by reference.

The backsheet 23 and the topsheet 22 can be secured together in a variety of ways. Adhesives manufactured by H. B. Fuller Company of St. Paul, Minn. under the designation HL-1258 or H-2031 have been found to be satisfactory. Alternatively, the topsheet 22 and the backsheet 23 can be joined to each other by heat bonding, pressure bonding, ultrasonic bonding, dynamic mechanical bonding, or a crimp seal.

As is typical for sanitary napkins and the like, the sanitary napkin 20 of the present invention can have panty-fastening adhesive disposed on the garment-facing side of backsheet 23. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the wearer's panties.

The backsheet may be used to prevent the fluids absorbed and contained in the absorbent structure from wetting materials that contact the absorbent article such as underpants, pants, pajamas, undergarments, and shirts or jackets, thereby acting as a boundary to fluid transport. The backsheet according to an embodiment of the present invention can also allow the transfer of at least water vapour, or both water vapour and air through it.

Especially when the absorbent article finds utility as a sanitary napkin or panty liner, the absorbent article can be also provided with a panty fastening means, which provides means to attach the article to an undergarment, for example a panty fastening adhesive on the garment facing surface of the backsheet. Wings or side flaps meant to fold around the crotch edge of an undergarment can be also provided on the side edges of the napkin.

It has been surprisingly found that by processing a heterogeneous mass layer through a formation means, either by itself, with another layer (such as a topsheet or a secondary topsheet), or in a sandwich structure results in an absorbent structure that is made or creates different zones that exhibit different compression forces and bending patterns and/or bending points. Further, by selecting specific patterns, it has been found that one may create an absorbent article that has different properties in the front versus the central portion or versus the back portion. This allows one to create a product that behaves differently in each of the front region, the central region, and the back region. Additionally, each of the front region, the back region, and the central region may have more than one zone, each zone having a different pattern resulting in different mechanical and absorbent properties (such as, for example, compression forces, absorption rates, and bending points).

Additionally, due to the use of formation means on a heterogenous mass layer, the absorbent structure may exhibit improved flexibility due to the creation of bending points in the absorbent structure. The result is an absorbent structure that may maintain its intended shape while in use when compared to traditional absorbent structures that become stiffer due to welding, glues, embossing, or when they improve capillarity through densification. Additionally, because the heterogeneous mass layer may be integrated with a topsheet during the formation means, the integrated absorbent structure may serve as the topsheet of the absorbent product.

The integrated topsheet and/or secondary topsheet with the heterogeneous mass may deliver unique patterns that enable shaping dynamically without loss of structural integrity. The unique patterns may be leveraged such that they selectively deform some of the web enabling multiple bending modes for conforming to complex bodily shapes without meaningful degradation of the structural integrity of the absorbent product. Further, by designing the bending points in the absorbent product using formation means, one may create a product that has a better fit. The better fit is exemplified when the product is placed in contact with the spacing in the gluteal groove. Further, by enabling the product to have three dimensional topography, the absorbent product may bend and stretch to complex shapes and various surface topographies to be closer to the body of the user. Bending may be different for different sections.

Said otherwise, it has been found that by utilizing a non-woven/foam (NW-foam) composite or a NW-foam-NW composite one may create a product that has the ability to resist high tensile forces. The fibrous nature of the NW effectively blunts any crack growth or propagation making the core much more robust in active product use situations walking, running, biking etc.

Along with the added benefit of significantly enhanced product integrity, absorbent structures utilizing a heterogeneous mass layer are highly directional in relation to their structural properties which provides product designers material which can be strategically implemented in a product form to simultaneously achieve optimal absorbency, comfort and fit related performance. These absorbent structures can have wide ranging MD to CD bending rigidity ratios that range from as low as 2:1 to as high as 20:1, such as, for example 3:1, 4:1, 5:1, 6:1, 7:1, 8:1, 9:1, 10:1, 11:1, 12:1, 13:1, 14:1, 15:1, 16:1, 17:1, 18:1, or 19:1.

Additionally, one may modify the directional nature of these absorbent cores and products using one or more of the following methods without losing fluid continuity within the absorbent core or the absorbent layer which include but are not limited to: 1. Strategically orienting pieces of foam composite cores (single NW or NW-foam-NW sandwich) such that stiffness and flexibility are optimally oriented to deliver the desired fit model; 2. Mechanically deforming and altering the structural stiffness of the NW-foam-NW, composite core sandwich or the composite core such that absorbent material is not removed but creates a discontinuity in structural properties. Such processes are referred to as formation means and are described above; 3. fluid etching the core structure with a high pressure stream of water that can create macro or microscopic features in the composite core; and 4. selectively removing portions of the core composite without creating holes through all the layers of the core composite at the point of removal. The high pressure impingement of the absorbent core composite in fluid etching can be modulated to vary the depth of the cut or penetration into the sandwiched foam core.

In the context of a final product, these processes can be used individually or in combination to create zonal properties within the product, the product core, a layer of the product core, a plurality of layers in the product core to create a product that yields enhanced comfort, fit and/or absorbency. These zonal properties may be created without a break in fluid distribution continuity in the absorbent core or core layer thereby allowing fluid to be wicked along the vertical axes, the longitudinal axes, and/or the transverse axes of the absorbent core or absorbent core layer. For example, a pattern within a zone may partially remove aspects of the core along the vertical axis provided that the pattern does not create a hole that runs along the entire vertical axis creating a complete lack of material in the removed area. Said otherwise, if the pattern is held up to the light, one should be able to see elements of the absorbent layer such as the nonwoven or the absorbent material throughout the layer along any longitudinal and any transverse axis.

Additionally, the absorbent structure may provide a higher capillarity work potential gradient to draw fluid away from topsheet and into the core compared to traditional absorbent articles, such as, for example, from 100 mJ/m$^2$ to 80,000 mJ/m$^2$ within 0.5 mm, or 0.25 mm, or within 0.15 mm rather than current topsheets which have a gradient of 100 mJ/m$^2$ to 1,000 mJ/m$^2$ over about 2 mm, or about 1.5 mm, or about 1 mm of distance. The absorbent core structure may exhibit a capillary cascade of between, for example, 100 mJ/m$^2$ to 80,000 mJ/m$^2$ within 0.5 mm; 1,000 mJ/m$^2$ to 70,000 mJ/m$^2$ within 0.5 mm; 3,000 mJ/m$^2$ to 70,000 mJ/m$^2$ within 0.5 mm; 5,000 mJ/m$^2$ to 60,000 mJ/m$^2$ within 0.5 mm; 10,000 mJ/m$^2$ to 50,000 mJ/m$^2$ within 0.5 mm; 20.000 mJ/m$^2$ to 40,000 mJ/m$^2$ within 0.5 mm; 100 mJ/m$^2$ to 80,000 mJ/m$^2$ within 0.25 mm; 1,000 mJ/m$^2$ to 70,000 mJ/m$^2$ within 0.25 mm; 3,000 mJ/m$^2$ to 70,000 mJ/m$^2$ within 0.25 mm; 5,000 mJ/m$^2$ to 60,000 mJ/m$^2$ within 0.25 mm; 10,000 mJ/m$^2$ to 50,000 mJ/m$^2$ within 0.25 mm; 20.000 mJ/m$^2$ to 40,000 mJ/m$^2$ within 0.25 mm; 100 mJ/m$^2$ to 80,000 mJ/m$^2$ within 0.15 mm; 1,000 mJ/m$^2$ to 70,000 mJ/m$^2$ within 0.15 mm; 3,000 mJ/m$^2$ to 70,000 mJ/m$^2$ within 0.15 mm; 5,000 mJ/m$^2$ to 60,000 mJ/m$^2$ within 0.15 mm; 10,000 mJ/m$^2$ to 50,000 mJ/m$^2$ within 0.15 mm; or 20.000 mJ/m$^2$ to 40,000 mJ/m$^2$ within 0.15 mm.

Capillarity cascade relates to the change in capillarity as one moves along an axis of the absorbent structure. Additionally, the wells allow for the absorbent structure to exhibit a capillary cascade along not only the vertical plane but also along the X-Y plane. Unlike other structures that may exhibit different capillarity profiles in the vertical direction versus within a plane, the absorbent structure having an integrated topsheet with a heterogeneous mass layer comprising wells creates a structure where the capillarity cascade is present within a plane. This is due to the integration of the groups of fibers from the topsheet through the heterogeneous mass.

Bunched compression may be used to measure the flexibility of a zone. The bunched compression method is a multi-axis bending test that is executed on product or core samples. When formation means is executed on a traditional layered core or a foam layer, in-use properties rapidly degrade or create product/core integrity issues. The ratio of the peak force to wet recovery energy communicates the balance between flexibility and shape stability of the product. The lower the peak force the more flexibility the product/material has when bending and conforming to her complex shape.

The absorbent structure may be deformed in the z direction with low compressive force while nevertheless preserving simultaneous the ability to conform and flow with complex bodily movements.

Additionally, due to the choice in deformation and in materials, one may create an absorbent article that exhibits a vertical gradient in the core system or in the core system integrated with the topsheet. The vertical gradient is maintained during usage and even when the product is saturated.

As discussed above, the topsheet and/or secondary topsheet integrated with a heterogeneous mass having a high capillarity absorbent has been found to impart curved, stretchable contours that can flow with the body without significant force to deform while not displacing her tissues aggressively. Further, the absorbent structure lacks strong densification, sharp tears, or shredding as seen with traditional cellulose based materials. Strong densification, sharp tears, and shredding may provide sharp contour which lead to a reduction in comfort and tactile softness. This property is exhibited using the Z-compressibility and the BC/Kawabata test methods.

Increased product flexibility may directly lead to improved comfort by the user. Increased flexibility allows for the product to follow the topography of the user's body and thereby may create better contact between the article and the body. Further, improved flexibility leads to a better usage experience because the product behaves more like a garment and may follow the contours of the body through dynamic motions. Another vector that improves overall comfort for the user is the level of cushion that the absorbent article may provide. Due to the direct contact with the body, increasing the cushion of the product and removing any rough surfaces leads to an improved tactile feel and comfort for the user.

A dynamic flexibility range and sustained product shape is given to the product by the specified ratio of peak to wet recovery of less than 150 gf/N*mm and greater than 30 gf/N*mm, such as, for example 40, 50, 60, 70, 80, 90, 100, 110, 120, 130, 140, or 145 gf/N*mm Conformance is also communicated to the user thru initial interaction with the pad the "cushiness" in caliper, stiffness and resiliency properties of the absorbent product in the thru thickness direction. In market products have demonstrated a consumer desirable stiffness gradient that signals a premium quality softness and product conformance in the product thru thickness direction. The quilted and/or pillowy nature of particular formation means patterns with the desirable stiffness gradient provide simultaneously a ZD direction cushiness that is desirable as well as active body cleaning locations that enhance the comfort experience in a way that the topography of traditional in market core systems cannot.

Figure 4:
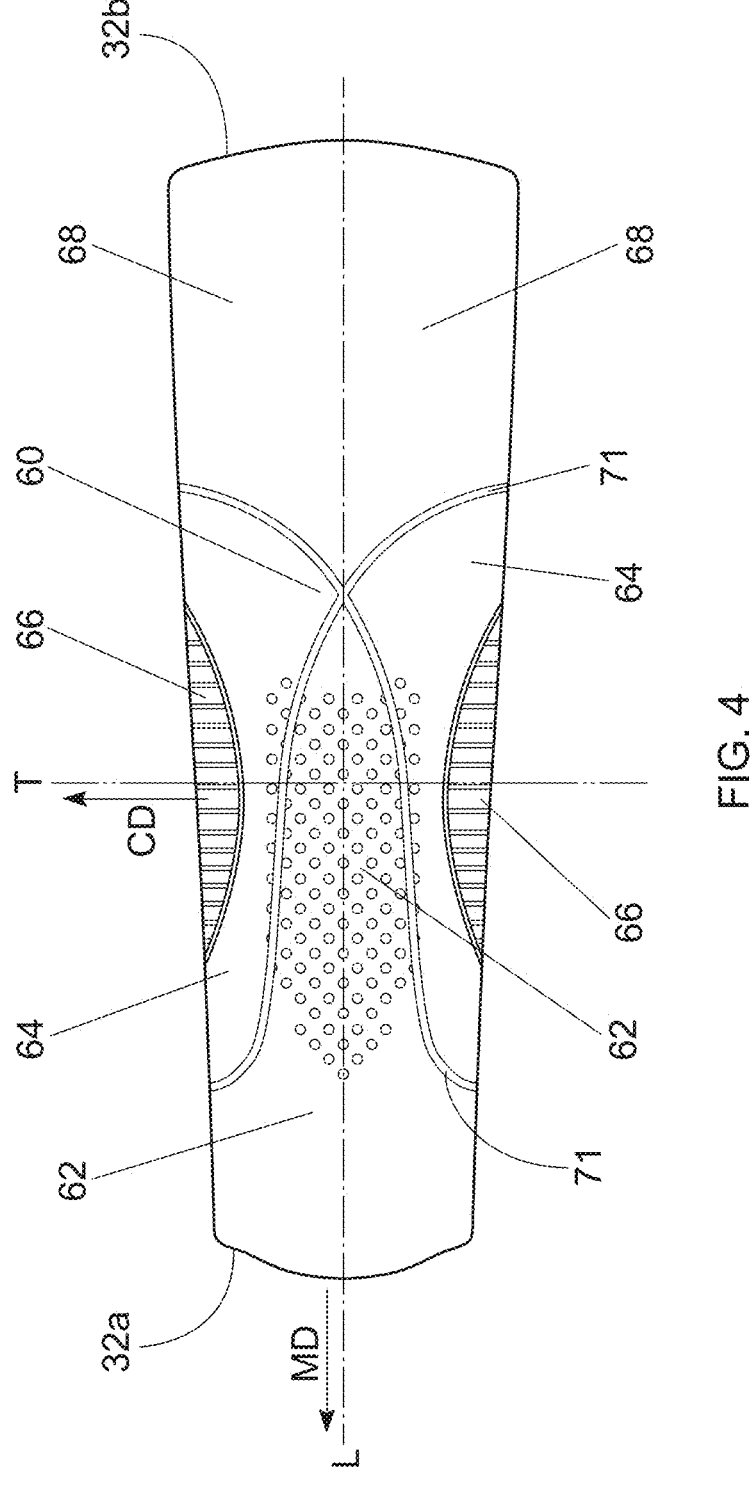
FIG. 4 represents a top view of an absorbent article.

As described above and shown in FIG. 4, on can create an absorbent article having a plurality of zones, each zone having different mechanical and fluid handling properties. As shown in FIG. 4, the article may comprise five zones separated by visual boundaries 71. The visual boundary may create a break in fluid continuity in the absorbent structure or absorbent layer or may not create a break in fluid continuity in the absorbent structure or absorbent layer. The article of FIG. 4 has a front edge or leading edge 32a, a back edge 32b, a first zone 1 identified as 62, a zone 2 identified as 64, a third zone identified as 66, a fourth zone identified as 68, and a boundary convergence area 60.

As shown in the figure, the zones may be irregularly shaped. Alternatively, the zones may be shaped according to standard geometric figures such as, for example, squares, circles, and triangles. Each zone may serve a different intended purpose. For example, zone 1 may exhibit a higher suction or capillarity than one or more of the other zones to capture fluid and too keep fluid from the body. Additionally, zone 1 may serve as a stiffer stability zone that maintains the product in contact with the body. Zones 2 and 3 may be designed to have more, less or the same amount of suction or capillarity than zone 1. Zones 2 and 3 may be further be designed to allow for bending along to the edges of the absorbent article; thereby allowing the pad to follow more complex geometries at the point of contact with the vaginal canal outside of the zone 1 stability zone. Zone 2 and 3 allow for increased mobility and wrapping of the article around the undergarment of the user. Zone 4 allows for increased movement in the high motion portion of the article which contacts the gluteal groove.

Figure 5A:
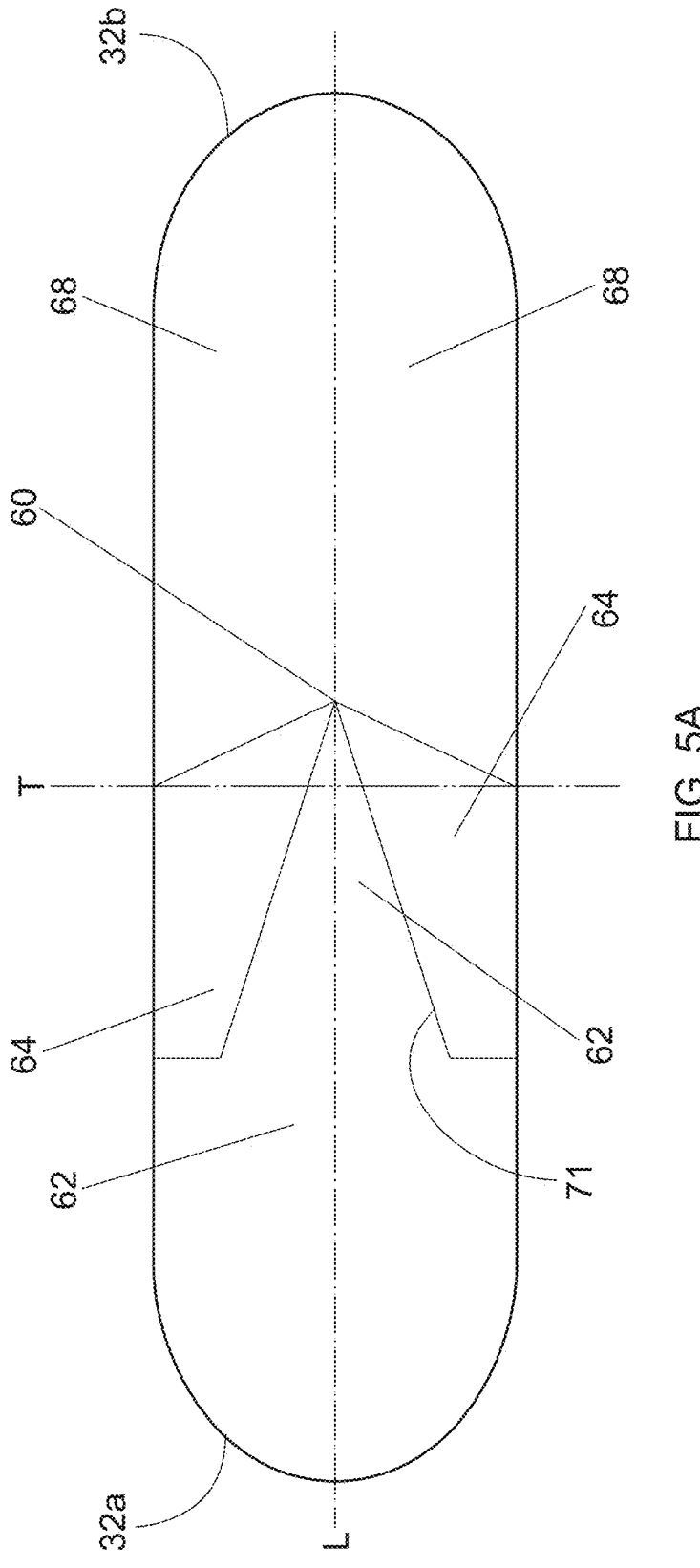
FIG. 5A-H represents examples of the potential absorbent article.
Figure 5B:
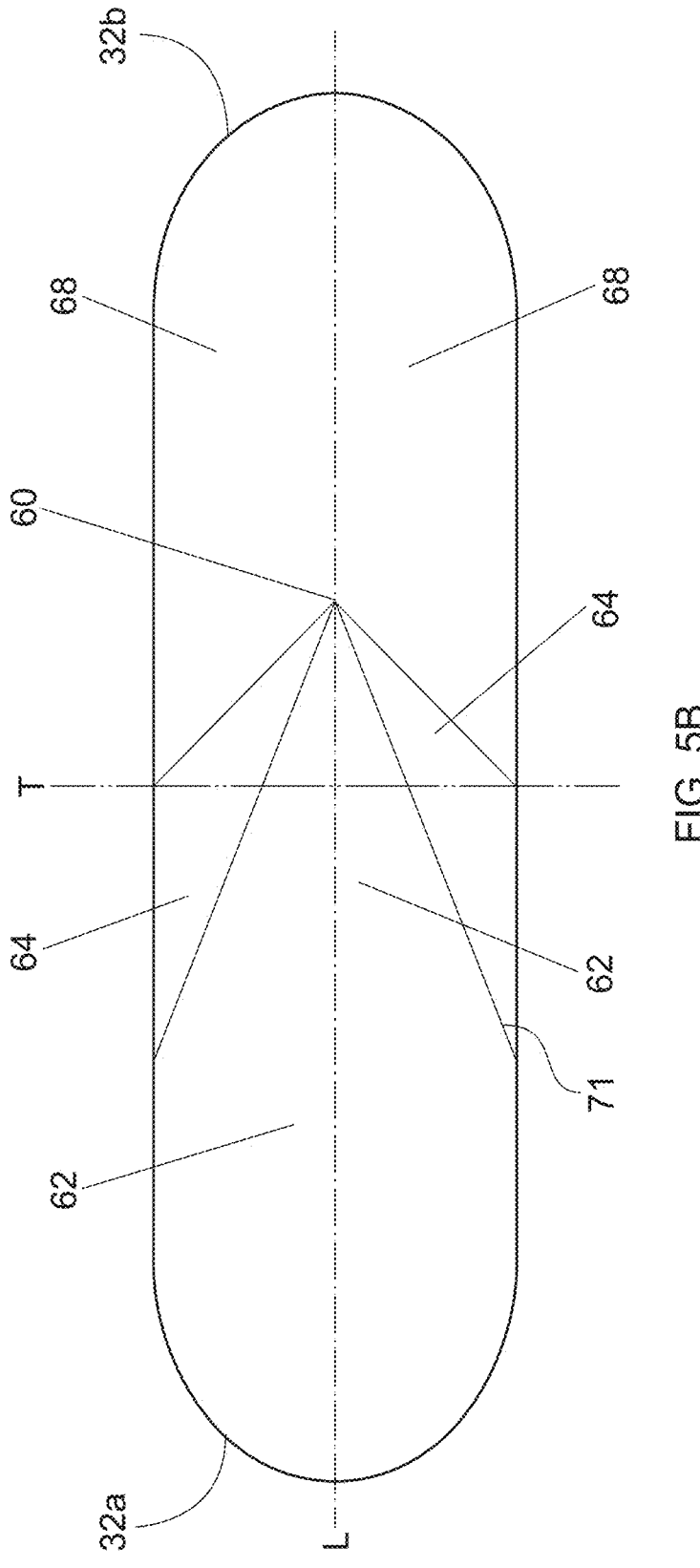
Figure 5C:
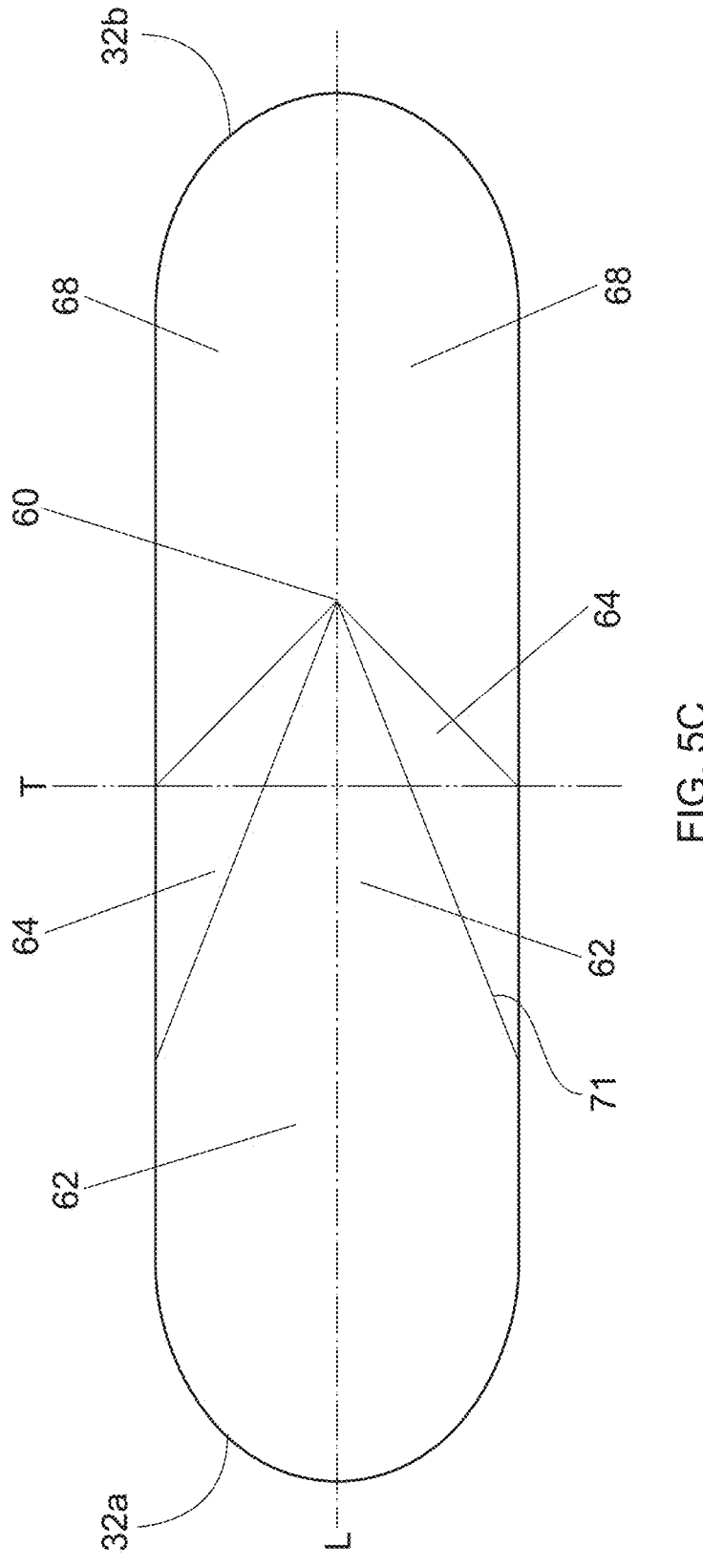
Figure 5D:
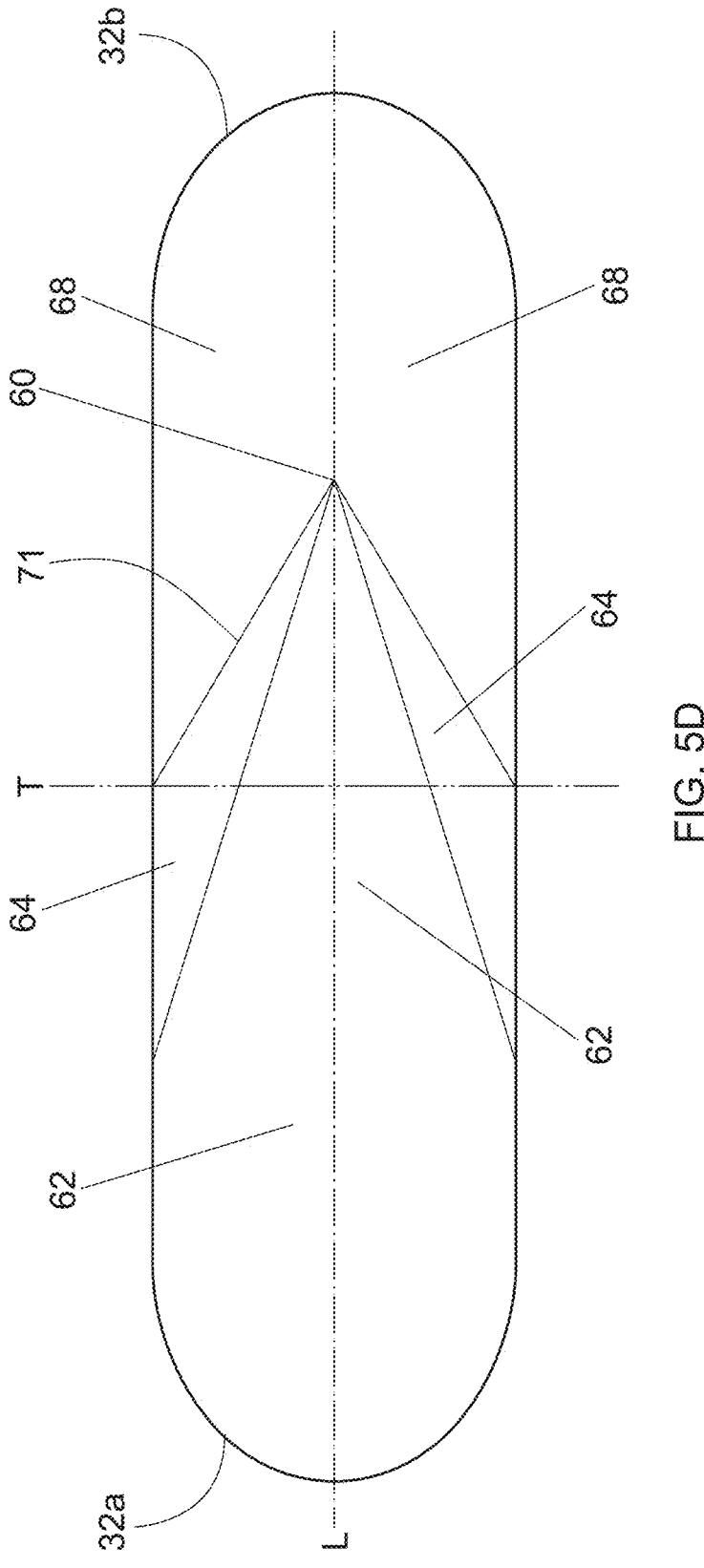
Figure 5E:
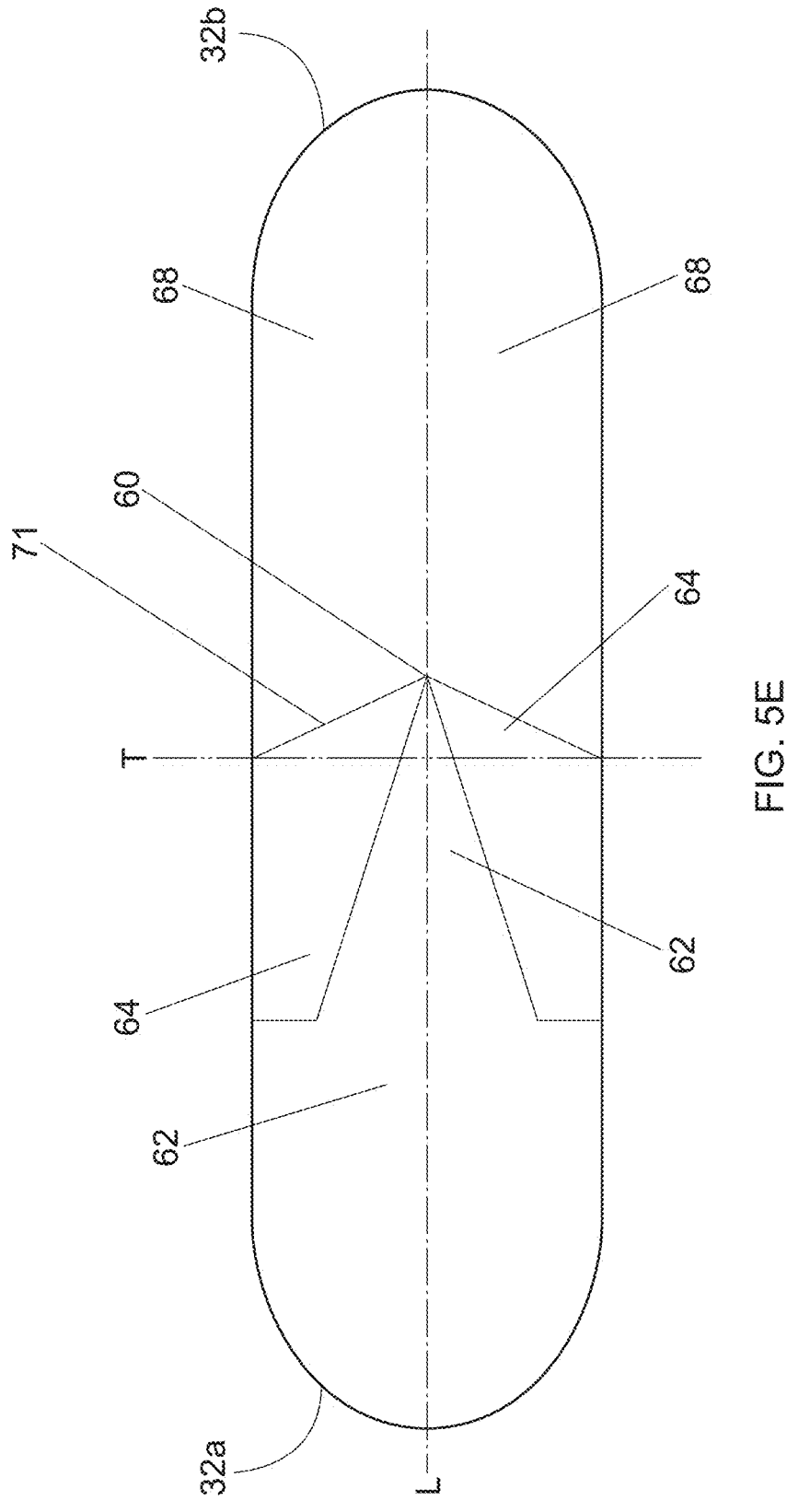
Figure 5F:
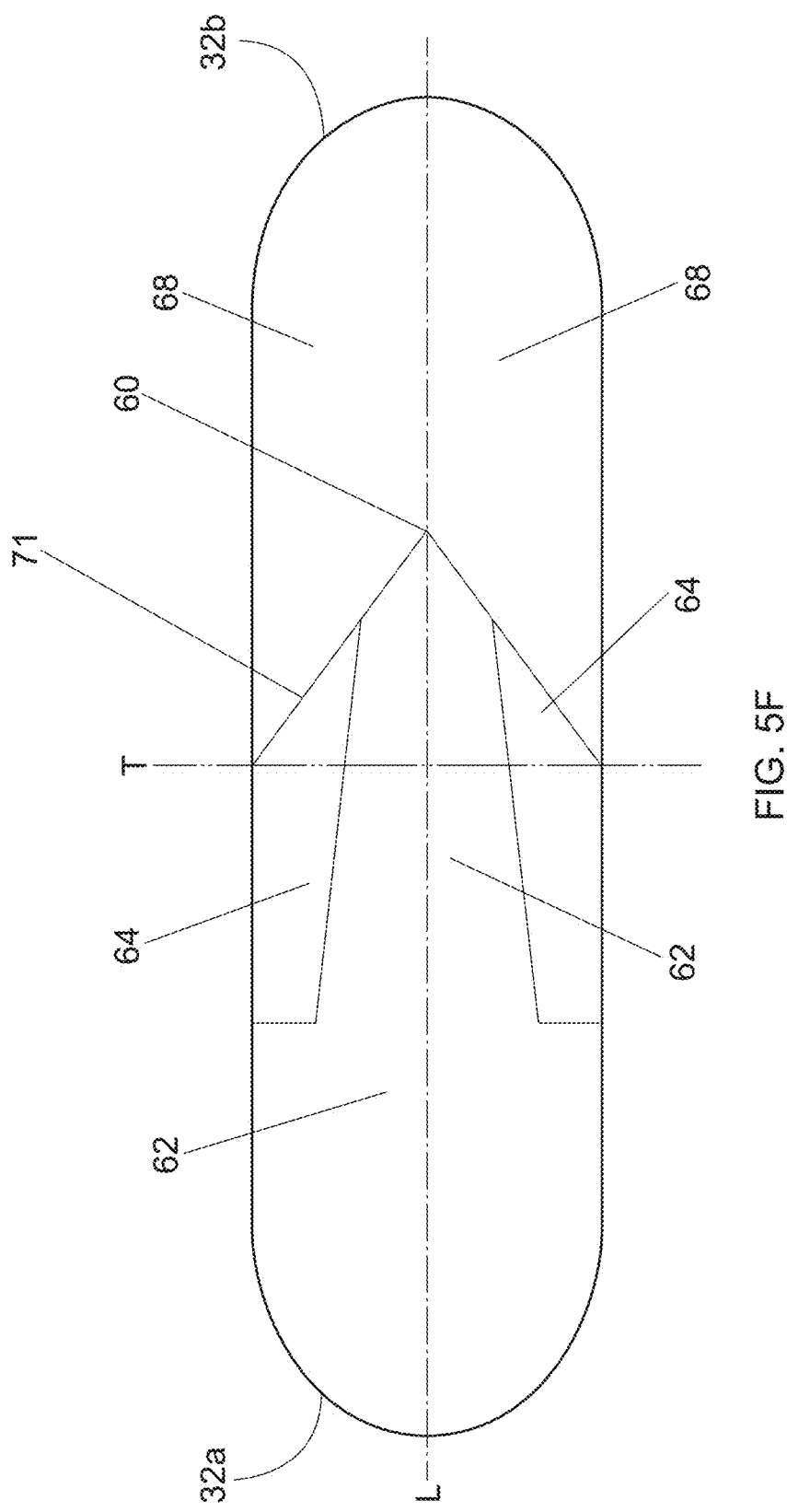

Additionally referring to FIG. 4, Zone 1 (62) may serve as a stiffer stability zone that may maintain the product in contact with the body may also serve as the zone responsible for capturing a substantial portion of the fluid as it exits the body. As such it may also be desirable to ensure this zone is more open or permeable to fluids such that it allows for fluid to rapidly enter this stiffer stability zone. At the same time due to Zone 1 (62) central stability this make it more difficult to compress and expel the fluid out as rewetting under bodily movements. It may also be desirable to impart a variation or gradient in the fluid absorption properties across zone for any other zone in either a MD or CD or both MD and CD direction to take into account the different physical or anatomical bodily features the zone may come in contact with or as a response to the relative motion of the product to the body. For example, in Zone 1 (62) at the leading edge (32*a*) of the product may come into contract with pubic hairs that may hinder accessibility of the absorbent article to the fluid. In this case Zone 1 (62) may have an open permeable fluid property in the area closest to the central vaginal opening, while towards the leading edge (32*a*) of Zone 1 may have a more textured, fibrous or complex surface topography that can mingle with pubic hairs combined with higher suction to better clean and compete for fluid on or below pubic hairs. Alternatively to Zone 1 in FIG. 4, it may be desirable that Zone 2 (64) serve the purpose of not only allowing the pad to follow more complex anatomical geometries around the Zone 1 (62) stability zone, but to also hinder surface fluid moving towards Zone 3 (66), via surface flow or run-off so as to maintain a consumer preferred cleaner appearance in the Zone 3 (66) areas of the product. Zone 2 (64) may exhibit the need to conform to more complex body features and this may lead to surfaces that are angled more steeply leading to a higher risk of surface fluid run-off. It may be desirable to impart a suitable surface texture to this Zone 2 (64) region together with a higher capillarity suction, within the surface texture or below, so as to hinder fluid run-off while conforming to these complex anatomical geometries. Zone 3 (66) in FIG. 4 is a zone that comes into contact with the legs and specifically the inner thighs during bodily motion. It is desirable that Zone 3 is not only comfortable to the touch but also maintains a cleaner after use appearance, ideally a clean white appearance, at this critical leakage prone perimeter (66). While it may be most desirable to limit fluid absorption or storage in Zone 3 (66), it nevertheless serves as a final zone of absorbency should fluid manage to move beyond Zones 1 (62) or Zone 2 (64) or is able to bypass the product or move, under gravity, along the body. It is therefore desirable that Zone 3 (66) has a good combination of capillarity suction with the ability to pull fluid deep thus preserving a cleaner edge appearance. Since this part of the product experiences high bodily motion, imparting, a surface topography suitable for wiping the body and that is able to clean the body leveraging a wiping mechanism combined with the capillarity suctions to pull fluid deep may be desirable. In some cases, referring to FIG. 5A it may be desirable to provide the absorbent article with an alternative zonal pattern in which features of the perimeter element 66 is combined together within the zonal element of Zone 2 (64). In this case fluid absorption properties across FIG. 5A Zone 2 (64) may be a combination of the fluid properties specified for Zone 2 and Zone 3 detailed in FIG. 4. Referring back to FIG. 4, Zone 4 (68) has an important role to play in capturing fluid that may be running either along the buttocks or within the gluteal grove. As such it may be desirable to have surface features, topographies and absorbent properties that minimize fluid surface run-off while being able to rapidly absorb fluid travelling on the body facing surface or the body via a balance of both capillarity suction and permeability. At the same time this Zone 4 (68) features high compressive forces that can lead to fluid rewetting the surface so maintaining secure fluid storage within the absorbent system, away from the product surface is desirable.

In addition, the use of boundaries between zones that do not lose fluid continuity within an absorbent core or core layer allows fluid to travel or wick between zones while maintaining the desired bending moments and flexibility. This may be done by using fluid etching to create the boundaries, thereby leaving absorbent material (foam) in the boundaries. The boundaries may be created by using formation means and controlling the depth of penetration to minimize densification while changing the fluid absorbency properties of the boundary when compared to the adjacent zones. The two or more zones may be separated by a boundary. The boundary may be a topographical boundary, a mechanical boundary, a visual boundary, a fluid handling property boundary, or a combination thereof. The boundary property may be distinct from the two zones adjacent to the boundary. The absorbent structure may have a perimeter boundary that exhibits a different property than the one or more adjacent zones to the boundary.

As shown in the figure the boundaries isolate Zone 1 or the zone responsible for capturing a substantial portion of the fluid. The boundary pattern creates a boundary convergence area in the latter half of the article. The boundary pattern separates each side of the core in front of the boundary convergence area. The back is separated from the middle portion and front portion by the boundary. As shown in the figure, zone 4 may be divided into two zones 4a and 4b. The added boundary between zone 4a and 4b allows for increased flexibility.

Figure 5G:
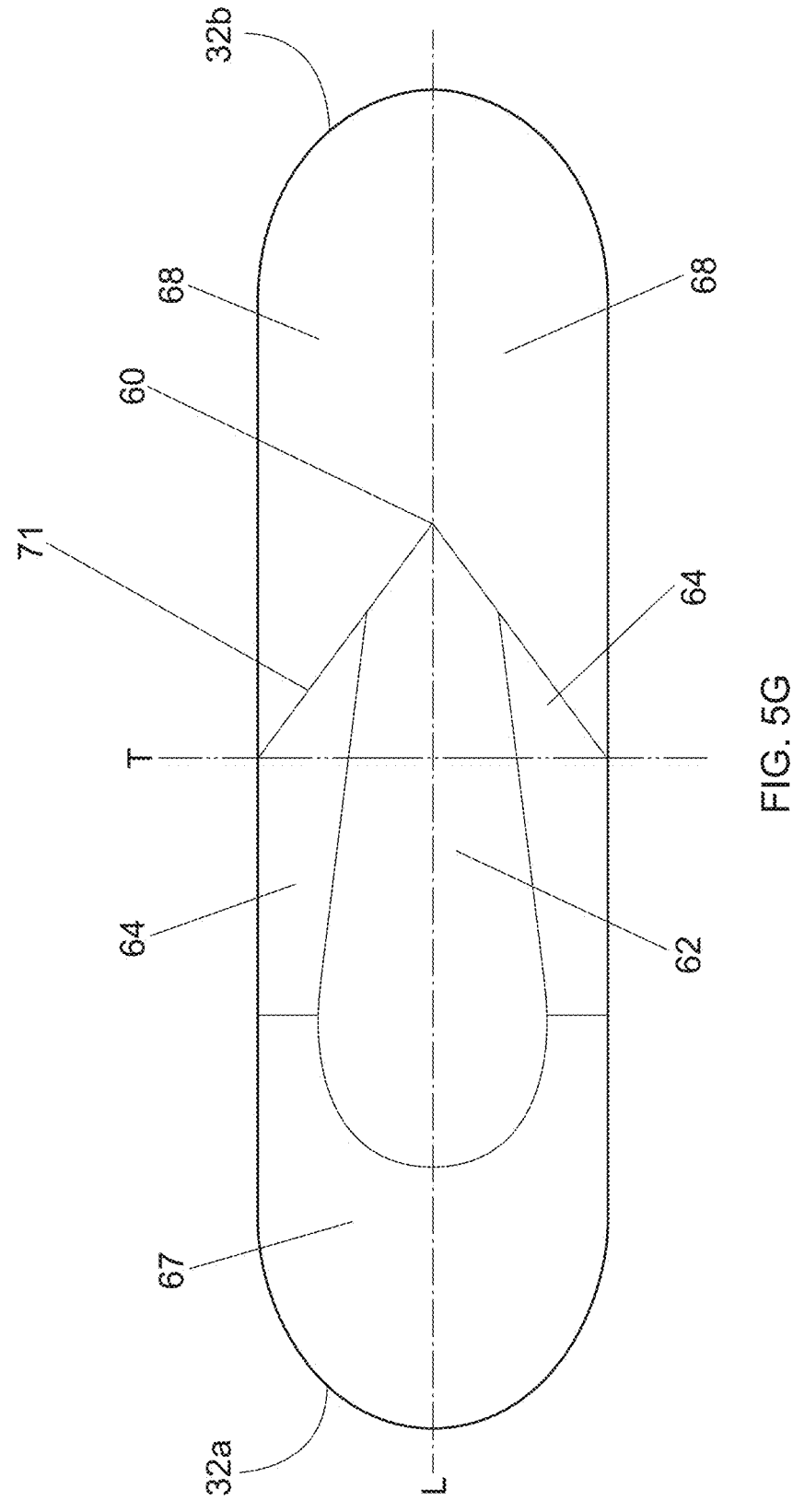
Figure 5H:
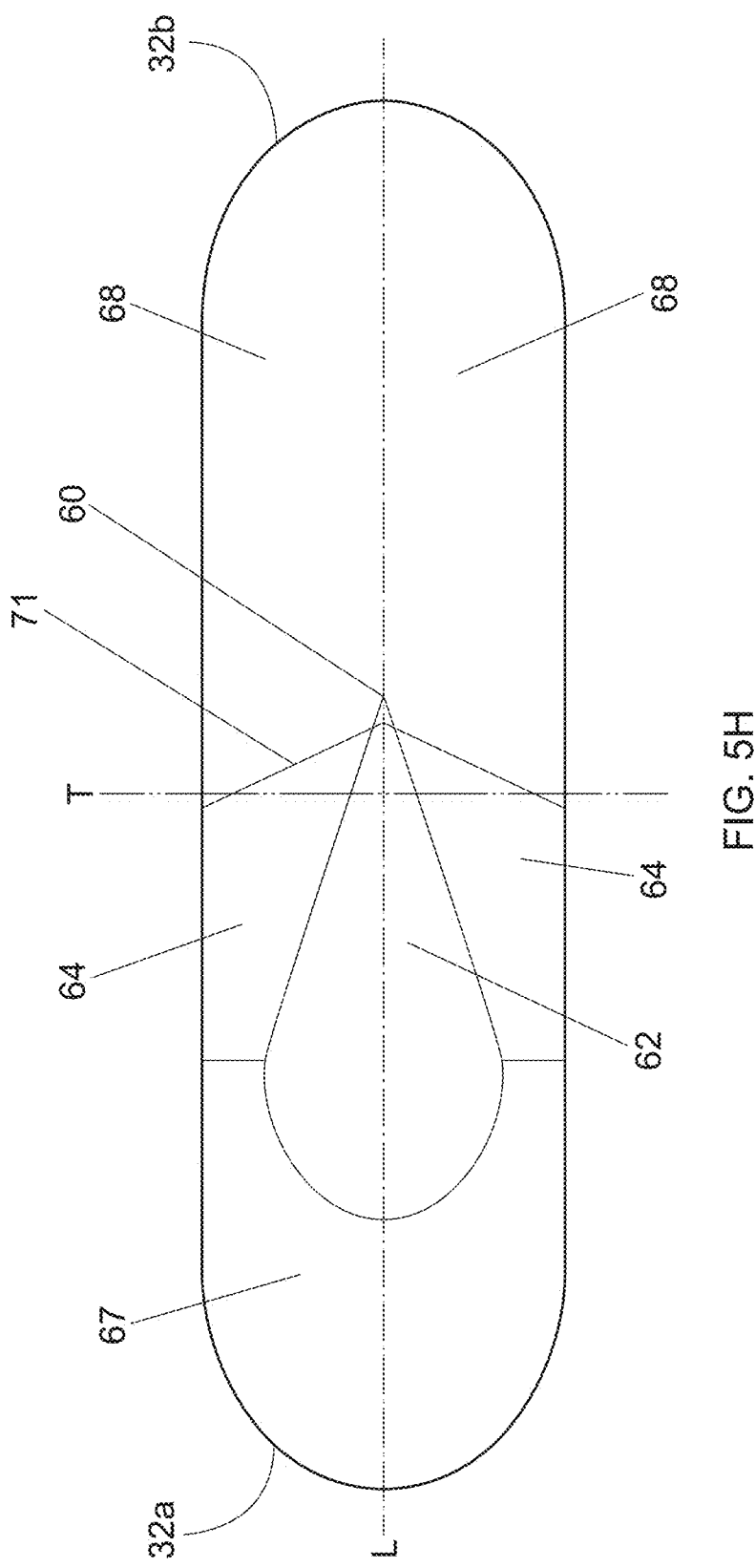
Figure 6C:
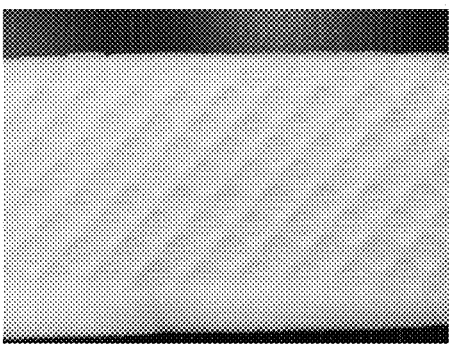
FIG. 6A-F represent examples of potential patterns that may be imparted.
Figure 6B:
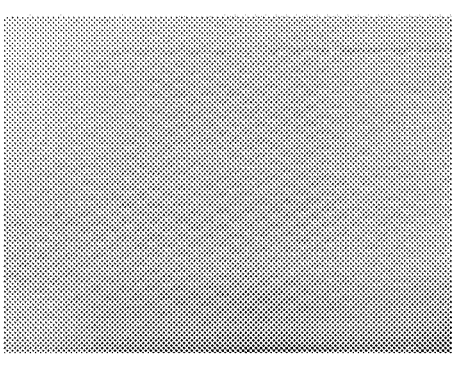
Figure 6A:
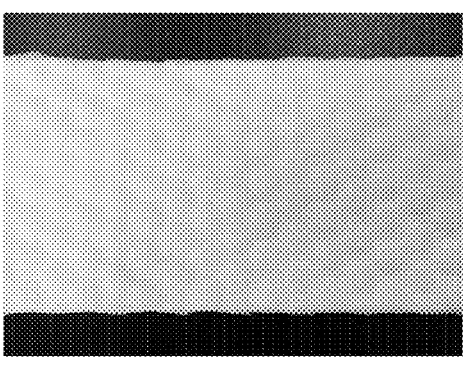
Figure 6F:
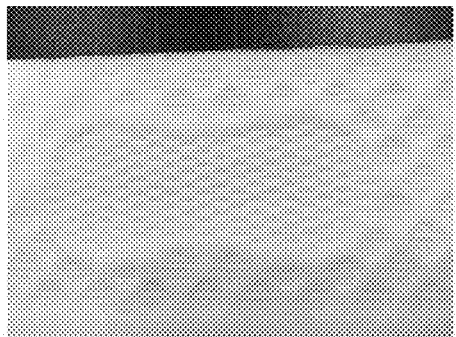
Figure 6E:
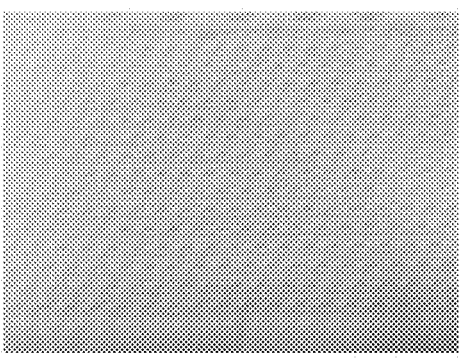
Figure 6D:
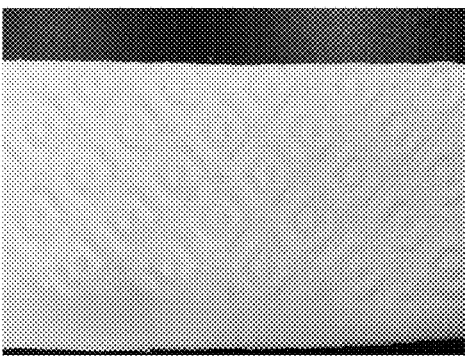

FIGS. 5A-H represent different boundary patterns for an absorbent structure. FIGS. 5A-H have a front edge or leading edge 32*a*, a back edge 32*b*, a first zone 1 identified as 62, a zone 2 identified as 64, a third zone identified as 66, a fourth zone identified as 68, and a boundary convergence area 60. FIGS. 5G-H have an additional zone 67. All of the boundary patterns have a boundary convergence area located in the back half or back end of the article. Said otherwise, the boundary convergence area is located at a point greater than 50% of the total length of the article along the longitudinal axis from the front edge of the article. As shown in the figures, the boundary convergence area may be defined as the point on the article wherein three or more bending lines meet.

TABLE 1

| Sample | Zone A | | | | | |
| | CD | | MD | | CD/MD | |
| | Peak/ | | Peak/ | | Ratio | |
| | Width (N/m) | Slope/Width (N/mm * m) | Width (N/m) | Slope/Width (N/mm * m) | Peak Ratio | Slope Ratio |
| --- | --- | --- | --- | --- | --- | --- |
| Invention A | 9.1 | 2.8 | 5.6 | 1.2 | 1.61 | 2.27 |
| Invention B | 32.6 | 20.0 | 17.7 | 5.0 | 1.84 | 4.00 |
| Invention C | 2.6 | 0.5 | 4.6 | 1.0 | 0.56 | 0.48 |
| Prior Art C | 8.0 | 2.3 | 12.5 | 5.0 | 0.64 | 0.46 |
| Prior Art D | 21.6 | 2.9 | 25.1 | 2.7 | 0.86 | 1.07 |
| Prior Art E | 21.8 | 3.9 | 13.5 | 3.2 | 1.62 | 1.19 |
| Prior Art F | 11.3 | 2.6 | 17.3 | 4.7 | 0.65 | 0.56 |
| Prior Art G | 12.1 | 2.6 | 17.8 | 4.0 | 0.68 | 0.66 |

TABLE 1-continued

| | Zone A | | | | | |
|---|---|---|---|---|---|---|
| | CD | | MD | | CD/MD | |
| | Peak/ | | Peak/ | | Ratio | |
| Sample | Width (N/m) | Slope/Width (N/mm * m) | Width (N/m) | Slope/Width (N/mm * m) | Peak Ratio | Slope Ratio |
| Prior Art H | 20.0 | 3.9 | 33.5 | 6.3 | 0.60 | 0.61 |
| Prior Art I | 10.1 | 2.5 | 11.0 | 2.9 | 0.92 | 0.86 |

TABLE 2

| | Zone B | | | | | |
|---|---|---|---|---|---|---|
| | CD | | MD | | CD/MD | |
| | Peak/ | | Peak/ | | Ratio | |
| Sample | Width (N/m) | Slope/Width (N/mm * m) | Width (N/m) | Slope/Width (N/mm * m) | Peak Ratio | Slope Ratio |
| Invention A | 0.5 | 0.3 | 6.6 | 2.3 | 0.08 | 0.11 |
| Invention B | 3.0 | 0.6 | 17.2 | 5.3 | 0.18 | 0.11 |
| Prior Art C | 9.6 | 2.4 | 4.5 | 3.5 | 2.16 | 0.70 |
| Prior Art D | 37.0 | 5.3 | 65.3 | 7.7 | 0.57 | 0.69 |
| Prior Art E | 11.4 | 2.9 | 14.3 | 3.5 | 0.80 | 0.84 |
| Prior Art F | 9.4 | 1.9 | 25.2 | 7.6 | 0.37 | 0.25 |
| Prior Art G | 1.4 | 0.3 | 4.6 | 1.2 | 0.31 | 0.27 |
| Prior Art H | 22.1 | 4.2 | 29.2 | 4.7 | 0.76 | 0.90 |
| Prior Art I | 6.0 | 1.4 | 8.3 | 2.3 | 0.72 | 0.60 |

Tables 1 and 2 above shows the differential slope stiffness ratio (Cross Direction/Machine Direction) for two different zones in an absorbent article. Zone A represents a portion of the front section of the articles or less than fifty percent of the length of the article along the longitudinal axis when measured from the front edge. Zone B represents a portion of the back section of the articles or less than fifty percent of the length of the article along the longitudinal axis when measured from the back edge.

Without being bound by theory, a product having a front CD/MD slope ratio that within an acceptable range of less than 5 and that is at least 3 times greater than the CD/MD slope ratio of the back portion allows for the product to move with the body in the gluteal groove while producing adequate support in the front portion of the article. Preferably, the CD/MD slope ratio of the back portion is less than 0.5. Preferably, the article exhibits a CD/MD slope ratio of the back portion between 0.01 and 0.5 and a CD/MD slope ratio of the front portion between 1.5 and 5. The CD/MD slope ratio of the front portion may be 1.5, 2.0, 2.5, 3.0, 3.5, 4.0 or 5.0. The CD/MD slope ratio of the back portion may be 0.01, 0.05, 0.1, 0.15, 0.2, 0.25, 0.3, 0.35, 0.4, 0.45, or 0.5.

Applicants have found that by using formation means and the appropriate absorbent materials, an absorbent article can be created that exhibits the desired flexibility in each individual section of the article without sacrificing fluid continuity and absorption capacity. Additionally, the invention samples above represent products capable of attaining a relationship between the front and back sections that was not previously achievable. Specifically, a back section having a CD/MD ratio that is less than 40% of the CD/MD ratio of the front section, such as, between 1% and 40%, between 5% and 35%, between 10% and 30%, between 15% and 25%. Additionally, unlike the prior art which relies on a split back section to achieve a CD/MD ratio in the back below 0.5, it has been found that by selective formation means and the use of a heterogeneous absorbent layer, one can achieve a CD/MD ratio below 0.5 without hindering fluid continuity in the core or the absorption capacity of the core. This is exemplified by the data shown in Table 5.

TABLE 3

| | Average Caliper (mm) | | | Mass (g) | | | Saturation Mass (g) | | | Saturation Mass – Mass | |
|---|---|---|---|---|---|---|---|---|---|---|---|
| | | | Ratio | | | Ratio | | | Ratio | | |
| Sample | Zone A | Zone B | A/B | Zone A | Zone B | A/B | Zone A | Zone B | A/B | Zone A | Zone B |
| Invention A | 1.94 | 2.02 | 0.96 | 0.35 | 0.36 | 0.96 | 4.46 | 4.22 | 1.03 | 4.11 | 3.86 |
| Invention B | 2.75 | 2.46 | 1.12 | 0.53 | 0.50 | 1.07 | 4.83 | 4.57 | 1.04 | 4.3 | 4.07 |
| Prior Art C | 2.58 | 2.68 | 0.96 | 0.42 | 0.38 | 1.11 | 7.09 | 6.37 | 1.09 | 6.67 | 5.99 |
| Prior Art D | 4.91 | 6.44 | 0.76 | 0.74 | 0.97 | 0.76 | 10.70 | 15.80 | 1.65 | 9.96 | 14.83 |
| Prior Art E | 2.47 | 2.56 | 0.96 | 0.43 | 0.48 | 0.90 | 4.89 | 5.56 | 1.46 | 4.46 | 5.08 |
| Prior Art F | 2.38 | 2.13 | 1.12 | 0.57 | 0.52 | 1.09 | 5.54 | 4.56 | 1.74 | 4.97 | 4.04 |
| Prior Art G | 2.63 | 2.33 | 1.13 | 0.65 | 0.36 | 1.79 | 6.99 | 4.40 | 1.62 | 6.34 | 4.04 |
| Prior Art H | 3.21 | 3.35 | 0.96 | 0.85 | 0.77 | 1.10 | 10.60 | 10.02 | 1.00 | 9.75 | 9.25 |
| Prior Art I | 2.11 | 2.19 | 0.96 | 0.51 | 0.45 | 1.12 | 5.18 | 5.44 | 1.66 | 4.67 | 4.99 |

Table 3 represents the average caliper in mm for each zone, the mass of each sample for each zone and the saturation mass for each zone. As shown in the table above, Applicants invention maintains a substantially equal amount of absorption capacity (within 10% difference). This ratio in absorption capacity is maintained while exhibiting the beneficial slope ratios described above and shown in Tables 1 and 2.

TABLE 4

| Sample | Total Edge Compression Ave Energy - Load (N*mm) | Total Edge Recovery Ave Energy - UnLoad (N*mm) | Edge Compression Peak ave distance (mm) |
|---|---|---|---|
| Invention A | 3.04 | 0.62 | 17.36 |
| Invention B | 8.34 | 2.43 | 23.05 |
| Prior Art C | 9.36 | 3.28 | 11.05 |
| Prior Art D | 22.23 | 4.98 | 23.95 |
| Prior Art E | 8.46 | 2.48 | 12.63 |
| Prior Art F | 8.86 | 2.59 | 12.76 |
| Prior Art G | 4.75 | 1.51 | 21.01 |
| Prior Art H | 5.21 | 1.60 | 16.05 |
| Prior Art I | 7.56 | 2.17 | 24.34 |

As can be seen in Table 5, formation means can be utilized to further selectively alter the bending properties of a zone. As shown in the table a pattern may be utilized to deliver Peak force properties below 9.1 N/m CD properties. Note that CD and MD can be interchangeably used as the slope ratio can be 0.48 or 2.08.

Therefore there can be multiple zones that have different CD and MD bending performance. For instance it is possible to make any zone have CD Peak/Width of the range of 0.5 N/m, via the use of deep separation techniques, up to 32.6 N/m, via the use of fiber orientation of the heterogeneous structure. Values in between are made possible via similar means and the use of formation means technologies described previously.

TABLE 5

| Sample | CD Peak/Width (N/m) | CD Slope/Width (N/mm * m) | MD Peak/Width (N/m) | MD Slope/Width (N/mm * m) | CD/MD Ratio Peak Ratio | CD/MD Ratio Slope Ratio |
|---|---|---|---|---|---|---|
| Invention C | 2.6 | 0.5 | 4.6 | 1.0 | 0.56 | 0.48 |

Additionally, as shown in Table 6, it has been found that by selecting specific patterns, one can dial in the desired bunched compression and MD bending performance for a given zone. The data shown in Table 6 is specifically the bending performance measured using a bunched compression method. The corresponding MD Peak bending property is extrapolated from the bunched compression utilizing a mathematical procedure that correlates MD Peak bunched compression to the MD Peak bending value measured in the 3 point bending test method. The patterns of Table 6 are shown in FIGS. 5A-F. As shown in FIGS. 5A-F, one can achieve a variety of patterns, each pattern exhibiting different mechanical properties. By utilizing a tooling that include more than one pattern, one can impart a plurality of patterns onto one absorbent article or absorbent article core thereby creating a plurality of zones that may be separated by boundaries.

TABLE 6

| Pattern | MD: Peak Bunched Compression Test (grams) | MD: Peak/Width (3-point bend) (N/m) | NMR-Residual 1.0 mm (□L) | NMR Kinetics (% Peak Amplitude Reduction in 30 seconds) following gush dose |
|---|---|---|---|---|
| A: JF2 | 150 | 6.21 | 48 | 60 |
| B: DB1 | 180 | 7.23 | 96 | 40 |
| C: Diamonds | 210 | 8.38 | 132 | 30 |
| D: RS1 | 270 | 6.94 | 114 | 25 |
| E: Small Circles | 130 | 5.49 | 120 | 27 |
| F: DiamDB1 | 160 | 6.58 | 108 | 23 |

In addition to being able to dial in in the mechanical properties, one can also change the fluid handling properties for zones within an absorbent article or absorbent core. As shown in Table 7 below, the different inventions have a range of NMR Residual fluid ranging from 594 to 48 µL such as, for example, 100 µL, 150 µL, 200 µL, 250 µL, 300 µL, 350 µL, 400 µL, 500 µL, 550 µL. Similar to the mechanical data above, different patterns may be used to dial in the desired fluid handling properties for a given zone or zones within the absorbent article or absorbent core as shown also in FIG. 6 that shows how different patterns illustrated in FIGS. 5A to 5F deliver differences in both the NMR residual fluid ranging from 132 µL to 48 µL such as, for example, 50 µL, 60 µL, 70 µL, 80 µL, 100 µL, 110 µL, 120 µL, or 130 µL. At the time it can also be shown that these different patterns also distribute a fluid insult or gush dose away from the loading site at different rates according to the NMR Kinetics result of (% Amplitude reduction within 30 seconds of the 'gush dose' fluid insult.

TABLE 7

| Fluid Handling Data - NMR | |
|---|---|
| | NMR-Residual 1.0 mm (µL) |
| Invention A | 594 |
| Invention B | 177 |
| Invention C | 48 |
| Prior Art C | 198 |
| Prior Art D | 372 |
| Prior Art E | 210 |
| Prior Art F | 183 |
| Prior Art G | 138 |
| Prior Art H | 162 |
| Prior Art I | 75 |

| | |
|---|---|
| Invention A | Zoned Pad DEE034 Opt 3 (270 mm) |
| Invention B | Zoned Pad DEE049 Opt 7 (size 3)270 mm) |
| Invention C | Jellyfish Pattern Zone |
| Prior Art C | Always Infinity Size 3Heavy Flow |
| Prior Art D | Always Maxi Jumbo Extra Heavy Overnight Pads |
| Prior Art E | U by Kotex Cleanwear - Ultra Thin Pads - Heavy Flow |
| Prior Art F | U by Kotex Fitness - Ultra Thin Pads - Heavy Flow |
| Prior Art G | Bodyform Ultra thin longThin Long |
| Prior Art H | Stayfree ultra thin ultra longUltra Thin Super Long |
| Prior Art I | Sofy Naked Feel 240 mm |
| Invention A | Zoned Pad DEE034 Opt 3 (270 mm) |
| Invention B | Zoned Pad DEE049 Opt 7 (size 3) |
| Invention C | Jellyfish Pattern Zone |
| Prior Art C | Always Infinity Size 3 |
| Prior Art D | Always Maxi Jumbo |
| Prior Art E | U by Kotex Cleanwear - ultra thin pads - heavy flow |
| Prior Art F | U by Kotex Fitness - ultra thin pads - heavy flow |
| Prior Art G | Bodyform Ultra thin long |
| Prior Art H | Stayfree ultra thin ultra long |
| Prior Art I | Sofy Naked Feel 240 mm |

As shown above, different patterns may create different fluid handling and mechanical properties within the same structure. Utilizing more than one formation means pattern, more than one formation means pattern and fluid etching, or by removing a fraction of the vertical core layer at set points to create a pattern.

The surprising value of these measurements is in identifying unique new structures and products which have an optimized bunch compression in both the dry and wet states over multiple cycles of movement, an ability to conform to tight bending radii without creasing or breaking, and to provide a moderate level of resiliency so as to be invisible to the consumer while she is wearing the product.

As shown in the tables above, by creating different zones within an absorbent article, one may create an article that has at least two zones, such as a Zone 1 and a side Zone 2 wherein the CD/MD slope ratio is greater than 1 in zone 1 and the article has a total edge compression energy load of less than 8.4 mJ or a Total Edge Recovery Energy-UnLoad of less than 2.4 mJ in Zone 2.

Figure 19:
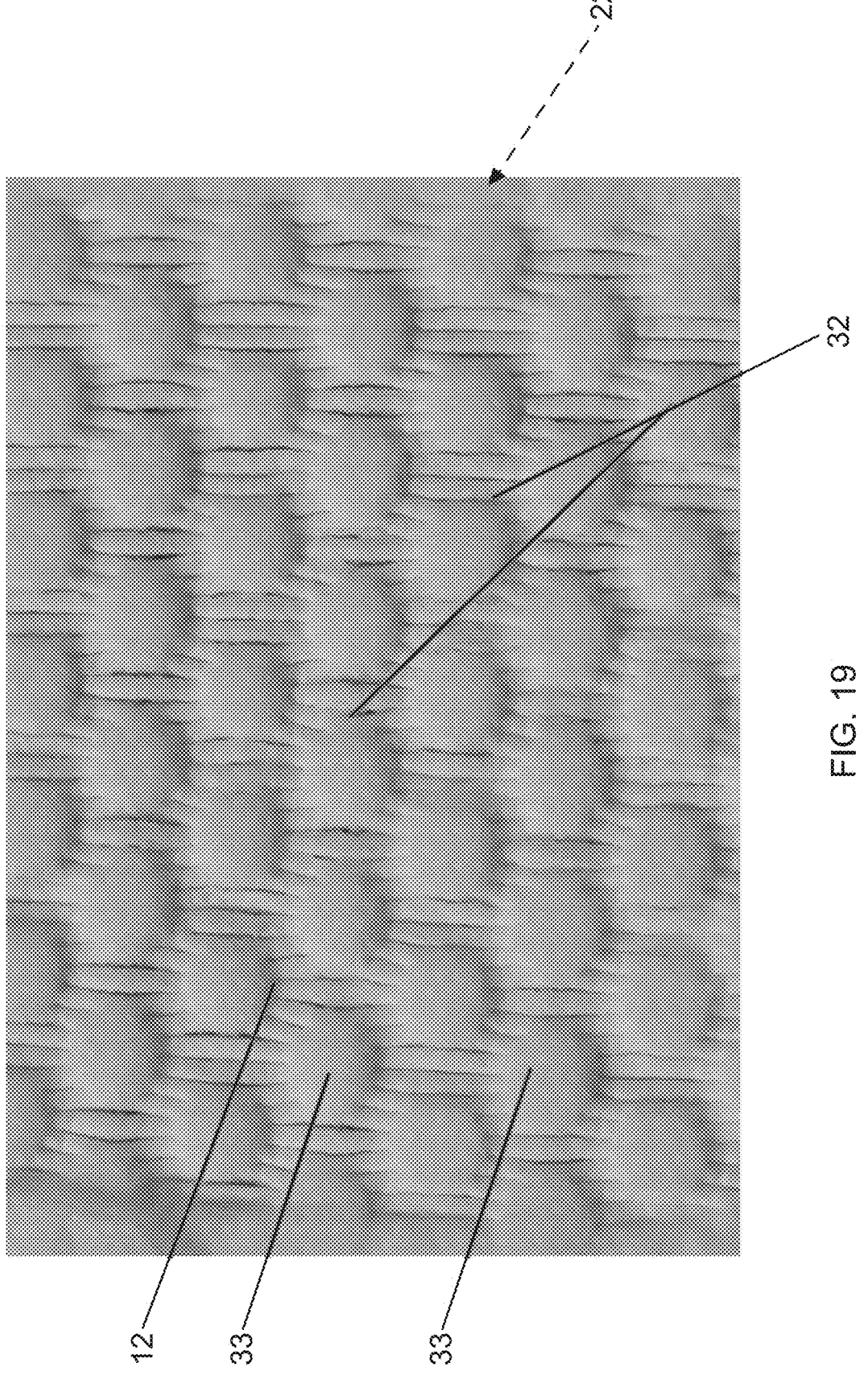
FIG. 19 is a top view of an alternative pattern.
Figure 20:
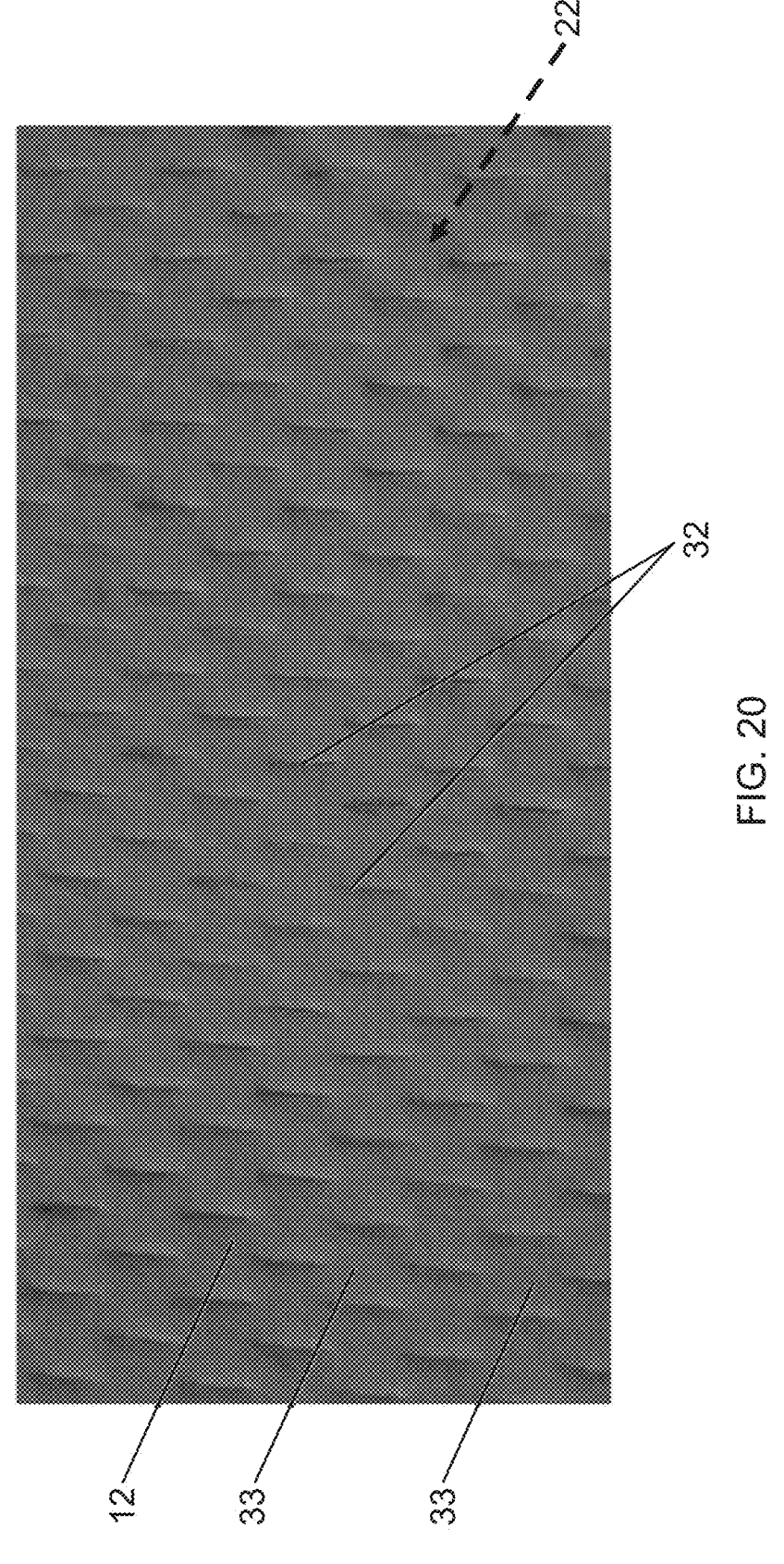
FIG. 20 shows a top view of alternative patterns.
Figure 21:
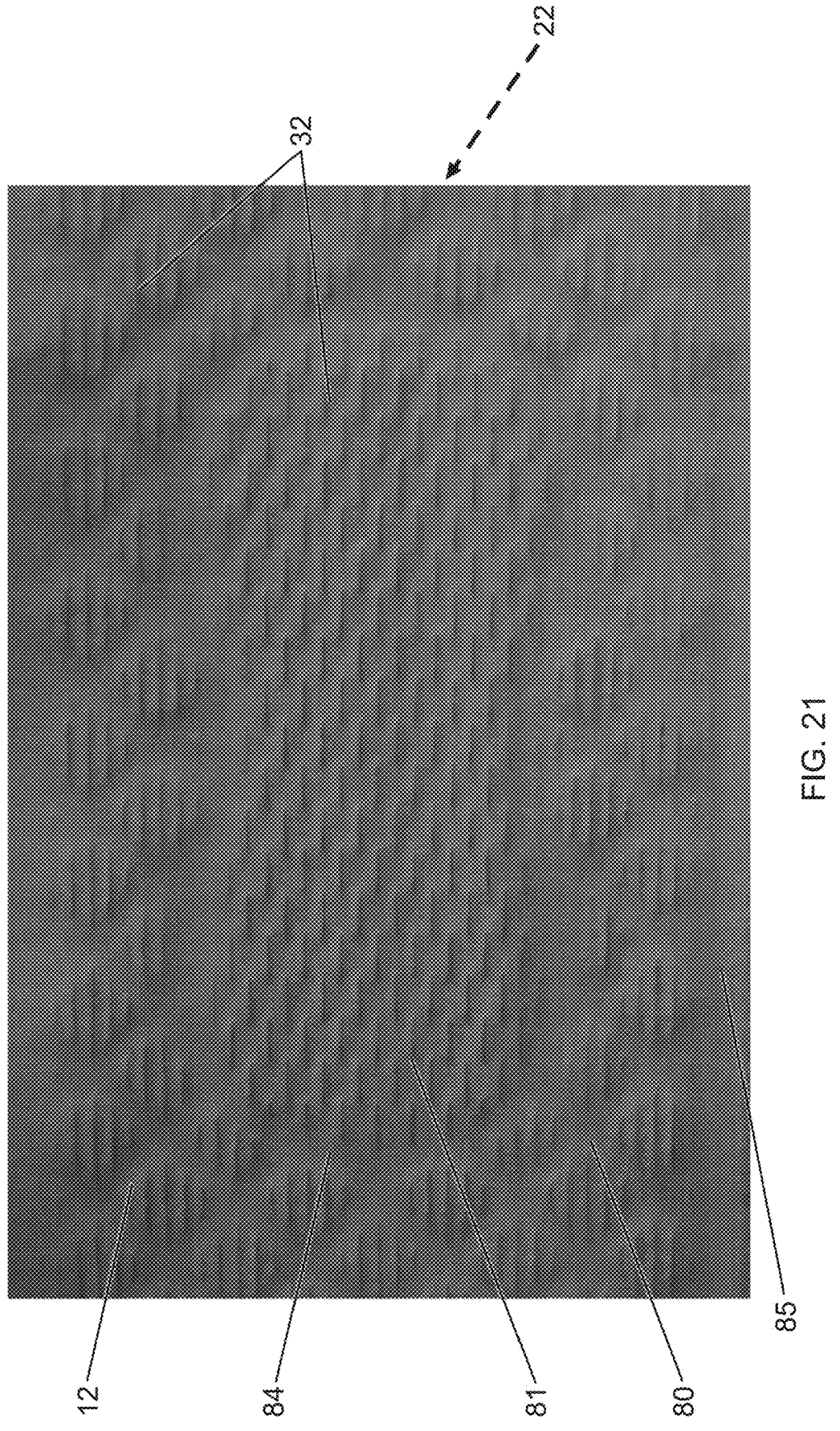
FIG. 21 shows a top view of alternative patterns.

As shown in FIGS. 19 to 21, a variety of patterns could be used. The patterns include zones. Zones are areas exhibiting one of either a visual pattern, a topography, an absorption rate or property, a bending parameter, a compression modulus, a resiliency, a stretch parameter or a combination thereof. The visual pattern may be any known geometric shape or pattern that is visual and can be conceived by the human mind. The topography may be any known pattern that is measurable and can be conceived by the human mind. Zones may be repeated or discrete. Zones may be orthogonal shapes and continuities that provide a visual appearance. The use of zones allows for tailoring of the fluid handling and mechanical properties of and within the pad. The integrated absorbent structure may have one or more visual patterns including zones along one of either the longitudinal or lateral axis of the integrated layers. The integrated layers may have two or more zones comprising one or more visual patterns. The two or more zones may be separated by a boundary. The boundary may be a topographical boundary, a mechanical boundary, a visual boundary, a fluid handling property boundary, or a combination thereof. The boundary property may be distinct from the two zones adjacent to the boundary. The absorbent structure may have a perimeter boundary that exhibits a different property than the one or more adjacent zones to the boundary.

As shown in the tables above, specifically inventions A-C, one may impact the bunched compression of the sample by manipulating the pattern in the sample through formation means. Additionally, one may change the bunched compression of a sample by changing the orientation of the sample.

The absorbent layers may be combined using an intermediate layer between the two layers. The intermediate layer may comprise a tissue, a nonwoven, a film, or combinations thereof. The intermediate layer may have a permeability greater than the 200 Darcy.

Figure 7:
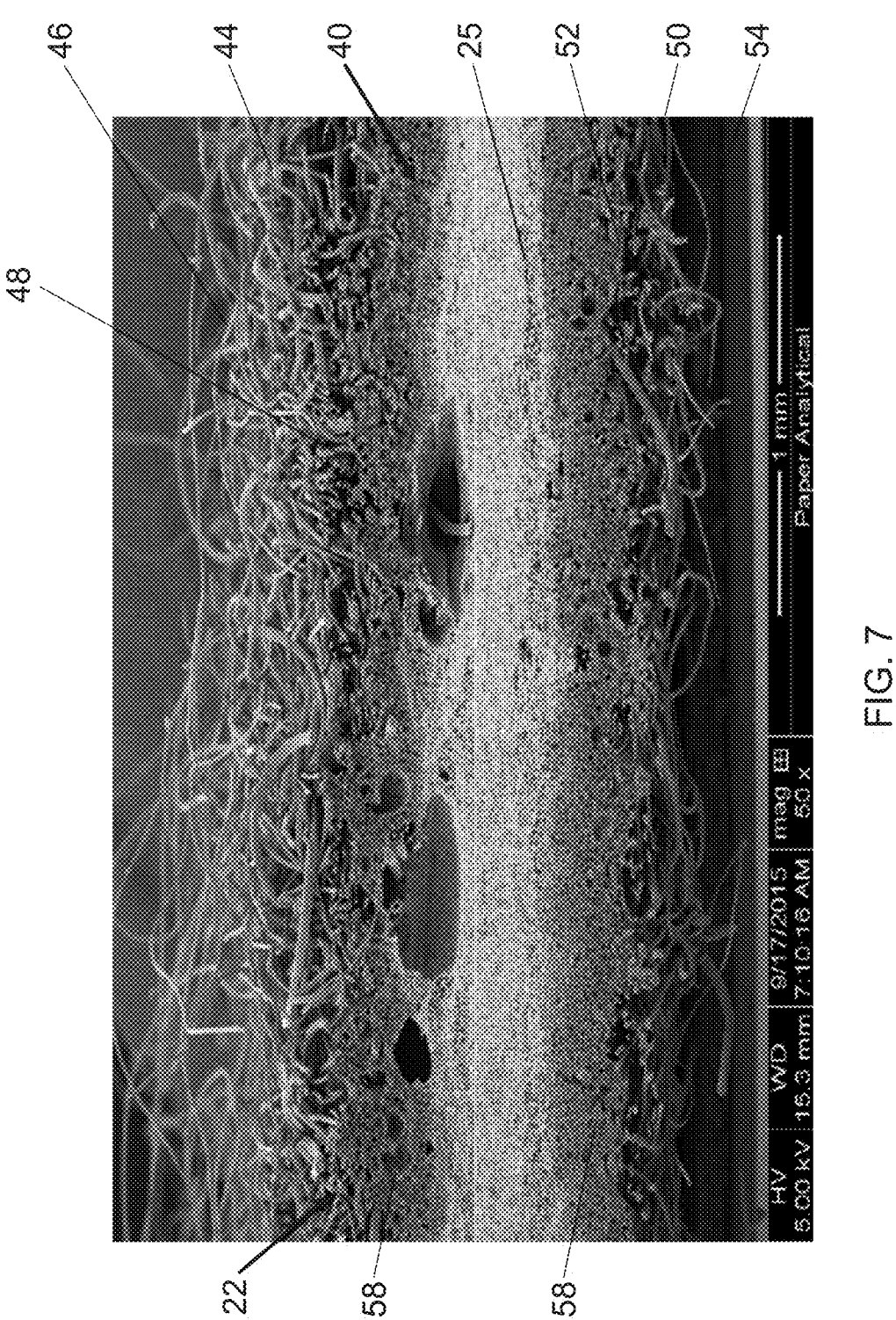
FIG. 7 is an SEM micrograph of a heterogeneous mass.

FIG. 7 is an SEM micrograph of a heterogeneous mass 22 prior to any formation means or forming of canals. As shown in FIG. 7, the absorbent stratum 40 is a heterogeneous mass 22 comprising a first planar nonwoven 44 having a first surface 46 and a second surface 48 and a second planar nonwoven 50 having a first surface 52 and a second surface 54. An open cell foam piece 25 enrobes a portion of the first planar nonwoven 44 and a portion of the second planar nonwoven 50. Specifically, the open cell foam piece 25 enrobes enrobeable elements 58 in both the second surface 48 of the first planar nonwoven 44 and the first surface 52 of the second planar nonwoven 50.

Figure 8:
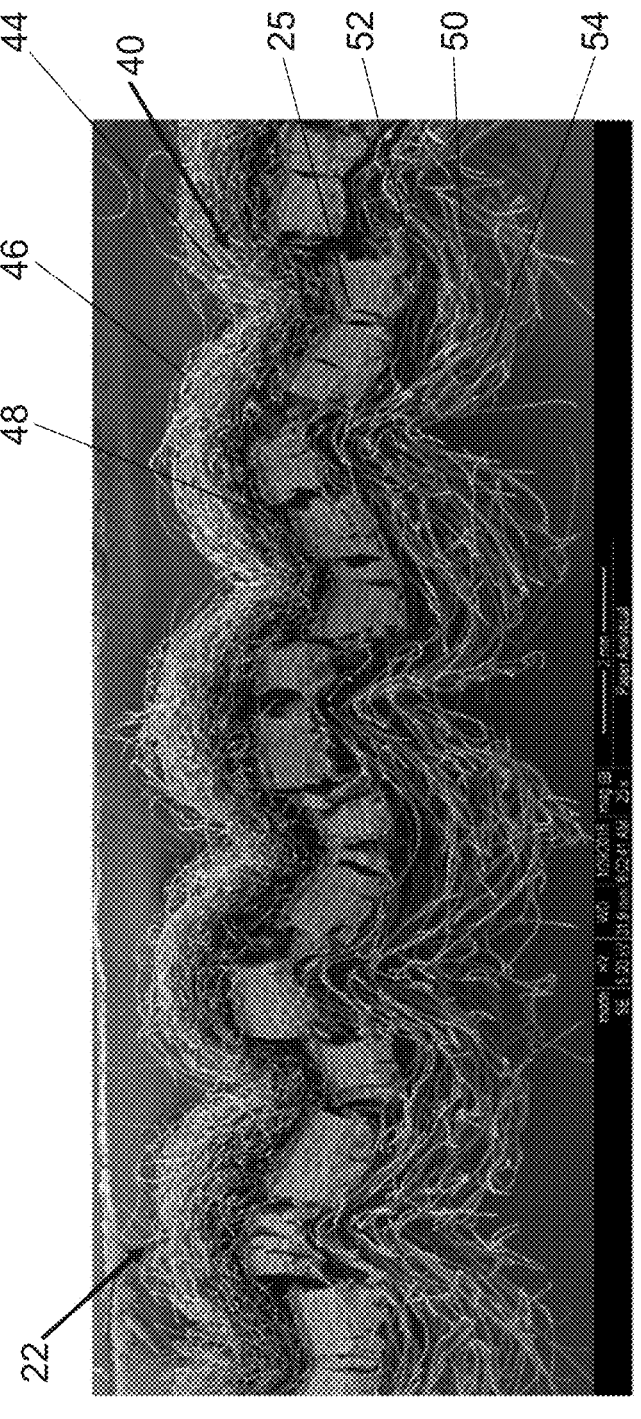
FIG. 8 is an SEM micrograph of a heterogeneous mass.

FIG. 8 is an SEM micrograph of a heterogeneous mass 22 after formation means. As shown in FIG. 8, the absorbent stratum 40 is a heterogeneous mass 22 comprising a first planar nonwoven 44 having a first surface 46 and a second surface 48 and a second planar nonwoven 50 having a first surface 52 and a second surface 54. An open cell foam piece 25 enrobes a portion of the first planar nonwoven 44 and a portion of the second planar nonwoven 50. The planar nowovens are shown as wavy due to the impact of the formation means.

Figure 9:
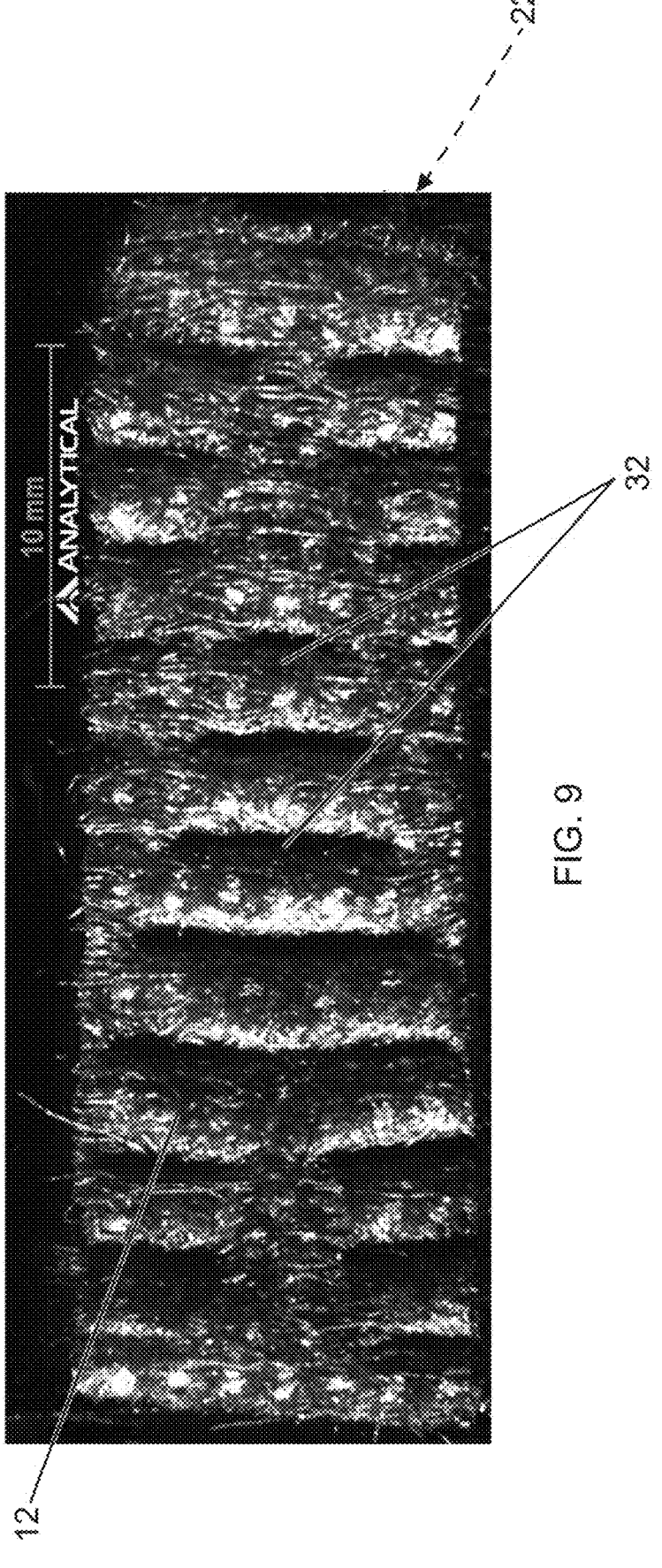
FIG. 9 shows a top view of a topsheet.
Figure 10:
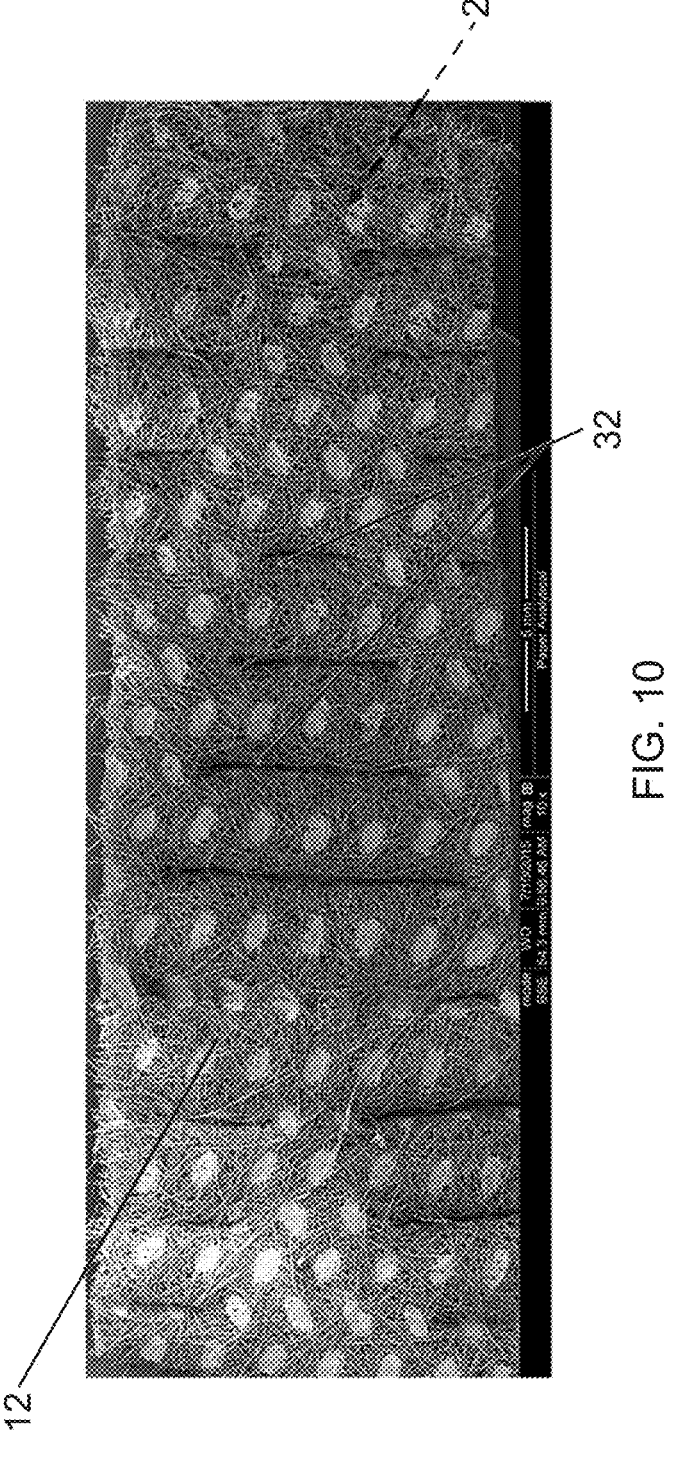
FIG. 10 shows a second top view of the topsheet of FIG. 9.

FIGS. 9 and 10 are top views of a topsheet 12 that has been integrated with a heterogeneous mass 22 stratum. A top view of one or more wells are indicated as 32. FIG. 9 has been created using polarized light.

Figure 11:
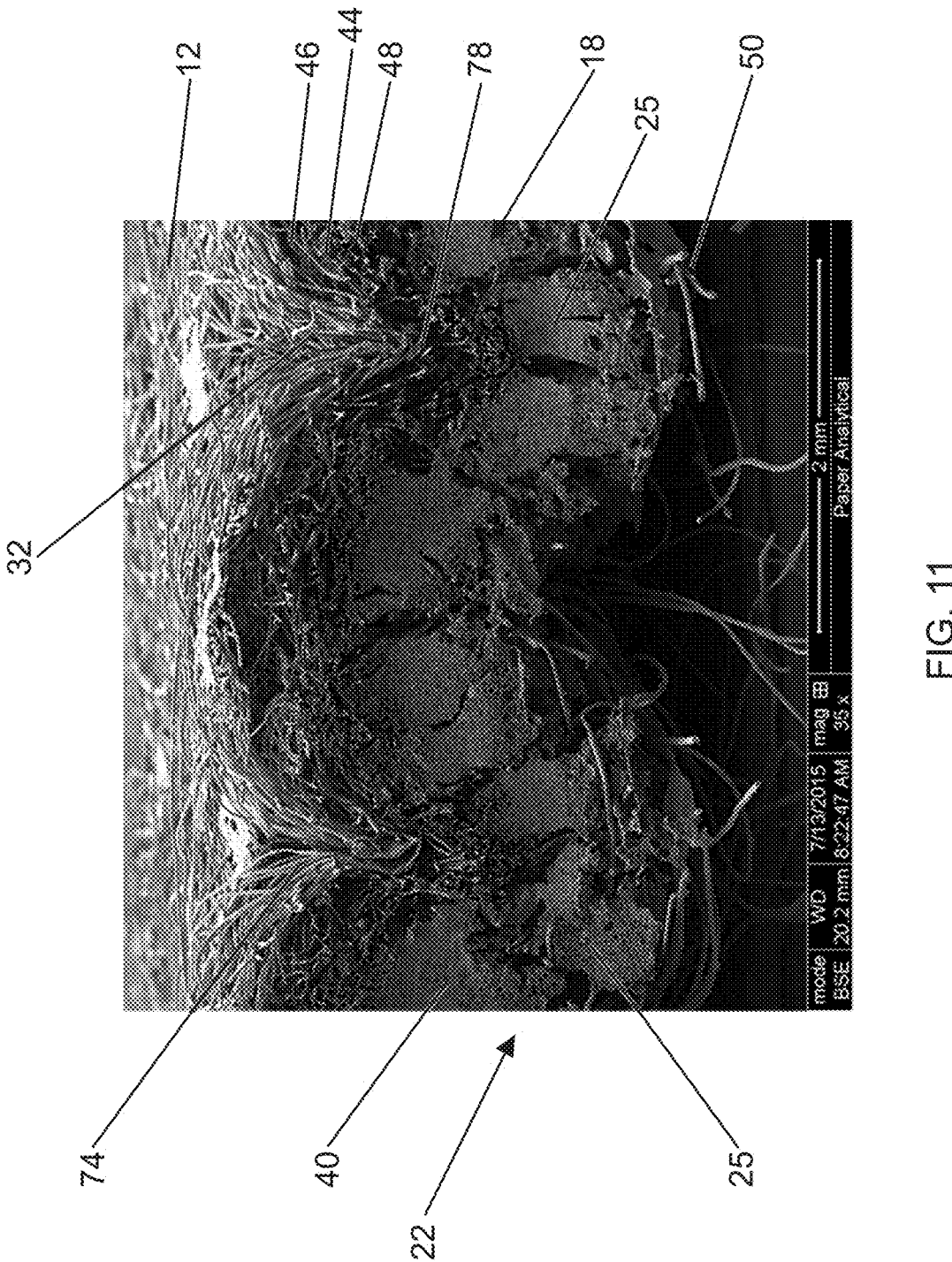
FIG. 11 shows a cross section of FIG. 10.

FIG. 11 is a cross section view of a portion of FIG. 10. FIG. 11 is an SEM micrograph of a heterogeneous mass 22 after formation means. As shown in FIG. 11, the absorbent stratum 40 is a heterogeneous mass 22 comprising a first planar nonwoven 44 having a first surface 46 and a second surface 48 and a second planar nonwoven 50. An open cell foam piece 25 enrobes a portion of the first planar nonwoven 44 and a portion of the second planar nonwoven 50. The planar nowovens are shown as wavy due to the impact of the formation means. A well is 32 is shown between the open cell foam pieces 25. A group of fibers 74 is in the same X-Y plane as the heterogeneous mass 22 layer. The distal end of a well is shown as 78.

Figure 12:
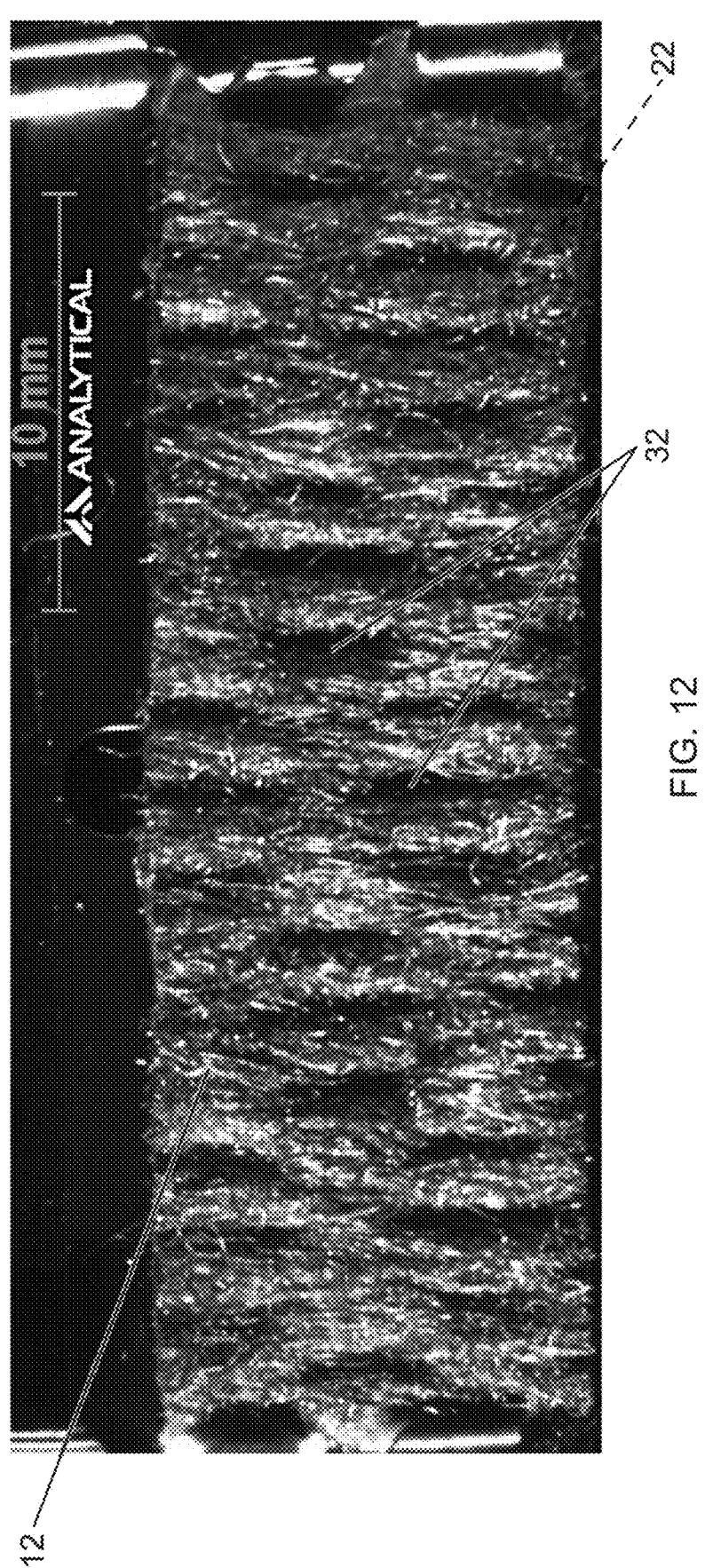
FIG. 12 shows a top view of a topsheet.
Figure 13:
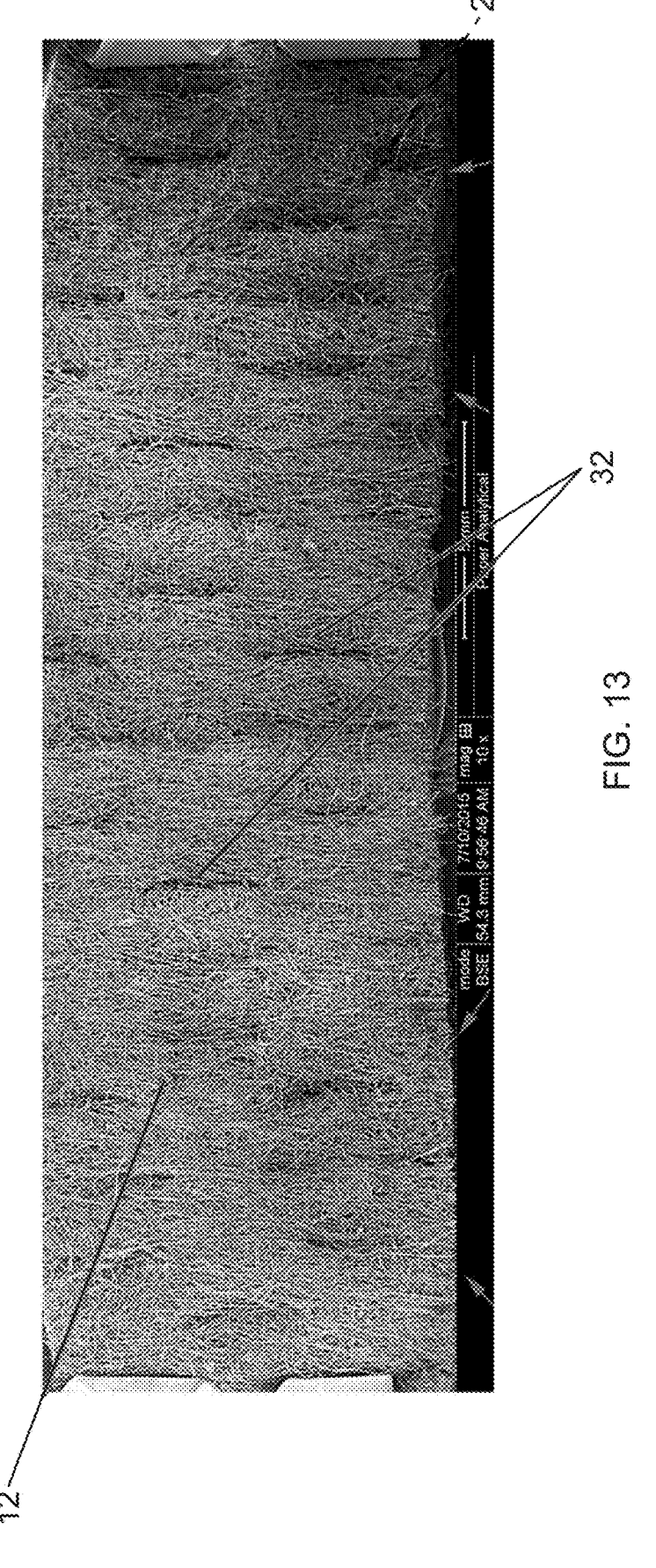
FIG. 13 shows a second top view of the topsheet of FIG. 12.

FIGS. 12 and 13 are top views of a topsheet 12 that has been integrated with a heterogeneous mass 22. A top view of one or more wells are indicated as 32. FIG. 12 has been created using polarized light.

Figure 14:
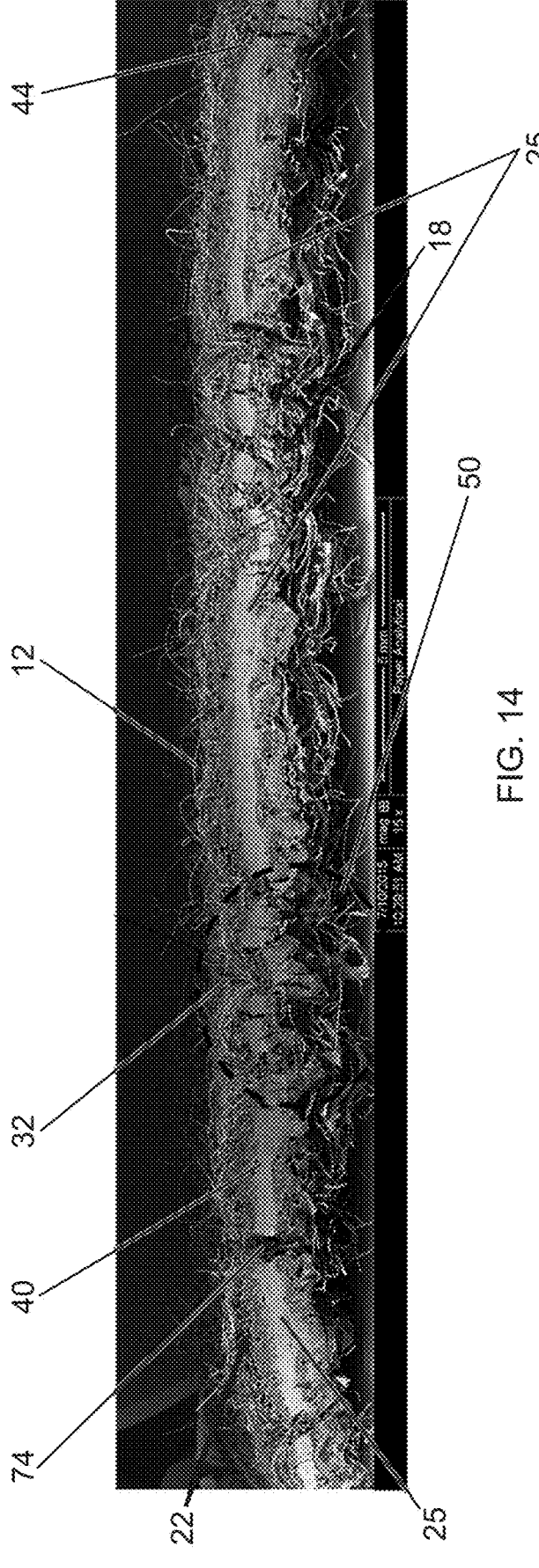
FIG. 14 shows a cross section of FIG. 13.

FIG. 14 is a cross section view of a portion of FIG. 13. FIG. 14 is an SEM micrograph of a heterogeneous mass 22 after formation means. As shown in FIG. 14, the absorbent stratum 40 is a heterogeneous mass 22 comprising a first planar nonwoven 44 and a second planar nonwoven 50. An open cell foam piece 25 enrobes a portion of the first planar nonwoven 44 and a portion of the second planar nonwoven 50. The planar nowovens are shown as wavy due to the impact of the formation means. A well is 32 is shown between the open cell foam pieces 25. A group of fibers 74 is in the same X-Y plane as the heterogeneous mass 22 layer. The distal end of a well is shown as 78.

Figure 15:
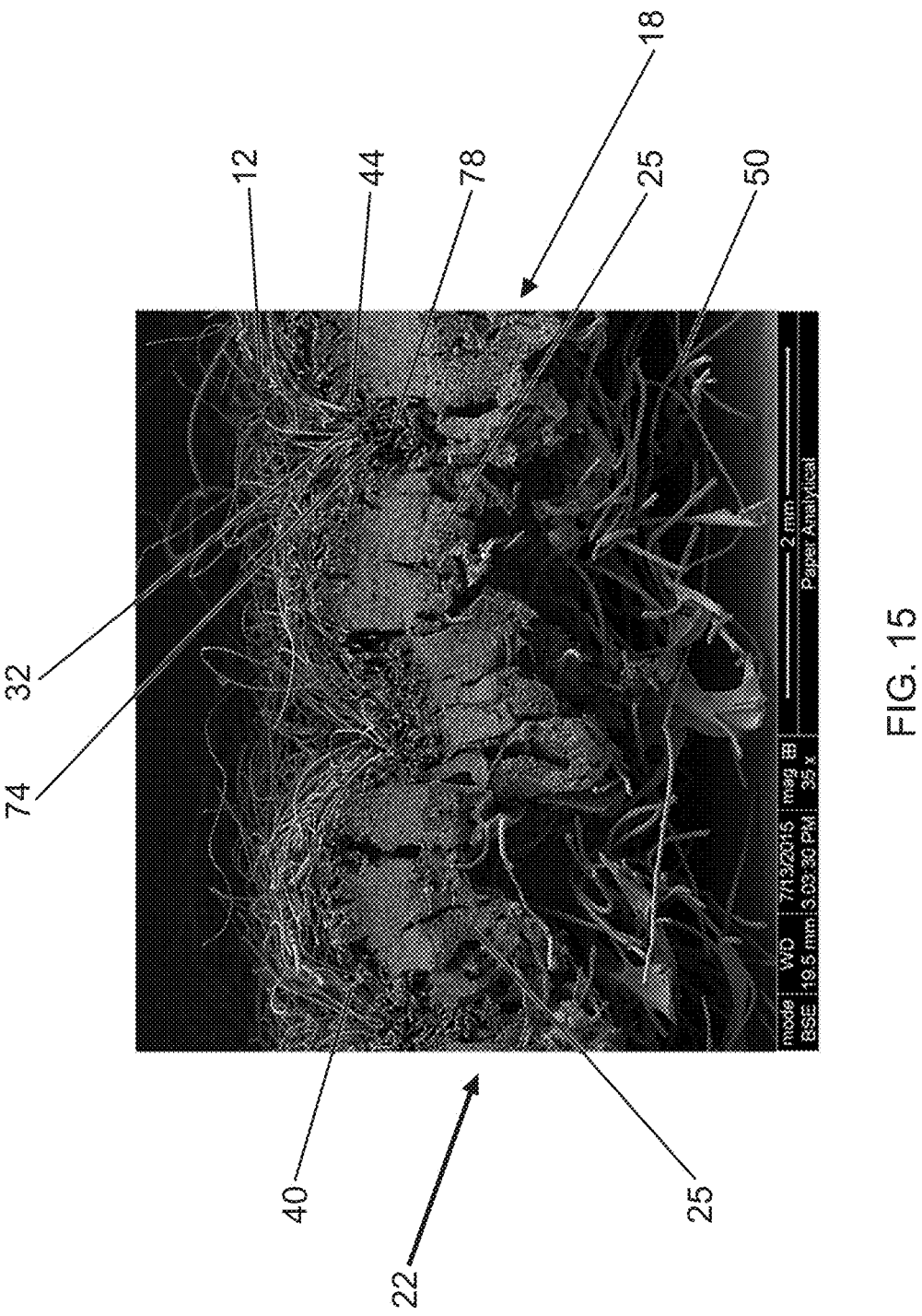
FIG. 15 zoomed in portion of the cross section of FIG. 14.

FIG. 15 is a zoomed in portion of FIG. 15. FIG. 15 is an SEM micrograph of a heterogeneous mass 22 after formation means. As shown in FIG. 15, the absorbent stratum 40 is a heterogeneous mass 22 comprising first planar nonwoven 44 and a second planar nonwoven 50. An open cell foam piece 25 enrobes a portion of the first planar nonwoven 44 and a portion of the second planar nonwoven 50. The planar nowovens are shown as wavy due to the impact of the formation means. A well is 32 is shown between the open cell foam pieces 25. A group of fibers 74 is in the same X-Y plane as the heterogeneous mass 22 layer. The distal end of a well is shown as 78.

Figure 16:
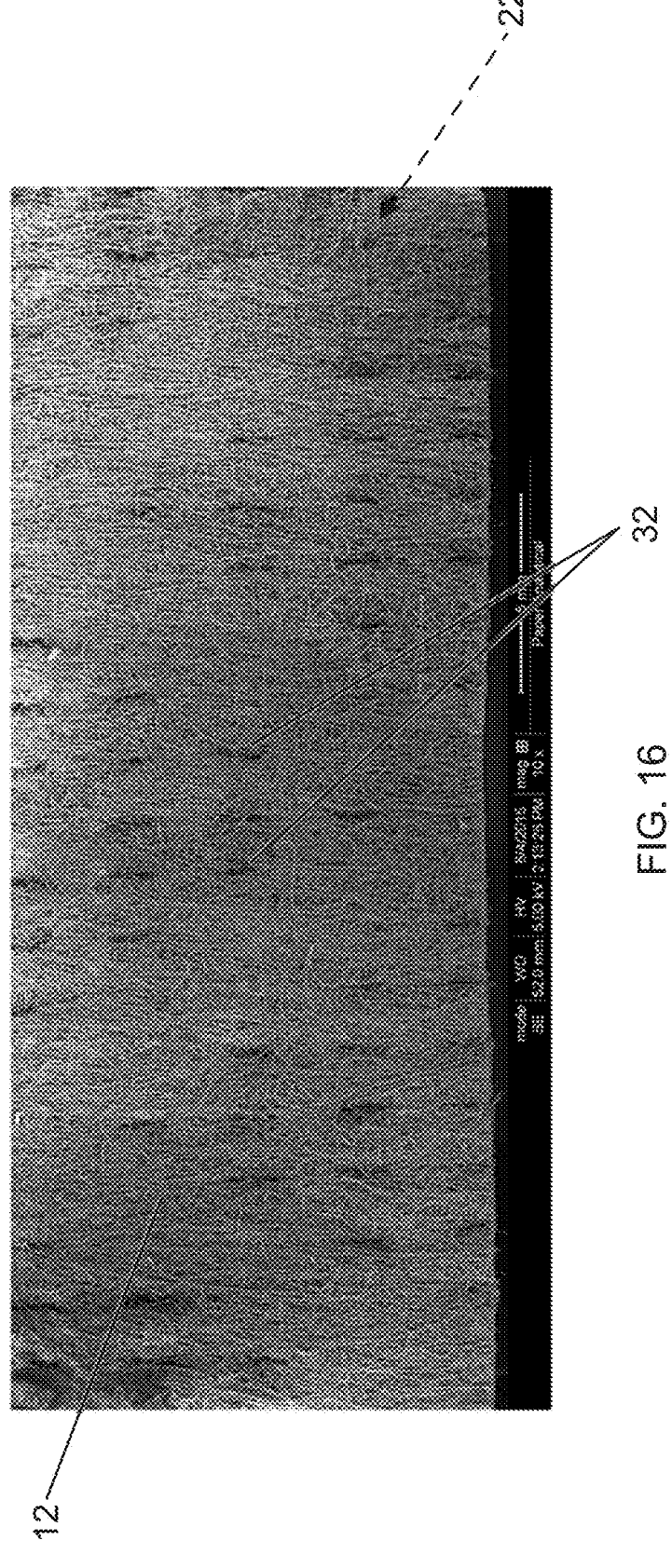
FIG. 16 shows a top view of a topsheet.

FIG. 16 is a top view of a topsheet 12 that has been integrated with a heterogeneous mass 22 stratum. One or more wells are indicated as 32.

Figure 17:
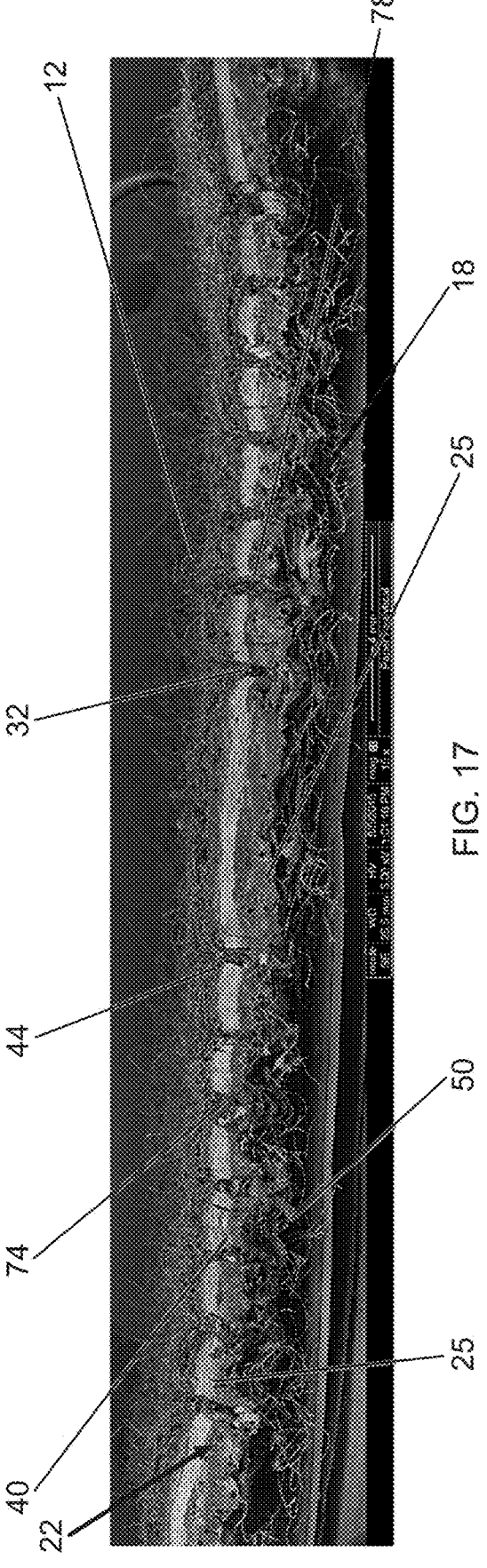
FIG. 17 shows a cross section of FIG. 16.

FIG. 17 is a cross section view of a portion of FIG. 16. FIG. 17 is an SEM micrograph of a heterogeneous mass 22 after formation means. As shown in FIG. 14, the absorbent stratum 40 is a heterogeneous mass 22 comprising a first planar nonwoven 44 and a second planar nonwoven 50. An open cell foam piece 25 enrobes a portion of the first planar nonwoven 44 and a portion of the second planar nonwoven 50. The planar nowovens are shown as wavy due to the impact of the formation means. A well is 32 is shown between the open cell foam pieces 25. A group of fibers 74 is in the same X-Y plane as the heterogeneous mass 22 layer. The distal end of a well is shown as 78.

Figure 18:
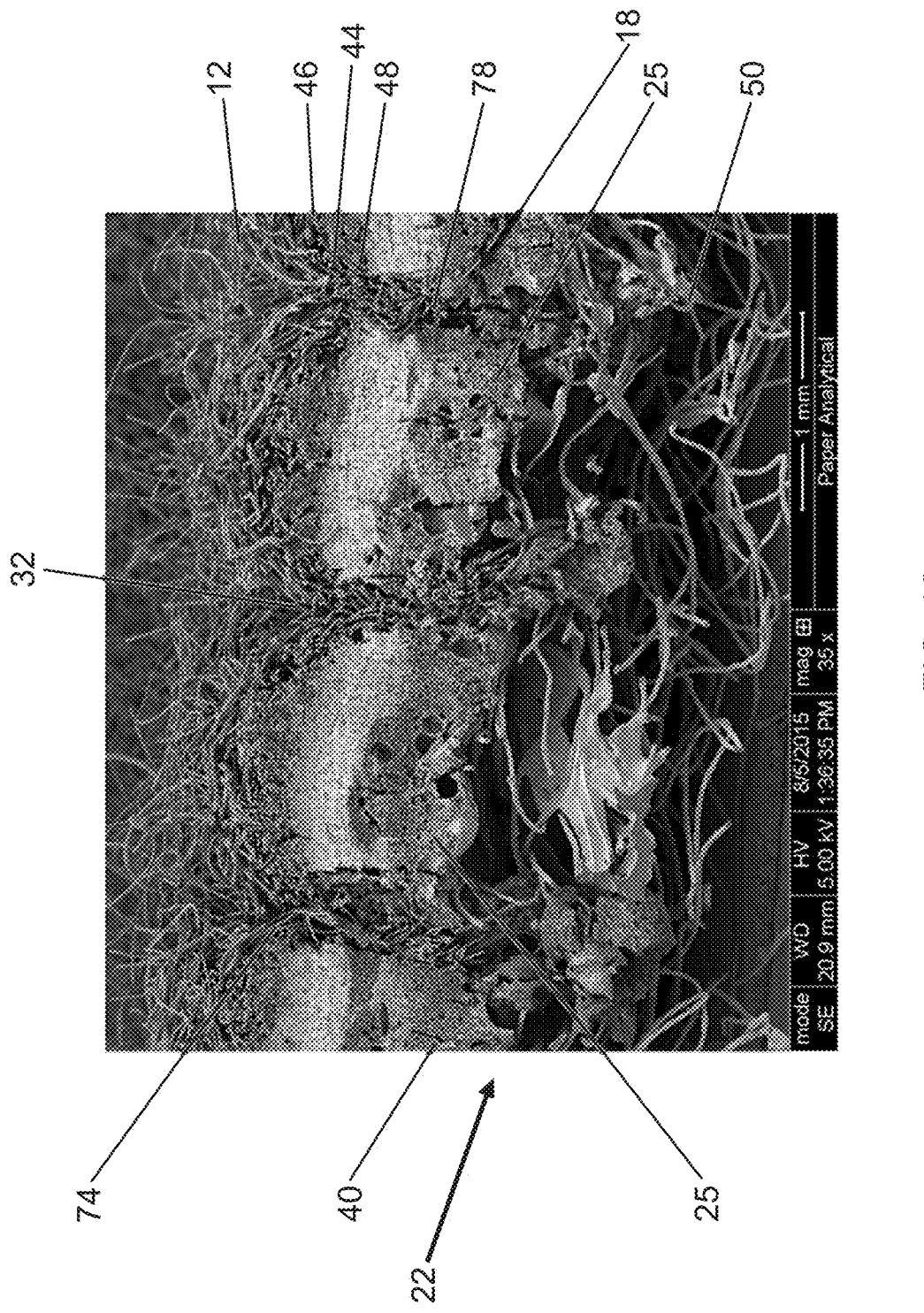
FIG. 18 zoomed in portion of the cross section of FIG. 17.

FIG. 18 is a zoomed in view of a portion of FIG. 17. FIG. 18 is an SEM micrograph of a heterogeneous mass 22 after formation means. As shown in FIG. 18, the absorbent stratum 40 is a heterogeneous mass 22 comprising a first planar nonwoven 44 having a first surface 46 and a second surface 48 and a second planar nonwoven 50. An open cell foam piece 25 enrobes a portion of the first planar nonwoven 44 and a portion of the second planar nonwoven 50. The planar nowovens are shown as wavy due to the impact of the formation means. A well is 32 is shown between the open cell foam pieces 25. A group of fibers 74 is in the same X-Y plane as the heterogeneous mass 22 layer. The distal end of a well is shown as 78.

FIGS. 19-21 are images of different topsheets 12 that have been integrated with a heterogeneous mass 22 stratum. FIGS. 19-21 show elongated wells 32 and non-deformed areas 33 that have not been treated with a deformation means. FIG. 21 show a first zone 80 and a second zone 81 and a first boundary 84 and a second boundary 85. FIG. 21 is a conceptual core showing a plurality of zones within the same product. The different zones are created using forming means. In this case, the core may be modified to provide optimum fluid acquisition in the middle, optimum fluid transportation in the front and back, and enhanced boundary (height, absorbency, etc.) around the perimeter of the pad.

Additionally, each one exhibits a distinct topographical surface and visual geometry. As shown in FIG. 21, more than one geometry may be located within a single absorbent article.

Test Methods

Caliper

Apparatus

The caliper of the zone is quantified using an Edana Caliper or equivalent tester with a precision of 0.01 mm.

Samples

A minimum of 2 representative samples are necessary to complete the testing. The specimen is cut from the center of the zone being sampled.

Procedure

The test apparatus is always zeroed before any measurements are taken. The foot is to apply a target pressure of 0.1 psi. Record the caliper after no more than 5 seconds under the foot pressure.

Calculations

Each of the samples is individually measured and the average of the samples is reported to the nearest 0.01 millimeters.

Sample Mass

The total mass of all replicate samples from a zone was measured on 3 place analytical balance.

Saturation Mass

Apparatus

A container large enough to allow the Sample to lie completely flat, and with a sufficient amount of a 10 w. % saline/water solution to completely immerse the sample. The solution is allowed to equilibrate in a room controlled at 23° C.±3° C. and 50%±2% relative humidity for 6 hours. The 10 w. % solution of sodium chloride is prepared by dissolving the appropriate amount of pure sodium chloride in distilled water.

Procedure

The Sample is completely immersed in the 10 w. % saline/water solution for 30 seconds. The Sample is removed from solution with tweezers and held vertically for 5 seconds to allow excess solution to drip from sample. The Sample mass was recorded using an on 3 place analytical balance.

Calculations

Each of the samples is individually measured and the average of the samples is reported to the nearest 0.01 grams.

Bunch Compression Test

Bunched Compression of a sample is measured on a constant rate of extension tensile tester (a suitable instrument is the MTS Alliance using Testworks 4.0 software, as available from MTS Systems Corp., Eden Prairie, MN, or equivalent) using a load cell for which the forces measured are within 10% to 90% of the limit of the cell. All testing is performed in a room controlled at 23° C.±3° C. and 50%±2% relative humidity. The test can be performed wet or dry.

Figure 22:
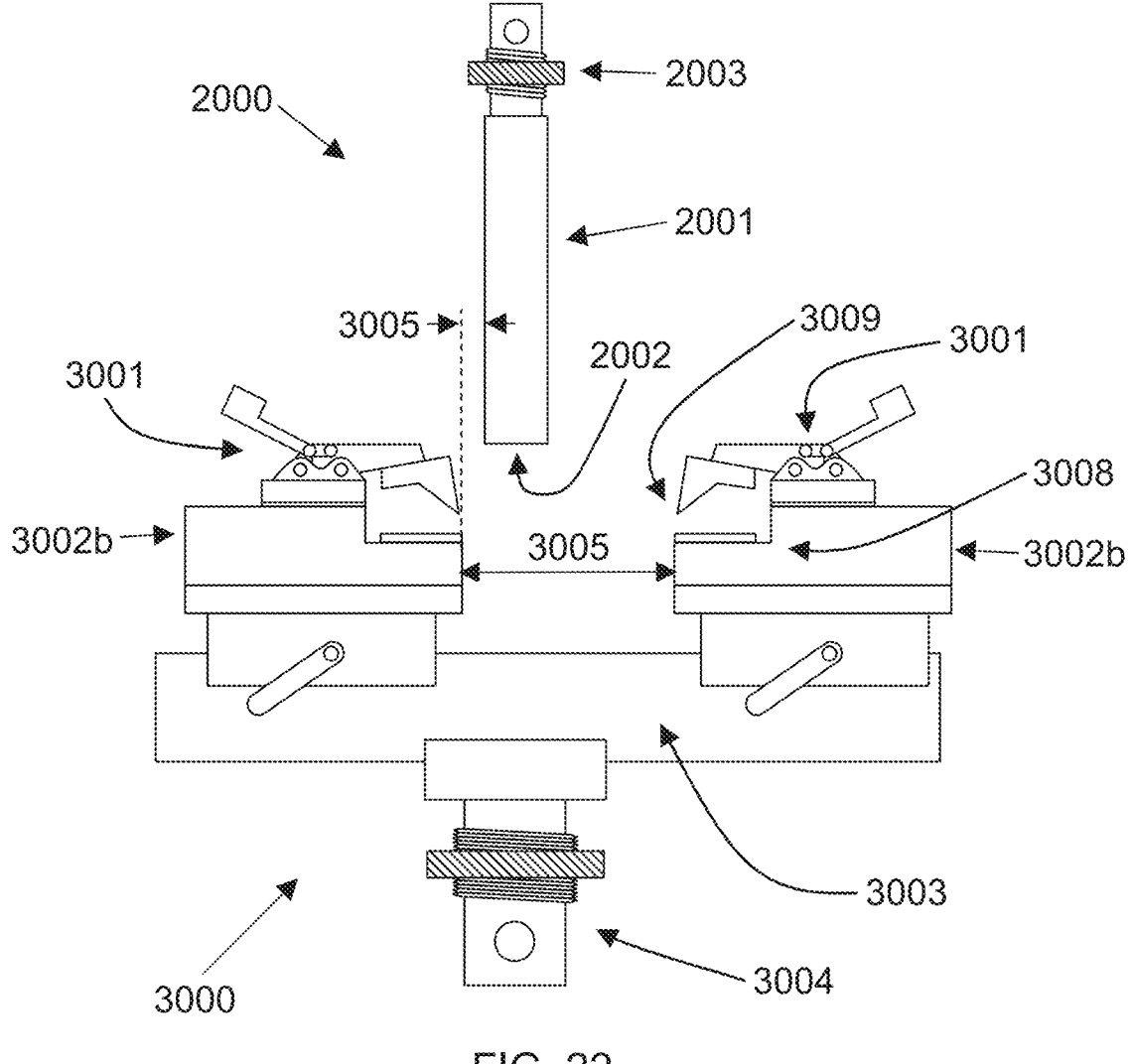
FIG. 22 shows the apparatus for a test method.

As shown in FIG. 22, The bottom stationary fixture 3000 consists of two matching sample clamps 3001 each 100 mm wide each mounted on its own movable platform 3002*a*, 3002*b*. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3° C. and 50%±2% relative humidity for at least 2 hours before testing. When testing a whole article, remove the release paper from any panty fastening adhesive on the garment facing side of the article. Lightly apply talc powder to the adhesive to mitigate any tackiness. If there are cuffs, excise them with scissors, taking care not to disturb the top sheet of the product. Place the article, body facing surface up, on a bench. On the article identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of the midlines.

The specimen can be analyzed both wet and dry. The dry specimen requires no further preparation. The wet specimens are dosed with 7.00 mL±0.01 mL 10% w/v saline solution (100.0 g of NaCl diluted to 1 L deionized water). The dose is added using a calibrated Eppendorf-type pipettor, spreading the fluid over the complete body facing surface of the specimen within a period of approximately 3 sec. The wet specimen is tested 15.0 min±0.1 min after the dose is applied. Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Figure 23A:
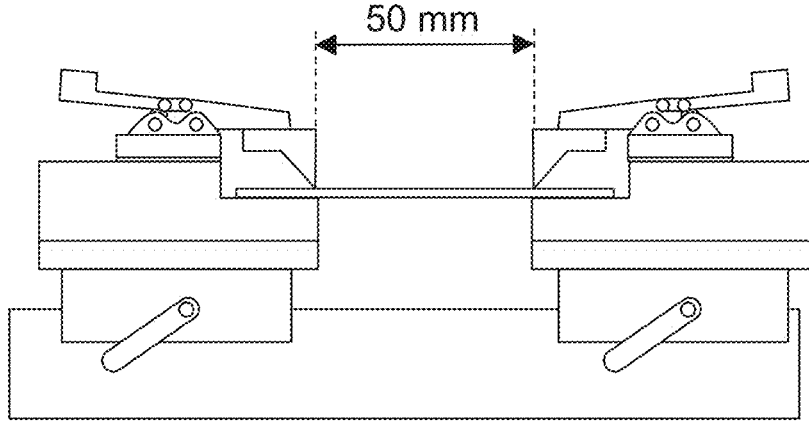
FIG. 23A-B relate to the test method of FIG. 22.
Figure 23B:
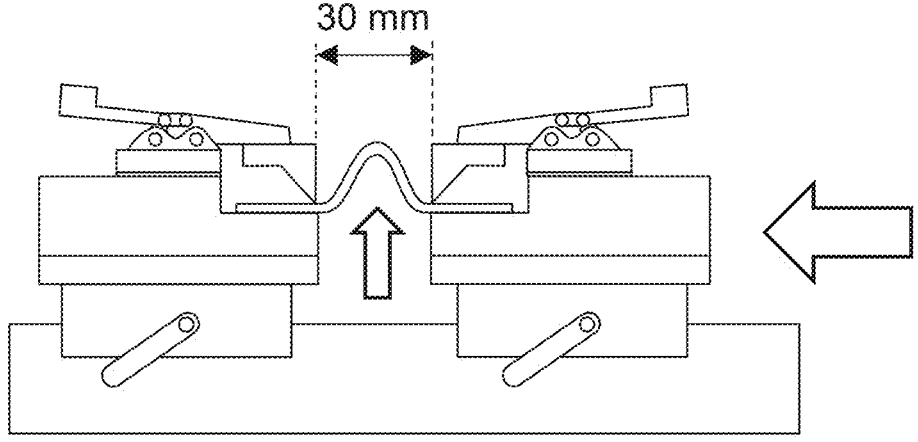

Position the left platform 3002*a* 2.5 mm from the side of the upper plunger (distance 3005). Lock the left platform into place. This platform 3002*a* will remain stationary throughout the experiment. Align the right platform 3002*b* 50.0 mm from the stationary clamp (distance 3006). Raise the upper probe 2001 such that it will not interfere with loading the specimen. Open both clamps. Referring to FIG. 23*a*, place the specimen with its longitudinal edges (i.e., the 100 mm long edges) within the clamps. With the specimen laterally centered, securely fasten both edges. Referring to FIG. 23*b*, move the right platform 3002*b* toward the stationary platform 3002*a* a distance 20.0 mm Allow the specimen to bow upward as the movable platform is positioned. Manually lower the probe 2001 until the bottom surface is approximately 1 cm above the top of the bowed specimen.

Figure 24A:
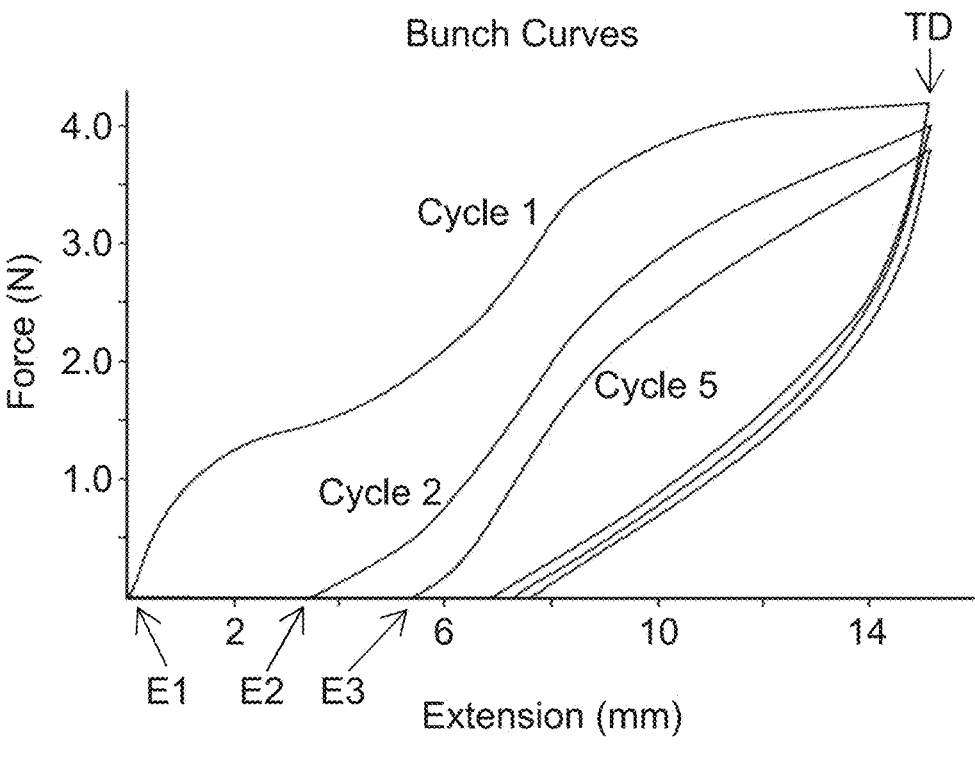
FIG. 24A-B relate to the test method of FIG. 22.
Figure 24B:
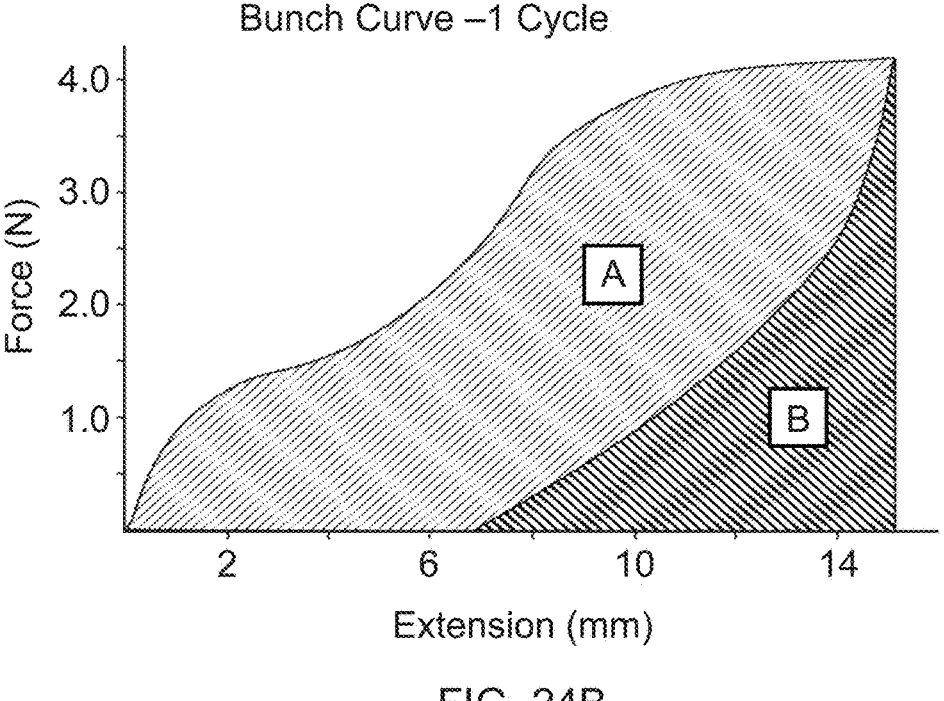
Figure 25:
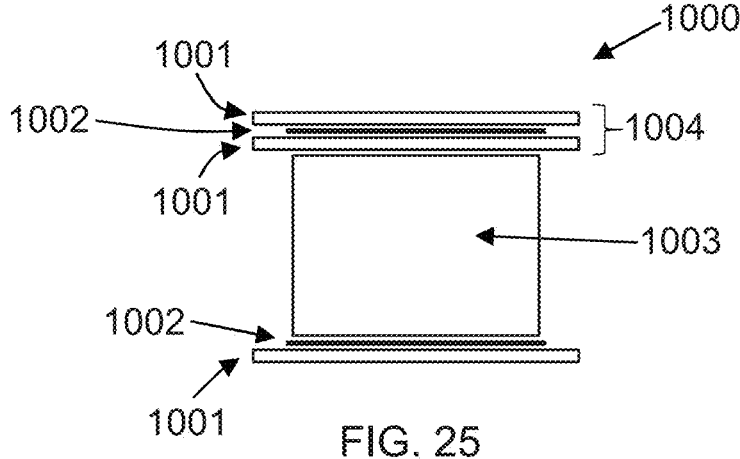
FIG. 25 shows an apparatus for a test method.
Figure 26:
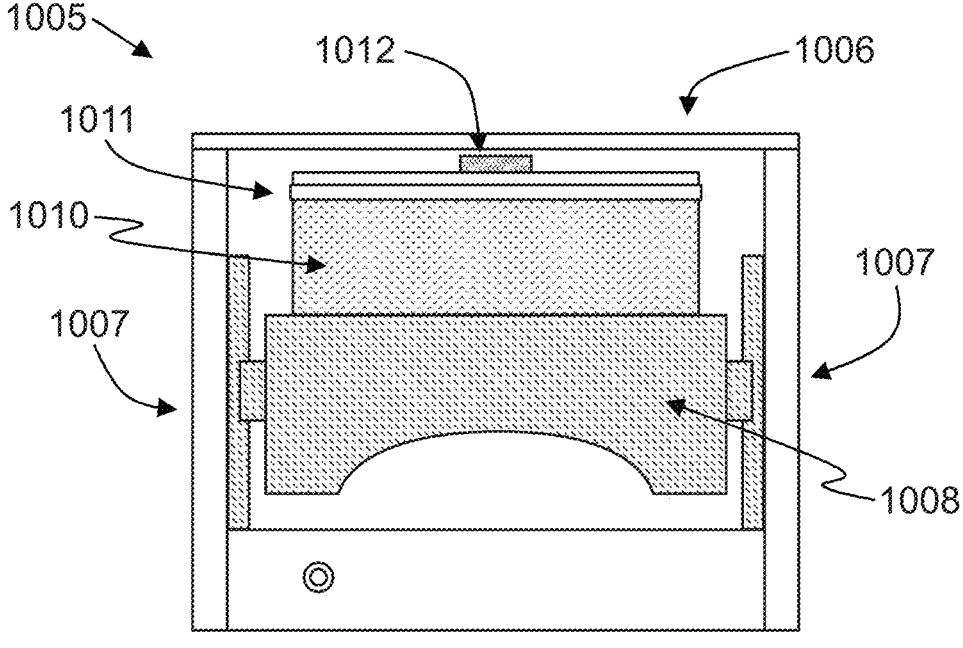
FIG. 26 shows an apparatus for a test method.

Start the test and collect displacement (mm) verses force (N) data for all five cycles. Construct a graph of Force (N) versus displacement (mm) separately for all cycles. A representative curve is shown in FIG. 24*a*. From the curve record the Maximum Compression Force for each Cycle to the nearest 0.01N. Calculate the % Recovery between the First and Second cycle as (TD−E2)/(TD−E1)*100 where TD is the total displacement and E2 is the extension on the second compression curve that exceeds 0.02 N. Record to the nearest 0.01%. In like fashion calculate the % Recovery between the First Cycle and other cycles as (TD−E$_i$)/(TD−E1)*100 and report to the nearest 0.01%. Referring to FIG. 24*b*, calculate the Energy of Compression for Cycle 1 as the area under the compression curve (i.e., area A+B) and record to the nearest 0.1 mJ. Calculate the Energy Loss from Cycle 1 as the area between the compression and decompression curves (i.e., Area A) and report to the nearest 0.1 mJ. Calculate the Energy of Recovery for Cycle 1 as the area under the decompression curve (i.e. Area B) and report to the nearest 0.1 mJ. In like fashion calculate the Energy of Compression (mJ), Energy Loss (mJ) and Energy of Recovery (mJ) for each of the other cycles and record to the nearest 0.1 mJ For each sample, analyze a total of five (5) replicates and report the arithmetic mean for each parameter. All results are reported specifically as dry or wet including test fluid (0.9% or 10%).

Three Point Bend

The bending properties of a sample are measured on a constant rate of extension tensile tester (a suitable instrument is the MTS Insight HSEL using Testworks 4.0 Software, as available from MTS Systems Corp., Eden Prairie, MN) using a load cell for which the forces measured are within 2% to 90% of the limit of the cell. All testing is performed in a room controlled at 23° C.±3° C. and 50%±2% relative humidity.

The bottom stationary fixture consists of two bars 3.175 mm in diameter by 60 mm in length, made of polished stainless steel each mounted on its own vertical fork. These 2 bars are mounted horizontally, aligned front to back and parallel to each other, with top radii of the bars vertically aligned. Furthermore, the fixture allows for the two bars to be move horizontally away from each other on a track so that a span can be set between them while maintaining their orientation. The top movable fixture consists of a third bar also 3.175 mm in diameter by 60 mm in length, made of polished stainless steel mounted on a vertical fork. When in place the bar of the top fixture is parallel to, and aligned front to back with the bars of the bottom fixture. Both fixtures include an integral adapter appropriate to fit the respective position on the tensile tester frame and lock into position such that the bars are orthogonal to the motion of the crossbeam of the tensile tester.

Set the span between the bars of the lower fixture to 25 mm±0.05 mm (center of bar to center of bar) with the upper bar centered at the midpoint between the lower bars. Set the gage (bottom of top bar to top of lower bars) to 1.0 cm.

Samples are conditioned at 23° C.±3° C. and 50%±2% relative humidity two hours prior to testing. Remove the overwrap and release papers were removed from pads. Dust the exposed adhesive surfaces on the back sheet and if present wings with talcum powder to eliminate adhesive tack. Remove in excess talc from the surfaces. Lay the pads flat, top sheet facing upward on a lab bench, and mark the longitudinal midline of the product. Next, mark a lateral line across the product using the longitudinal midline of the wings. If no wings are present mark a lateral line at the midpoint of the core. Remove rectangular specimens from the front (Zone A), middle (Zone B) and rear (Zone C). Each specimen is centered along the longitudinal axis of the sample, is 50.8 mm in the longitudinal direction by 30 mm in the lateral direction and is the entire thickness of the product. Zone A specimen is centered 45.4 mm from the front edge of the product. Zone B is centered at the lateral mark on the sample. Zone C is centered at 45.4 mm from the rear of the product.

Program the tensile tester for a compression test, to move the crosshead down at a rate of 1.0 mm/sec for 25 mm collecting force (N) and displacement (m) data at 50 Hz, and return the crosshead to its original gage. Load a specimen such that it spans the two lower bars centered under the upper bar. A CD bend refers to bending along the longitudinal axis of the pad (longitudinal direction parallel to bars) and MD bend refers to bending along the lateral axis of the pad (lateral direction parallel to bars). Zero the crosshead and load cell. Start the run and collect data.

Construct a graph of force (N) verses displacement (mm). Read the maximum Peak Force from the graph and divide by the specimen width (m). Record as the Peak Force/Width to nearest 0.1 N/m. From the curve, calculate the Slope/Width as the greatest slope of a linear segment fitted to the curve, wherein the length of the segment incorporates 20% of the curve then divide by the width of the specimen and report to the nearest 0.1 N/mm*m.

Measures are repeated in like fashion for 10 MD and 10 CD specimens and report the average separately for each of the ten values to the nearest 0.1 N/m for Peak Force/Width and 0.1 N/mm*m for Slope/Width.

ZD Compression

The ZD compression of a specimen is measured on a constant rate of extension tensile tester (a suitable instrument is the MTS Alliance using Testworks 4.0 Software, as available from MTS Systems Corp., Eden Prairie, MN) using a load cell for which the forces measured are within 10% to 90% of the limit of the cell. The bottom stationary fixture is a circular, stainless steel platen 100 mm in diameter, and the upper movable fixture is a circular, stainless steel platen 40.00 mm in diameter. Both platens have adapters compatible with the mounts of the tensile tester, capable of securing the platens parallel to each other and orthogonal to the pull direction of the tensile tester. All testing is performed in a room controlled at 23° C.±3° C. and 50%±2% relative humidity.

Samples are conditioned at 23° C.±3° C. and 50%±2% relative humidity two hours prior to testing. Identify the longitudinal and lateral center of the product. Remove the layer of interest from the article using cryo-spray as needed. From the longitudinal and lateral midpoint, die cut a square 50.0±0.05 mm Specimens are prepared from five replicate samples.

Before the compression test can be performed, the caliper of a specimen is measured using a calibrated digital linear caliper (e.g., Ono Sokki GS-503 or equivalent) fitted with a 24.2 mm diameter foot with an anvil that is large enough that the specimen can lie flat. The foot applies a confining pressure of 0.69 kPa to the specimen. Zero the caliper foot against the anvil. Lift the foot and insert the specimen flat against the anvil with its longitudinal and lateral midpoint centered under the foot. Lower the foot at about 5 mm/sec onto the specimen. Read the caliper (mm) 5.0 sec after resting the foot on the specimen and record to the nearest 0.01 mm.

Set the nominal gage length between the platens to approximately 3 mm greater than the specimens to be tested. Place the specimen, body facing side upward, onto the bottom platen with the longitudinal and lateral midpoint of the specimen centered under the upper platen. Zero the crosshead and load cell. Lower the crosshead at 1.00 mm/s until the distance between the bottom surface of the upper platen and the upper surface of the bottom platen is equal to the measured caliper of the specimen. This is the adjusted gage length. Start data collection at a rate of 100 Hz. Lower the crosshead at 1.00 mm/s to 50% of the adjusted gage length. Hold for 0.00 sec and then return the crosshead to the adjusted gage length Immediately repeat this cycle for four additional cycles. Return the crosshead to the nominal gage length and remove the specimen. From the resulting Force (N) versus Displacement (mm) curves, calculate and record the Peak Force (N) for Cycle 1 and Cycle 5 to the nearest 0.01 N.

In like fashion, repeat the measure for a total of 5 replicate samples. Calculate and report the arithmetic mean for the five Peak Force (N) for Cycle 1 and Peak Force (N) for Cycle 5 values separately to the nearest 0.01N.

Kinetics and 1D Liquid Distribution by NMR-MOUSE

The NMR-MOUSE (Mobile Universal Surface Explorer) is a portable open NMR sensor equipped with a permanent magnet geometry that generates a highly uniform gradient perpendicular to the scanner surface. A frame 1007 with horizontal plane 1006 supports the specimen and remains stationary during the test. A flat sensitive volume of the specimen is excited and detected by a surface rf coil 1012 placed on top of the magnet 1010 at a position that defines the maximum penetration depth into the specimen. By repositioning the sensitive slice across the specimen by means of a high precision lift 1008, the scanner can produce one-dimensional profiles of the specimen's structure with high spatial resolution.

An exemplary instrument is the Profile NMR-MOUSE model PM25 with High-Precision Lift available from Magritek Inc., San Diego, CA. Requirements for the NMR-MOUSE are a 100 μm resolution in the z-direction, a measuring frequency of 13.5 MHz, a maximum measuring depth of 25 mm, a static gradient of 8 T/m, and a sensitive volume (x-y dimension) of 40 by 40 mm$^2$. Before the instrument can be used, perform phasing adjustment, check resonance frequency and check external noise level as per the manufacturer's instruction. A syringe pump capable of delivering test fluid in the range of 1 mL/min to 5 mL/min±0.01 mL/min is used to dose the specimen. All measurements are conducted in a room controlled at 23° C.±0.5° C. and 50%±2% relative humidity.

The test solution is Paper Industry Fluid (PIF) prepared as 15 g carboxymethylcellulose, 10 g NaCl, 4 g NaHCO$_3$, 80 g glycerol (all available from SigmaAldrich) in 1000 g distilled water. 2 mM/L of Diethylenetriaminepentaacetic acid gadolinium (III) dihydrogen salt (available from SigmaAldrich) is added to each. After addition the solutions are stirred using an shaker at 160 rpm for one hour. Afterwards the solutions are checked to assure no visible undissolved crystals remain. The solution is prepared 10 hours prior to use.

Products for testing are conditioned at 23° C.±0.5° C. and 50%±2% relative humidity for two hours prior to testing. Identify the intersection of the lateral and longitudinal center line of the product. Cut a 40.0 mm by 40.0 mm specimen from the product, centered at that intersection, with the cut edges parallel and perpendicular to the longitudinal axis of the product. The garment facing side of the specimen 1003 is mounted on a 50 mm×50 mm×0.30 mm glass slide 1001 using a 40.0 mm by 40.0 mm piece of double-sided tape 1002 (tape must be suitable to provide NMR Amplitude signal). A top cap 1004 is prepared by adhering two 50 mm×50 mm×0.30 mm glass slides 1001 together using a 40 mm by 40 mm piece of two-sided tape 1002. The cap is then placed on top of the specimen. The two tape layers are used as functional markers to define the dimension of the specimen by the instrument.

Figures 27A, 27B:
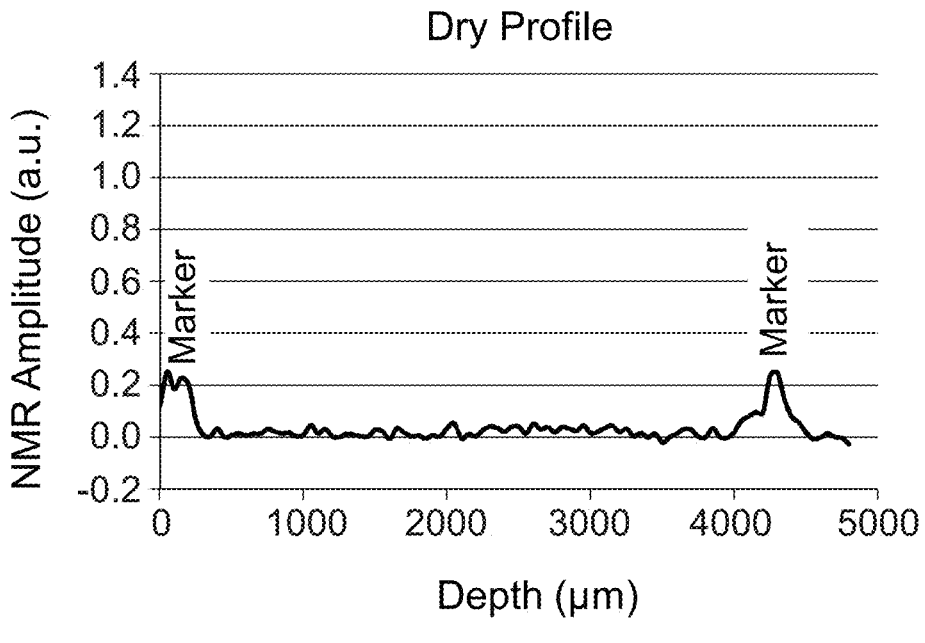
FIG. 27a shows a plot of an NMR profile.
FIG. 27b shows a plot of an NMR profile.

First a 1-D Dry Distribution Profile of the specimen is collected. Place the prepared specimen onto the instrument aligned over top the coils. Program the NMR-MOUSE for a Carr-Purcell-Meiboom-Gill (CPMG) pulse sequence consisting of a 90° x-pulse follow by a refocusing pulse of 180° y-pulse using the following conditions:

Repetition Time=500 ms
Number of Scans=8
Number of Echoes=8
Resolution=100 μm
Step Size=−100 μm
Collect NMR Amplitude data (in arbitrary units, a.u.) versus depth (μm) as the high precision lift steps through the specimen's depth. A representative graph is shown in FIG. 27a.

The second measure is the Kinetic Experiment of the test fluid moving though the sensitive NMR volume as test fluid is slowly added to the top of the specimen. The "trickle" dose is followed by a "gush" dose added using a calibrated dispenser pipet. Program the NMR-MOUSE for a CPMG pulse sequence using the following conditions:

Measurement Depth=5 mm
Repetition Time=200 ms
90° Amplitude=−7 dB
180° Amplitude=0 dB
Pulse Length=5 μs Echo Time=90 μs
Number of Echoes=128
Echo Shift=1 μs
Experiments before trigger=50
Experiments after trigger=2000
Rx Gain=31 dB
Acquisition Time=8 μs
Number of Scans=1
Rx Phase is determined during the phase adjustment as described by the vendor. A value of 230° was typical for our experiments. Pulse length depends on measurement depth which here is 5 mm. If necessary the depth can be adjusted using the spacer 1011.

43

Figure 28:
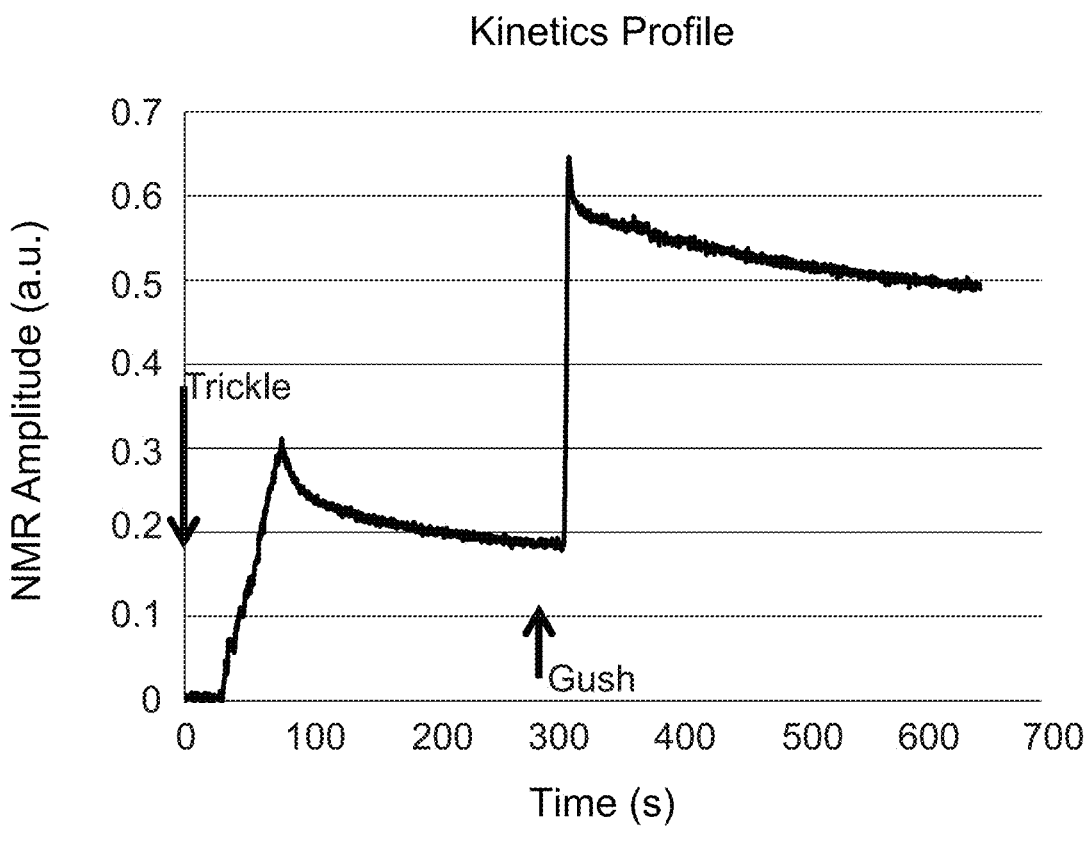
FIG. 28 shows a kinetic plot of an NMR profile.

Using the precision lift adjust the height of the specimen so that the desired target region is aligned with the instruments sensitive volume. Target regions can be chosen based on SEM cross sections. Program the syringe pump to deliver 1.00 mL/min±0.01 mL for 1.00 min for PIF test fluid or 5.00 mL/min±0.01 mL for 1.00 min for 0.9% Saline test fluid. Start the measurement and collect NMR Amplitude (a.u.) for 50 experiments before initiating fluid flow to provide a signal baseline. Position the outlet tube from the syringe pump over the center of the specimen and move during applying liquid over the total sample surface, but do not touch the borders of the sample. Trigger the system to continue collection of NMR amplitude data while simultaneously initiating fluid flow for 1 mL over 60 sec. At 300 sec after the trigger, add 0.50 mL of test fluid at approximately 0.5 mL/sec to the center of the specimen via a calibrated Eppendorf pipet. A representative example of the NMR Amplitude versus time graph is shown in FIG. 28. Utilizing the generated NMR Amplitude versus time graph following the second insult that is the 'gush dose' the % change in signal Amplitude versus time can be determined as well as the time required to reduce the Amplitude signal from its peak following the 'gush dose' by for example 20%, 30%, 50%, 75% or 100% can be determined. Reduction of signal amplitude occurs as fluid is absorbed and distributed beyond preset NMR viewing range.

The third measurement is a 1-D Wet Distribution Profile Immediately after the Kinetic measurement is complete, replace the cap on the specimen. The Wet Distribution is run under the same experimental conditions as the previous Dry Distribution, described above. A representative graph is shown in FIG. 27b.

Calibration of the NMR Amplitude for the Kinetic signal can be performed by filling glass vials (8 mm outer diameter and a defined inner diameter by at least 50 mm tall) with the appropriate fluid. Set the instrument conditions as described for the kinetics experiment. A calibration curve is constructed by placing an increasing number of vials onto the instrument (vials should be distributed equally over the 40 mm×40 mm measurement region) and perform the kinetic measurements. The volumes are calculated as the summed cross sectional area of the vials present multiplied by the z-resolution where Resolution (mm) is calculated as 1/Acquisition Time (s) divided by the instruments Gradient Strength (Hz/mm). The Calibration of the NMR Amplitude for the Distribution Profile is performed as an internal calibration based on the dry and wet profiles. In this procedure, the area beneath wet and dry profile were calculated and after subtracting them the total area (excluding markers) was obtained. This total area is correlated to the amount of applied liquid (here 1.5 mL). The liquid amount (μL) per 100 μm step can then be calculated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a transverse centerline,
a topsheet,
a backsheet, and
an absorbent core structure disposed between the topsheet and the backsheet,
    wherein the absorbent core structure comprises a heterogeneous mass comprising a fibrous nonwoven web layer and a high internal phase emulsion (HIPE) foam layer,
    wherein fibers of the nonwoven web have been displaced with the HIPE foam layer wherein the displaced fibers of the nonwoven web and the HIPE foam occupy the same plane,
    wherein the topsheet and the heterogeneous mass are integrated to form an integrated absorbent structure comprising a first zone, a second zone, and a third zone,
    wherein at least a first boundary and a second boundary divide the first zone, the second zone, and the third zone,
    wherein the first zone has an area located along a portion of a longitudinal centerline,
    wherein the second zone has an area disposed between the first zone and a first side edge and the third zone has an area disposed between the first zone and a second side edge,
    wherein the first boundary and the second boundary converge and meet at a point at a boundary convergence area,
    wherein the point of the boundary convergence area is disposed on the longitudinal centerline such that the first boundary and the second boundary meet the longitudinal centerline at the point of the boundary convergence area,
    wherein the first zone has a first pattern, the second zone has a second pattern, and the third zone has a third pattern,
    wherein the first pattern and the second pattern are different and the first pattern and the third pattern are different,
    wherein the first zone exhibits a first CD Peak Force/Width and the second zone exhibits a second CD Peak Force/Width,
    wherein the first CD Peak Force/Width is greater than the second Peak Force/Width, as measured using a Three Point Bend method described herein.

2. The absorbent article of claim 1, wherein the absorbent article comprises greater than two boundaries.

3. The absorbent article of claim 1, wherein the first boundary is one of a topographical, a mechanical, a visual, or a fluid handling property boundary.

4. The absorbent article of claim 1, wherein the second boundary is one of a topographical, a mechanical, a visual, or a fluid handling property boundary.

5. The absorbent article of claim 1, wherein the absorbent article comprises greater than three zones.

6. The absorbent article of claim 1, wherein each of the zones are irregularly shaped.

7. The absorbent article of claim 1, wherein the first zone and the second zone each exhibit different absorption rates.

8. The absorbent article of claim 1, wherein the boundary convergence area is positioned greater than 50% of a total length of the absorbent article along the longitudinal centerline from a front edge of the absorbent article.

9. The absorbent article of claim 1, wherein the fibers of the nonwoven web are displaced in a pattern of wells.

10. The absorbent article of claim 1, wherein the second pattern and the third pattern are the same.

11. An absorbent article comprising:

a transverse centerline, a topsheet, a backsheet, and an absorbent core structure disposed between the topsheet and the backsheet, wherein the absorbent core comprises a heterogeneous mass comprising a fibrous nonwoven web layer and a high internal phase emulsion (HIPE) foam layer, wherein fibers of the nonwoven web have been displaced with the HIPE foam layer, wherein the displaced fibers of the nonwoven web and the HIPE foam occupy the same plane, wherein the topsheet and the heterogeneous mass are integrated to form an integrated absorbent structure comprising a first zone, a second zone, a third zone and a fourth zone, wherein at least a first boundary and a second boundary divide the first zone, the second zone, and the third zone, wherein the first boundary and the second boundary converge and meet at an intersection point at a boundary convergence area positioned between a lateral centerline and a back edge and disposed on a longitudinal centerline such that the first boundary and the second boundary intersect the longitudinal centerline at the intersection point of the boundary convergence area, wherein the first zone has an area located along the longitudinal centerline and extending from the boundary convergence area to a front edge, wherein the second zone has an area disposed between the first zone and a first side edge and the third zone has an area disposed between the first zone and a second side edge, wherein the fourth zone extends from the boundary convergence area to the back edge, wherein the first zone has a first pattern, the second zone has a second pattern, the third zone has a third pattern, and the fourth zone has a fourth pattern, wherein the first pattern is different from each of the second pattern, the third pattern, and the fourth pattern, wherein the first zone exhibits a first CD Peak Force/Width and the second zone exhibits a second CD Peak Force/Width, and wherein the first CD Peak Force/Width and the second Peak Force/Width are different, as measured using a Three Point Bend method described herein.

12. The absorbent article of claim 11, wherein the first CD Peak Force/Width is greater than the second Peak Force/Width, as measured using a Three Point Bend method described herein.

13. The absorbent article of claim 11, wherein the fibers of the nonwoven web are displaced in a pattern of wells.

14. The absorbent article of claim 11, wherein the first zone is stiffer than each of the second zone and the third zone.

15. The absorbent article of claim 11, comprising a third boundary, wherein the third boundary separates at least two of the first zone, the second zone, the third zone, and the fourth zone.

16. The absorbent article of claim 11, wherein the third boundary coverage at the boundary convergence area.

17. The absorbent article of claim 1, wherein the first boundary crosses over the longitudinal centerline at the point of the boundary convergence area such that the first boundary is positioned between the longitudinal centerline and the first side edge between the boundary convergence area and the front edge and the first boundary is positioned between the longitudinal centerline and the second side edge between the boundary convergence area and the rear edge; and wherein the second boundary crosses over the longitudinal centerline at the point of the boundary convergence area such that the second boundary is positioned between the longitudinal centerline and the second side edge between the boundary convergence area and the front edge and the second boundary is positioned between the longitudinal centerline and the first side edge between the boundary convergence area and the rear edge.

18. The absorbent article of claim 11, wherein the first boundary crosses over the longitudinal centerline at the intersection point of the boundary convergence area such that the first boundary is positioned between the longitudinal centerline and the first side edge between the boundary convergence area and the front edge and the first boundary is positioned between the longitudinal centerline and the second side edge between the boundary convergence area and the rear edge; and wherein the second boundary crosses over the longitudinal centerline at the point of the boundary convergence area such that the second boundary is positioned between the longitudinal centerline and the second side edge between the boundary convergence area and the front edge and the second boundary is positioned between the longitudinal centerline and the first side edge between the boundary convergence area and the rear edge.

* * * * *